United States Patent
Okura et al.

(10) Patent No.: US 6,790,442 B1
(45) Date of Patent: Sep. 14, 2004

(54) GENOMIC DNA ENCODING A POLYPEPTIDE CAPABLE OF INDUCING THE PRODUCTION OF INTERFERON-γ

(75) Inventors: Takanori Okura, Okayama (JP); Kakuji Torigoe, Okayama (JP); Masashi Kurimoto, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/479,862

(22) Filed: Jan. 10, 2000

Related U.S. Application Data

(62) Division of application No. 08/884,324, filed on Jun. 27, 1997, now Pat. No. 6,060,283.

(30) Foreign Application Priority Data

Jun. 27, 1996 (JP) .............................................. 8-185305

(51) Int. Cl.[7] .............................................. A01N 63/00
(52) U.S. Cl. .................. 424/93.2; 424/93.7; 435/320.1; 435/325; 435/455; 435/456; 435/458
(58) Field of Search .............................. 435/320.1, 455, 435/456, 458, 325, 365.1; 424/93.1, 93.2, 93.21, 93.7

(56) References Cited

U.S. PATENT DOCUMENTS 5,166,066 A   11/1992   Carter .................... 435/240.2

FOREIGN PATENT DOCUMENTS

| EP | 0692536 | 1/1996 |
| EP | 0712931 | 5/1996 |
| EP | 0712931 A2 | 5/1996 |
| EP | 0861663 A2 | 2/1998 |

OTHER PUBLICATIONS

G Romano et al., Stem Cells, "Latest Developments in Gene Transfer Technology: Achievements, Perspectives, and Controversies over Therapeutic Applications," 2000, 18:19–39.*

J Golab, Cytokine, "Interleukin 18—Interferon beta inducing Factor—A Novel Player in Tumour Immunotherapy?," Apr. 2000, vol. 12, No. 4, pp. 332–338.*

WF Anderson, Nature, "Human gene therapy," Apr. 1998, vol. 392, Supp., pp. 25–30.*

Ushio et al., "Cloning of the CDNA for human IF–Nγ–inducing factor, expression in *Escherichia coli*, and studies on the biologic activities of the protein", *The Journal of Immunology*, vol. 156: 11 pages 4274–4279 (Jun. 1, 1996).

Ballast et al., "Characterization and chromosomal localizationof the human interleukin–18 gene", *BLOOD*, vol. 90, No. 10, part 2 suppl. 1 p. 177b (Nov. 15, 1997).

Minowada, "Leukemia Cell Lines", *Cancer Review*, vol. 10, pp. 1–18, 1988.

Hay et al., "Cell Lines and Hybridomas", *ATCC*, Eighth Edition, pp. 127, 129, 131, 152, 207, 339, 1994.

Kostura et al., "Indentification of a Monocyte Specific Pre–Interleukin 1B Convertase Activity", *Proc. Natl. Acad. Sci. USA*, vol. 86, pp. 5227–5231, Jul. 1989.

Shimada et al., "Basic Techniques for Gene Therapy", *Biomanual Up Series*, 1996.

Yokota et al., "The Experimental Methods for the Gene Cloning", *Biomanual Series 3*, 1993.

Kuriki et al., "The Handbook for the Cell Engineering", Saibo–Kagaku Handbook, 1992.

Rothe, H., et al. (1997) *J. Clin. Invest.* 99: 469–74.
Nolan, K.F., et al. (1998) *Genomics* 51: 161–63.

* cited by examiner

Primary Examiner—Ram R. Shukla
(74) Attorney, Agent, or Firm—Browdy and Neimark, PLLC

(57) ABSTRACT

Disclosed is a genomic DNA encoding a polypeptide capable of inducing the production of interferon-γ by immunocompetent cells. The genomic DNA efficiently expresses the polypeptide with high biological activities of such as inducing the production of interferon-γ by immunocompetent cells, enhancing killer cells' cytotoxicity and inducing killer cells' formation, when introduced into mammalian host cells. The high biological activities of the polypeptide facilitate its uses to treat and/or prevent malignant tumors, viral diseases, bacterial infectious diseases and immune diseases without serious side effects when administered to humans.

5 Claims, 1 Drawing Sheet

Figure 1:
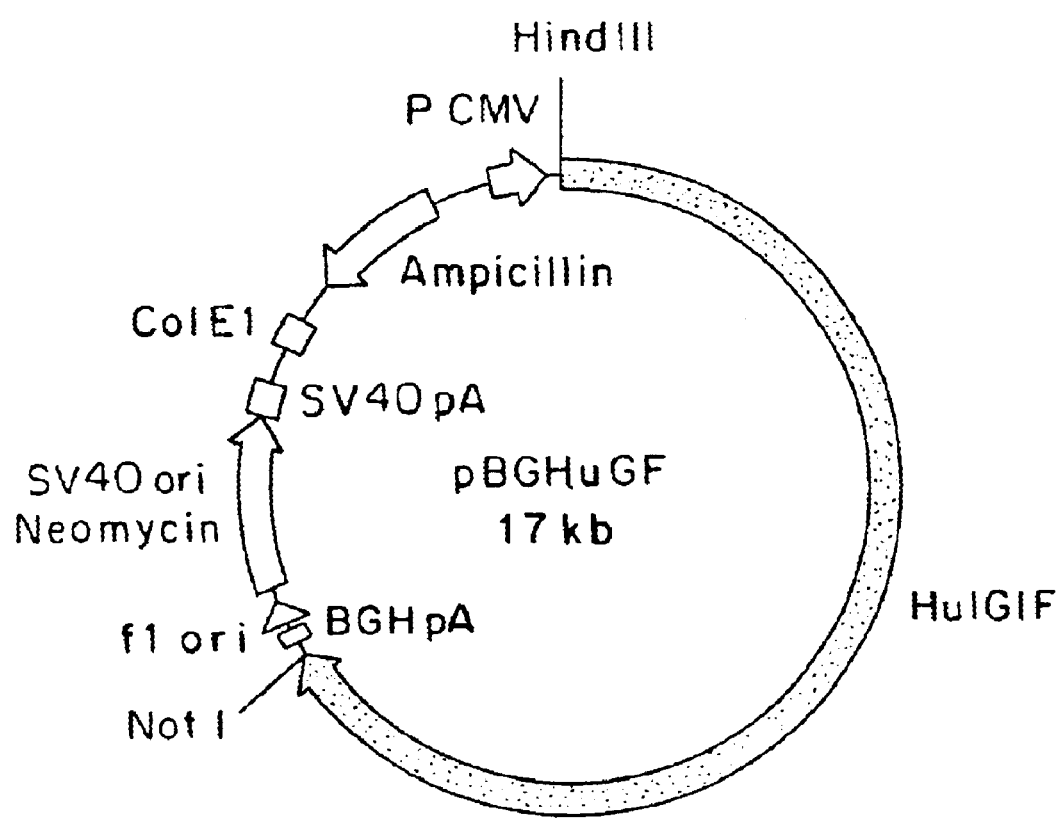

GENOMIC DNA ENCODING A POLYPEPTIDE CAPABLE OF INDUCING THE PRODUCTION OF INTERFERON-γ

CROSS-REFERENCE TO RELATED APPLICATIONS

This is a divisional of parent application Ser. no. 08/884,324, filed Jun. 27, 1997, now U.S. Pat. No. 6,060,283, issued May 9, 2000.

BACKGROUND OF THE INVENTION

1. Field of the Invention

The present invention relates to a genomic DNA, more particularly, a genomic DNA encoding a polypeptide capable of inducing the production of interferon-γ (hereinafter abbreviated as "IFN-γ") by immunocompetent cells.

2. Description of the Prior Art

The present inventors successfully isolated a polypeptide capable of inducing the production of IFN-γ by immunocompetent cells and cloned a cDNA encoding the polypeptide, which is disclosed in Japanese Patent Kokai No. 27,189/96 and 193,098/96. Because the present polypeptide possesses the properties of enhancing killer cells' cytotoxicity and inducing killer cells' formation as well as inducing IFN-γ, a useful biologically active protein, it is expected to be widely used as an agent for viral diseases, microbial diseases, tumors and/or immunopathies, etc.

It is said that a polypeptide generated by a gene expression may be partially cleaved and/or glycosylated by processing with intracellular enzymes in human cells. A polypeptide to be used in therapeutic agents should be preferably processed similarly as in human cells, whereas human cell lines generally have a disadvantage of less producing the present polypeptide, as described in Japanese Patent Application No.269,105/96. Therefore, recombinant DNA techniques should be applied to obtain the present polypeptide in a desired amount. To produce the polypeptide processed similarly as in human cells using recombinant DNA techniques, mammalian cells should be used as the hosts.

SUMMARY OF THE INVENTION

In view of foregoing, the first object of the present invention is to provide a DNA which efficiently expresses the polypeptide production when introduced into a mammalian host cell.

The second object of the present invention is to provide a transformant into which the DNA is introduced.

The third object of the present invention is to provide a process for preparing a polypeptide, using the transformant.

[Means to Attain the Object]

The present inventors' energetic studies to attain the above objects succeeded in the finding that a genomic DNA encoding the present polypeptide efficiently expresses the polypeptide production when introduced into mammalian host cells. They found that the polypeptide thus obtained possessed significantly higher biological activities than that obtained by expressing a cDNA encoding the polypeptide in *Escherichia coli*.

The first object of the present invention is attained by a genomic DNA encoding a polypeptide with the amino acid sequence of SEQ ID NO:1 (where the symbol "Xaa" means "isoleucine" or "threonine") or its homologous one, which induces interferon-γ production by immunocompetent cells.

The second object of the present invention is attained by a transformant formed by introducing the genomic DNA into a mammalian host cell.

The third object of the present invention is attained by a process for preparing a polypeptide, which comprises (a) culturing the transformant in a nutrient medium, and (b) collecting the polypeptide from the resultant culture.

BRIEF EXPLANATION OF THE ACCOMPANYING DRAWINGS

FIG. 1 is a restriction map of a recombinant DNA containing a genomic DNA according to the present invention.

Explanation of the symbols are as follows: The symbol "Hin dIII" indicates a cleavage site by a restriction enzyme Hin dIII, and the symbol "HuIGIF" indicates a genomic DNA according to the present invention.

DETAILED DESCRIPTION OF THE INVENTION

The followings are the preferred embodiments according to the present invention. This invention is made based on the identification of a genomic DNA encoding the polypeptide with the amino acid sequence of SEQ ID NO:1 or its homologous one, and the finding that the genomic DNA efficiently expresses the polypeptide with high biological activities when introduced into mammalian host cells. The genomic DNA of the present invention usually contains two or more exons, at least one of which possesses a part of or the whole of the nucleotide sequence of SEQ ID NO:2. The wording "a part" includes a nucleotide and a sequential nucleotides consisting of two or more nucleotides in SEQ ID NO:2. Examples of the exons are SEQ ID NOs:3 and 4. Human genomic DNA may contain additional exons with SEQ ID NOs:5 to 7. Since the present genomic DNA is derived from a mammalian genomic DNA, it contains introns, as a distinctive feature in mammalian genomic DNAs. The present genomic DNA usually has two or more introns such as SEQ ID NOs:8 to 12.

More particular examples of the present genomic DNA include DNAs with SEQ ID NOs:13 and 14 or complementary sequences thereunto. The DNAs with SEQ ID NOs:13 and 14 are substantially the same. The DNA with SEQ ID NO:14 contains coding regions for a leader peptide, consisting of the nucleotides 15,607th–15,685th, 17,057th–17,068th and 20,452nd–20,468th, coding regions for the present polypeptide, consisting of the nucleotides 20,469th–20,586th, 21,921st–22,054th and 26,828th–27,046th, and regions as introns, consisting of the nucleotides 15,686th–17,056th, 17,069–20,451st, 20,587th–21,920th and 22,055th–26,827th. The genomic DNA with SEQ ID NO:13 is suitable for expressing the polypeptide in mammalian host cells.

Generally in this field, when artificially expressing a DNA encoding a polypeptide in a host, one or more nucleotides in a DNA may be replaced by different ones, and appropriate promoter(s) and/or enhancer(s) may be linked to the DNA to improve the expressing efficiency or the properties of the expressed polypeptide. The present genomic DNA can be altered similarly as above. Therefore, as far as not substantially changing in the biological activities of the expressed polypeptides, the present genomic DNA should include DNAs encoding functional equivalents of the polypeptide, formed as follows: One or more nucleotides in SEQ ID NOs:3 to 14 are replaced by different ones, the untranslated regions and/or the coding region for a leader peptide in the 5'- and/or 3'-termini of SEQ ID NOs:3, 4, 5, 6, 7, 13 and 14 are deleted, and appropriate oligonucleotides are linked to either or both ends of SEQ ID NO:13.

The present genomic DNA includes general DNAs which are derived from a genome containing the nucleotide sequences as above, and it is not restricted to its sources or origins as far as it is once isolated from its original organisms. For example, the present genomic DNA can be obtained by chemically synthesizing based on SEQ ID NOs:2 to 14, or by isolating from a human genomic DNA. The isolation of the present genomic DNA from such a human genomic DNA comprises (a) isolating a genomic DNA from human cells by conventional methods, (b) screening the genomic DNA with probes or primers, which are chemically synthesized oligonucleotides with a part of or the whole of the nucleotide sequence of SEQ ID NO:2, and (c) collecting a DNA to which the probes or primers specifically hybridize. Once the present genomic DNA is obtained, it can be unlimitedly replicated by constructing a recombinant DNA with an autonomously replicable vector by conventional method and then introducing the recombinant DNA into an appropriate host such as a microorganism or an animal cell before culturing the transformant or by applying a PCR method.

The present genomic DNA is very useful in producing the polypeptide by recombinant DNA techniques since it efficiently expresses the polypeptide with high biological activities when introduced into mammalian host cells. The present invention further provides a process for preparing a polypeptide using a specific genomic DNA, comprising the steps of (a) culturing a transformant formed by introducing the present genomic DNA into mammalian host cells, and (b) collecting the polypeptide which induces IFN-γ production by immunocompetent cells from the resultant culture.

The following explains the process for preparing the polypeptide according to the present invention. The present genomic DNA is usually introduced into host cells in the form of a recombinant DNA. The recombinant DNA, comprising the present genomic DNA and an autonomously replicable vector, can be relatively easily prepared by conventional recombinant DNA techniques when the genomic DNA is available. The vectors, into which the present genomic DNA can be inserted, include plasmid vectors such as pcD, pcDL-SRα, pKY4, pCDM8, pCEV4 and pME18S. The autonomously replicable vectors usually further contain appropriate nucleotide sequences for the expression of the present recombinant DNA in each host cell, which include sequences for promoters, enhancers, replication origins, transcription termination sites, splicing sequences and/or selective markers. Heat shock protein promoters or IFN-α promoters, as disclosed in Japanese Patent Kokai No. 163, 368/95 by the same applicant of this invention, enables to artificially regulate the present genomic DNA expression by external stimuli.

To insert the present genomic DNA into vectors, conventional methods used in this field can be arbitrarily used: Genes containing the present genomic DNA and autonomously replicable vectors are cleaved with restriction enzymes and/or ultrasonic, and the resultant DNA fragments and the resultant vector fragments are ligated. To cleave genes and vectors by restriction enzymes, which specifically act on nucleotides, more particularly, AccI, BamHI, BglII, BstXI, EcoRI, HindIII, NotI, PstI, SacI, SalI, SmaI, SpeI, XbaI, XhoI, etc., facilitate the ligation of the DNA fragments and the vector fragments. To ligate the DNA fragments and the vector fragments, they are, if necessary, first annealed, then treated with a DNA ligase in vivo or in vitro. The recombinant DNAs thus obtained can be unlimitedly replicated in hosts derived from microorganisms or animals.

Any cells conventionally used as hosts in this field can be used as the host cells: Examples of such are epithelial, interstitial and hemopoietic cells, derived from human, monkey, mouse and hamster, more particularly, 3T3 cells, C127 cells, CHO cells, CV-1 cells, COS cells, HeLa cells, MOP cells and their mutants. Cells which inherently produce the present polypeptide also can be used as the host cells: Example of such are human hemopoietic cells such as lymphoblasts, lymphocytes, monoblasts, monocytes, myeloblasts, myelocytes, granulocytes and macrophages, and human epithelial and interstitial cells derived from solid tumors such as pulmonary carcinoma, large bowel cancer and colon cancer. More particular examples of the latter hemopoietic cells are leukemia cell lines such as HBL-38 cells, HL-60 cells ATCC CCL240, K-562 cells ATCC CCL243, KG-1 cells ATCC CCL246, Mo cells ATCC CRL8066, THP-1 cells ATCC TIB202, U-937 cells ATCC CRL1593.2, described by J. Minowada et al. in "Cancer Research", Vol.10, pp.1–18 (1988), derived from leukemias or lymphoma including myelogenous leukemias, promyelocytic leukemias, monocytic leukemias, adult T-cell leukemias and hairy cell leukemias, and their mutants. The present polypeptide-processibility of these leukemia cell lines and their mutants is so distinguished that they can easily yield the polypeptide with higher biological activities when used as hosts.

To introduce the present DNA into the hosts, conventional methods such as DEAE-dextran method, calcium phosphate transfection method, electroporation method, lipofection method, microinjection method, and viral infection method as using retrovirus, adenovirus, herpesvirus and vaccinia virus, can be used. The polypeptide-producing clones in the transformants can be selected by applying the colony hybridization method or by observing the polypeptide production after culturing the transformants in culture media. For example, the recombinant DNA techniques using mammalian cells as hosts are detailed in "jikken-Igaku-Bessatsu Saibo-Kogaku Handbook (The handbook for the cell engineering)" (1992), edited by Toshio KUROKI, Masaru TANIGUCHI and Mitsuo OSHIMURA, published by YODOSHA. CO., LTD., Tokyo, Japan, and "Jikken-Igaku-Bessatsu Biomanual Series 3 Idenshi Cloning Jikken-Ho (The experimental methods for the gene cloning)" (1993), edited by Takahi YOKOTA and Ken-ichi ARAI, published by YODOSHA CO., LTD., Tokyo, Japan.

The transformants thus obtained secrete the present polypeptide intracellularly and/or extracellularly when cultured in culture media. As the culture media, conventional ones used for mammalian cells can be used. The culture media generally comprise (a) buffers as a base, (b) inorganic ions such as sodium ion, potassium ion, calcium ion, phosphoric ion and chloric ion, (c) micronutrients, carbon sources, nitrogen sources, amino acids and vitamins, which are added depending on the metabolic ability of the cells, and (d) sera, hormones, cell growth factors and cell adhesion factors, which are added if necessary. Examples of individual media include 199 medium, DMEM medium, Ham's F12 medium, IMDM medium, MCDB 104 medium, MCDB 153 medium, MEM medium, RD medium, RITC 80–7 medium, RPMI-1630 medium, RPMI-1640 medium and WAJC 404 medium. The cultures containing the present polypeptide are obtainable by inoculating the transformants into the culture media to give a cell density of $1\times10^4$–$1\times10^7$ cells/ml, more preferably, $1\times10^5$–$1\times10^5$ cells/ml, and then subjecting to suspension- or monolayer-cultures at about 37°

C. for 1–7 days, more preferably, 2–4 days, while appropriately replacing the culture media with a fresh preparation of the culture media. The cultures thus obtained usually contain the present polypeptide in a concentration of about 1–100 μg/ml, which may vary depending on the types of the transformants or the culture conditions used.

While the cultures thus obtained can be used intact as an IFN-γ inducer, they are usually subjected to a step for separating the present polypeptide from the cells or the cell debris using filtration, centrifugation, etc. before use, which may follow a step for disrupting the cells with supersonication, cell-lytic enzymes and/or detergents if desired, and to a step for purifying the polypeptide. The cultures from which the cells or cell debris are removed are usually subjected to conventional methods used in this field for purifying biologically active polypeptides, such as salting-out, dialysis, filtration, concentration, separatory sedimentation, ion-exchange chromatography, gel filtration chromatography, adsorption chromatography, chromatofocusing, hydrophobic chromatography, reversed phase chromatography, affinity chromatography, gel electrophoresis and/or isoelectric focusing. The resultant purified polypeptide can be concentrated and/or lyophilized into liquids or solids depending on final uses. The monoclonal antibodies disclosed in Japanese Patent Kokai No. 231,598/96 by the same applicant of this invention are extremely useful to purify the present polypeptide. Immunoaffinity chromatography using monoclonal antibodies yields the present polypeptide in a relatively high purity at the lowest costs and labors.

The polypeptide obtainable by the process according to the present invention exerts strong effects in the treatment and/or the prevention for IFN-γ- and/or killer cell-susceptive diseases since it possesses the properties of enhancing killer cells' cytotoxicity and inducing killer cells' formation as well as inducing IFN-γ, a useful biologically active protein, as described above. The polypeptide according to the present invention has a high activity of inducing IFN-γ, and this enables a desired amount of IFN-γ production with only a small amount. The polypeptide is so low toxic that it scarcely causes serious side effects even when administered in a relatively-high dose. Therefore, the polypeptide has an advantage that it can readily induce IFN-γ in a desired amount without strictly controlling the dosage. The uses as agents for susceptive diseases are detailed in Japanese Patent Application No. 28,722/96 by the same applicant of this invention.

The present genomic DNA is also useful for so-called "gene therapy". According to conventional gene therapy, the present DNA can be introduced into patients with IFN-γ- and/or killer cell-susceptive diseases by directly injecting after the DNA is inserted into vectors derived from viruses such as retrovirus, adenovirus and adeno-associated virus or is incorporated into cationic- or membrane fusible-liposomes, or by self-transplanting lymphocytes which are collected from patients before the DNA is introduced. In adoptive immunotherapy with gene therapy, the present DNA is introduced into effector cells similarly as in conventional gene therapy. This can enhance the cytotoxicity of the effector cells to tumor cells, resulting in improvement of the adoptive immunotherapy. In tumor vaccine therapy with gene therapy, tumor cells from patients, into which the present genomic DNA is introduced similarly as in conventional gene therapy, are self-transplanted after proliferated ex vivo up to give a desired cell number. The transplanted tumor cells act as vaccines in the patients to exert a strong antitumor immunity specifically to antigens. Thus, the present genomic DNA exhibits considerable effects in gene therapy for diseases including viral diseases, microbial diseases, malignant tumors and immunopathies. The general procedures for gene therapy are detailed in "Jikken-Igaku-Bessatsu Biomanual UP Series Idenshichiryo-no-Kisogijutsu (Basic techniques for the gene therapy)" (1996), edited by Takashi ODAJIMA, Izumi SAITO and Keiya OZAWA, published by YODOSHA CO., LTD., Tokyo, Japan.

The following examples explain the present invention, and the techniques used therein are conventional ones used in this field: For example, the techniques are described in "Jikken-Igaku-Bessatsu Saibo-Kogaku Handbook (The handbook for the cell engineering)", (1992), edited by Toshio KUROKI, Masaru TANIGUCHI and Mitsuo OSHIMURA, published by YODOSHA CO., LTD., Tokyo, Japan, and "Jikken-Igaku-Bessatsu Biomanual Series 3 Idenshi Clonong Jikken-Ho (The experimental methods for the gene cloning)" (1993), edited by Takahi YOKOTA and Ken-ichi ARAI, published by YODOSHA CO., LTD., Tokyo, Japan.

EXAMPLE 1

Cloning Genomic DNA and Determination of Nucleotide Sequence

EXAMPLE 1-1

Determination of Partial Nucleotide Sequence

Five ng of "PromoterFinder™ DNA PvuII LIBRARY", a human placental genomic DNA library commercialized by CLONTECH Laboratories, Inc., California, USA, 5 μl of 10×Tth PCR reaction solution, 2.2 μl of 25 mM magnesium acetate, 4 μl of 2.5 mM dNTP-mixed solution, one μl of the mixed solution of 2 unit/μl rTth DNA polymerase XL and 2.2 μg/μl Tth Start Antibody in a ratio of 4:1 by volume, 10 pmol of an oligonucleotide with the nucleotide sequence of 5'-CCATCCTAATACGACTCACTATAGGGC-3' (SEQ ID NO:16) as an adaptor primer, and 10 pmol of an oligonucleotide with the nucleotide sequence of 5'-TTCCTCTTCCCGAAGCTGTGTAGACTGC-3' (SEQ ID NO: 17) as an anti-sense primer, which was chemically synthesized based on the sequence of the nucleotides 88th–115th in SEQ ID NO:2, were mixed and volumed up to 50 μl with sterilized distilled water. After incubating at 94° C. for one min, the mixture was subjected to 7 cycles of incubations at 94° C. for 25 sec and at 72° C. for 4 min, followed by 32 cycles of incubations at 94° C. for 25 sec at 67° C. for 4 min to perform PCR.

The reaction mixture was diluted by 100 folds with sterilized distilled water. One μl of the dilution, 5 μl of 10×Tth PCR reaction solution, 2.2 μl of 25 mM magnesium acetate, 4 μl of 2.5 mM dNTP-mixed solution, one μl of the mixed solution of 2 unit/μl rTth DNA polymerase XL and 2.2 μg/μl Tth Start Antibody in a ratio of 4:1 by volume, 10 pmol of an oligonucleotide with the nucleotide sequence of 5'CTATAGGGCACGCGTGGT-3' (SEQ ID NO:13) as a nested primer, and 10 pmol of an oligonucleotide with the nucleotide sequence of 5'TTCCTCTTCCCGAAGCTGTGTAGACTOC-3' (SEQ ID NO:19) as an anti-sense primer, which was chemically synthesized similarly as above, were mixed and volumed up to 50 μl with sterilized distilled water. After incubating at 94° C. for one min, the mixture was subjected to 5 cycles of incubations at 94° C. for 25 sec and at 72° C. for 4 min, followed by 22 cycles of incubations at 94° C. for 25 sec and at 67° C. for 4 min to perform PCR for amplifying a DNA fragment of the present genomic DNA. The genomic DNA library and reagents for PCR used above were mainly from "PromoterFinder™ DNA WALKING KITS", commercialized by CLONTECH Laboratories, Inc., Calif., USA.

An adequate amount of the PCR product thus obtained was mixed with 50 ng of "pT7 Blue(R)", a plasmid vector commercialized by Novagen, Inc., WI, USA, and an adequate amount of T4 DNA ligase, and 100 mM ATP was added to give a final concentration of one mM, followed by incubating at 16° C. for 18 hr to insert the DNA fragment into the plasmid vector. The obtained recombinant DNA was introduced into an Escherichia coil JM109 strain by the competent cell method to form a transformant, which was then inoculated into L-broth medium (pH 7.2) containing 50 μg/ml ampicillin and cultured at 37° C. for 18 hr. The cells were isolated from the resulting culture, and then subjected to the conventional alkali-SDS method to collect a recombinant DNA. The dideoxy method analysis confirmed that the recombinant DNA contained the DNA fragment with a sequence of the nucleotides 5,150th–6,709th in SEQ ID NO:14.

EXAMPLE 1-2

Determination of Partial Nucleotide Sequence

PCR was performed in the same conditions as the first PCR in Example 1-1, but an oligonucleotide with the nucleotide sequence of 5'-GTAAGTTTTCACCTTCCAACTGTAGAGTCC-3', (SEQ ID NO:20) which was chemically synthesized based on the nucleotide sequence of the DNA fragment in Example 1-1, was used as an anti-sense primer.

The reaction mixture was diluted by 100 folds with sterilized distilled water. One μl of the dilution was placed into a reaction tube, and PCR was performed in the same conditions as used in the second PCR in Example 1-1 to amplify another DNA fragment of the present genomic DNA, but an oligonucleotide with the nucleotide sequence of 5'-GGGATCAAGTAGTGATCAGAAGCAGCACAC-3', (SEQ ID NO:21) which was chemically synthesized based on the nucleotide sequence of the DNA fragment in Example 1-1, was used as an anti-sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 1st–5,228th in SEQ ID NO:14.

EXAMPLE 1-3

Determination of Partial Nucleotide Sequence 0.5 μg of a human placental genomic DNA, commercialized by CLONTECH Laboratories, Inc., California, USA, 5 μl of 10×PCR reaction solution, 8 μl of 2.5 mM dNTP-mixed solution, one μl of the mixed solution of 5 unit/μl "TAKARA LA Taq POLYMERASE" and 1.1 μg/μl "Taqstart ANTIBODY" in a ratio of 1:1 by volume, both of them are commercialized by Takara Syuzo Co., Tokyo, Japan, 10 pmol of an oligonucleotide with the nucleotide sequence of 5'-CCTGGCTGCCAACTCTGGCTGCTAAAGCGG-3' (SEQ ID NO:22) as a sense primer, chemically synthesized based on a sequence of the nucleotides 46th–75th in SEQ ID NO:2, and 10 pmol of an oligonucleotide with the nucleotide sequence of 5'-GTATTGTCAATAAATTTCATTGCCACAAAGTTG-3' (SEQ ID NO:23) as an anti-sense primer, chemically synthesized based on a sequence of the nucleotides 210th–242nd in SEQ ID NO:2, were mixed and volumed up to 50 μl with sterilized distilled water. After incubating at 94° C. for one min, the mixture was subjected to 5 cycles of incubations at 98° C. for 20 sec and at 68° C. for 10 min, followed by 25 cycles of incubations at 98° C. for 20 sec and 68° C. for 10 min, with adding 5 sec in times to every cycle, and finally incubated at 72° C. for 10 min to amplify further DNA fragment of the present genomic DNA. The reagents for PCR used above were mainly from "TAKARA LA PCR KIT VERSION 2", commercialized by Takara Syuzo Co., Tokyo, Japan.

The DNA fragment was inserted into the plasmid vector similarly as in Example 1-1 to obtain a recombinant DNA. The recombinant DNA was replicated in *Escheritchia coli* before being collected. The analysis of the collected recombinant DNA confirmed that it contained the DNA fragment with a sequence of the nucleotides 6,640th–15,671st in SEQ ID NO:14.

EXPERIMENT 1-4

Determination of Martial Nucleotide Sequence

PCR was performed in the same conditions as the PCR in Example 1-3 to amplify further another DNA fragment of the present genomic DNA; but an oligonucleotide with the nucleotide sequence of 5'-AAGATGGCTGCTGAACCAGTAGAAGACAATTGC-3', (SEQ ID NO:24) chemically synthesized based on a sequence of the nucleotide 175th–207th in SEQ ID NO:2, was used as a sense primer, an oligonucleotide with the nucleotide sequence of 5'-TCCTTGGTCAATGAAGAGAACTTGGTC-3', (SEQ ID NO:25) chemically synthesized based on a sequence of nucleotides 334th–360th in the SEQ ID NO:2, was used as an anti-sense primer, and after incubating at 98° C. for 20 sec, the reaction mixture was subjected to 30 cycles of incubations at 98° C. for 20 sec and at 68° C. for 3 min, followed by incubating at 72° C. for 10 min.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 15,604th–20,543rd in SEQ ID NO:14.

EXAMPLE 1-5

Determination of Partial Nucleotide Sequence

PCR was performed in the same conditions as the PCR in Example 1-4 to amplify further another DNA fragment of the present genomic DNA, but an oligonucleotide with the nucleotide sequence of 5'-CCTGGAATCAGATTACTTTGGCAAGCTTGAATC-3', (SEQ ID NO:26) chemically synthesized based on the sequence of the nucleotide 273rd–305th in SEQ ID NO:2, was used as a sense primer, and an oligonucleotide with the nucleotide sequence of 5'-AGGAAATAATTTTGTTCTCACAGGAGAGAGTTG-3', (SEQ ID NO:27) chemically synthesized based on the sequence of nucleotides 500th–531st in the SEQ ID NO:2, was used as an anti-sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 20,456th–22,048th in SEQ ID NO:14.

EXAMPLE 1-6

Determination of Partial Nucleotide Sequence

PCR was performed in the same conditions as the PCR in Example 1-4 to amplify further another DNA fragment of the present genomic DNA, but an oligonucleotide with the nucleotide sequence of 5'-GCCAGCCTAGAGGTATGGCTGTAACTATCTC-3', (SEQ ID NO:28) chemically synthesized based on the sequence of the nucleotide 449th–479th in SEQ ID NO:2, was used as a sense primer, and an oligonucleotide with the nucleotide sequence of 5'-GGCATGAAATTTTAATAGCTAGTCTTCGTTTTG-3', (SEQ ID NO:29) chemically synthesized based on the sequence of nucleotides 745th–777th in the SEQ ID NO:2, was used as an anti-sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 21,996th–27,067th in SEQ ID NO:14.

EXAMPLE 1-7

Determination of Partial Nucleotide Sequence

PCR was performed in the same conditions as the first PCR in Example 1-2 to amplify further another DNA fragment in the present genomic DNA, but an oligonucleotide with the nucleotide sequence of 5'-GTGACATCATATTCTTTCAGAGAAGTGTCC-3', (SEQ ID NO:30) chemically synthesized based on the sequence of the nucleotide 575th–604th in SEQ ID NO:2, was used as a sense primer.

The reaction mixture was diluted by 100 folds with sterilized distilled water. One μl of the dilution was placed into a reaction tube, and PCR was performed in the same conditions as the second PCR in Example 1-2 to amplify further another DNA fragment of the present genomic DNA, but an oligonucleotide with the sequence of 5'-GCAATTTGAATCTTCATCATACGAAGGATAC-3', chemically synthesized based on a sequence of the nucleotides 624th–654th in SEQ ID NO:2, was used as a sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 26,914th–28,994th in SEQ ID NO:14.

EXAMPLE 1-8

Determination of Complete Nucleotide Sequence

Comparing the nucleotide sequence of SEQ ID NO:2, which was proved to encode the present polypeptide, as disclosed in Japanese Patent Kokai No.193,098/96 by the same applicant of this invention, with the partial nucleotide sequences identified in Examples 1-1 to 1-7, it was proved that the present genomic DNA contained the nucleotide sequence of SEQ ID NO:14. SEQ ID NO:14, consisting of 28,994 base pairs (bp), was extremely longer than the SEQ ID NO:2, consisting of only 471 bp. This suggested that SEQ ID NO:14 contained introns, a characteristic of eukaryotic cells.

It was examined where partial nucleotide sequences of SEQ ID NO:2, i.e., exons, and the donor and acceptor sites in introns, respectively consisting of the nucleotides of GT and AG, located in SEQ ID NO:14. Consequently, it was proved that SEQ ID NO:14 contained at least 5 introns, which located in the order of SEQ ID NOs:10, 11, 12, 8 and 9 in the direction from the 5'- to the 3'-termini. Therefore, the sequences between the neighboring introns must be exons, which were thought to be located in the order of SEQ ID NOs:5, 6, 3, 4 and 7 in the direction from the 5'- to the 3'-termini. It was also proved that SEQ ID NO:7 contained the 3'-untranslated region other than the exons. The features of the sequence elucidated as this are arranged in SEQ ID NO:14.

As disclosed in Japanese patent application by the same applicant of this invention, the present polypeptide is produced as a polypeptide with N-terminal amino acid of tyrosine other than methionine in human cells, which is observed in SEQ ID NO:1. This suggests that the present genomic DNA contains a leader peptide region in the upstream of the 5'-terminus of the present polypeptide-encoding region. A sequence consisting of 36 amino acids encoded by the upstream of the nucleotides 20,469th–20, 471st. which is the nucleotides of TAC, are described as a leader peptide in SEQ ID NO:14.

EXAMPLE 2

Preparation of Recombinant DNA pBGHuGF for Expression 0.06 ng of the DNA fragment in Example 1-4 in a concentration of 3 ng/50 μl, 0.02 ng of the DNA fragment, obtained by the methods in Example 1-5, 5 μl of 10×LA PCR reaction solution, 8 μl of 2.5 mM dNTP-mixed solution, one μl of the mixed solution of 5 unit/μl TAKARA LA Taq polymerase and 1.1 μg/μl TaqStart Antibody in a ratio of 1:1 by volume, 10 pmol of an oligonucleotide with the sequence of 5'-TCCGAAGCTTAAGATGGCTGCTGAACCAGTA-3' (SEQ ID NO:32) as a sense primer, chemically synthesized based on the nucleotide sequence of the DNA fragment in Example 1-4, and 10 pmol of an oligonucleotide with the nucleotide sequence of 5'-GGAAATAATTTTGTTCTCACAGGAGAGAGTTG-3' (SEQ ID NO:33) as an anti-sense primer, chemically synthesized based on the nucleotide sequence of the DNA fragment in Example 1-5, were mixed and volumed up to 50 μl with sterilized distilled water. After incubating at 94° C. for one min, the mixture was subjected to 5 cycles of incubations at 98° C. for 20 sec and at 72° C. for 7 min, followed by 25 cycles of incubations at 98° C. for 20 sec and 68° C. for 7 min to perform PCR. The reaction mixture was cleaved by restriction enzymes HindIII and SphI to obtain a DNA fragment of about 5,900 bp, with cleavage sites by HindIII and SphI in its both termini.

PCR was performed in the same condition as above, but 0.02 ng of the DNA fragment in Example 1-5, 0.06 ng of the DNA fragment obtained in Example 1-6, an oligonucleotide with the nucleotide sequence of 5'-ATGTAGCGGCCGCGGCATGAAATTTTAATAGCTAGTC-3' (SEQ ID NO:34) as an anti-sense primer, chemically synthesized based on the nucleotide sequence of the DNA fragment in Example 1-6, and an oligonucleotide with the sequence of 5'-CCTGGAATCAGATTACTTTGGCAAGCTTGAATC-3' (SEQ ID NO:35) as a sense primer, chemically synthesized based on the DNA fragment in Example 1-6, were used. The reaction mixture was cleaved by restriction enzymes NotI and SphI to obtain a DNA fragment of about 5,600 bp, with cleavage sites by NotI and SphI in its both termini.

A plasmid vector "pRc/CMV", containing a cytomegalovirus promoter, commercialized by Invitrogen Corporation, San Diego, USA, was cleaved by restriction enzymes HindIII and NotI to obtain a vector fragment of about 5,500 bp. The vector fragment was mixed with the above two DNA fragments of about 5,900 bp and 5,600 bp, and reacted with T4 DNA ligase to insert the two DNA fragments into the plasmid vector. An *Escherichia coli* JM109 strain was transformed with the obtained recombinant DNA, and the transformant with the plasmid vector was selected by the colony hybridization method. The selected recombinant DNA was named as "pBGHuGF". As shown in FIG. 1, the present genomic DNA, with the nucleotide sequence of SEQ ID NO:13, was ligated in the downstream of the cleavage site by the restriction enzyme HindIII in the recombinant DNA.

EXAMPLE 3

Preparation of Transformant Using CHO Cell as Host

CHO-K1 cells ATCC CCL61 were inoculated into Ham's F12 medium (pH 7.2) containing 10 v/v % bovine fetal serum and proliferated by conventional manner. The proliferated cells were collected and washed with phosphate-buffered saline (hereinafter abbreviated as "PBS") followed by suspending in PBS to give a cell density of 1×10$^7$ cells/ml.

10 μg of the recombinant DNA pBGHuGF in Example 2 and 0.8 ml of the above cell suspension were placed in a cuvette and ice-chilled for 10 min. The cuvette was installed in "GENE PULSER", an electroporation device commercialized by Bio-Rad Laboratories Inc., Brussels, Belgium, and then pulsed once with an electric discharge. After pulsing, the cuvette was immediately took out and ice-chilled for 10 min. The cell suspension from the cuvette was inoculated into Ham's F12 medium (pH 7.2) containing 10 v/v % bovine fetal serum and cultured under an ambient condition of 5 v/v % $CO_2$ at 37° C. for 3 days. To the culture medium was added G-418 to give a final concentration of 400 μg/ml, and the culturing was continued A further 3 weeks under the same conditions. From about 100 colonies formed, 48 colonies were selected, and a portion of each was inoculated into a well of culturing plates with Ham's F12 medium (pH7.2) containing 400 μg/ml G-418 and 10 v/v % bovine fetal serum and cultured similarly as above. Thereafter, to each well of the culturing plates was added 10 mM Tris-HCl buffer (pH 8.5) containing 5.1 mM magnesium chloride, 0.5 w/v % sodium deoxycholate, 1 w/v % NONIDET P-40, 10 μg/ml aprotinin and 0.1 w/v % SDS to lyse the cells.

50 μl aliquot of the cell lysates was mixed with one ml of glycerol and incubated at 37° C. for one hour, before the polypeptides in the cell lysates were separated by the SDS-polyacrylamide gel electrophoresis. The separated polypeptides were transferred to a nitrocellulose membrane in usual manner, and the membrane was soaked in the culture supernatant of the hybridoma H-1, disclosed in Japanese Patent Kokai No.231,598/96 by the same applicant of this invention, followed by washing with 50 mM Tris-HCl buffer containing 0.05 v/v % TWEEN 20 to remove an excessive mount of the monoclonal antibody. Thereafter, the nitrocellulose membrane was soaked in PBS containing rabbit-derived anti-mouse immunoglobulin antibody for one hr, which was labeled with horseradish peroxidase, followed by washing 50 mM Tris-HCl buffer (pH 7.5) containing 0.05 v/v % TWEEN 20 and soaking in 50 mM Tris-HCl buffer (pH 7.5) containing 0.005 v/v % hydrogen peroxide and 0.3 mg/ml diaminobenzidine to develop colorations. The clone, which highly produced the polypeptide, was selected based on the color development and named "BGHuGF".

EXAMPLE 4

Production of Polypeptide by Transformant and its Physicochemical Properties

The transformant BGHuGF in Experiment 3 was inoculated into Ham's F12 medium (pH 7.2) containing 400 μg/ml G-418 and 10 v/v % bovine fetal serum, and cultured under an ambient condition of 5 v/v % $CO_2$ at 37° C. for one week. The proliferated cells were collected, washed with PBS, and then washing with 10-fold volumes of ice-chilled 20 mM Hepes buffer (pH 7.4), containing 10 mM potassium chloride and 0.1 mM ethylendiaminetetraacetate bisodium salt, according to the method described in "Proceedings of The National Academy of The Sciences of The USA", vol.86, pp.5,227–5,231 (1989), by M. J. Kostura et al. The cells thus obtained were allowed to stand in 3-fold volumes of a fresh preparation of the same buffer under an ice-chilling condition for 20 min and freezed at –80° C., succeeded by thawing to disrupt the cells. The resulting cells were centrifuged to collect the supernatant.

In parallel, THP-1 cells ATCC TIB 202, derived from a human acute monocytic leukemia, was similarly cultured and disrupted. Supernatant, obtained by centrifuging the resulting cells, was mixed with the supernatant obtained from the transformant BGHuGF and incubated at 37° C. for 3 hr to react. The reaction mixture was applied to a column with "DEAE-SEPHAROSE", a gel for ion-exchange chromatography, commercialized by Pharmacia LKB Biotechnology AB, Upsalla, Sweden, equilibrated with 10 mM phosphate buffer (pH 6.6) before use. After washing the column with 10 mM phosphate buffer (pH 6.6), 10 mM phosphate buffer (pH 6.6) with a stepwise gradient of NaCl increasing from 0 M to 0.5 M was fed to the column, and fractions eluted by about 0.2 M NaCl were collected. The fractions were dialyzed against 10 mM phosphate buffer (pH 6.8) before applied to a column with "DEAE 5PW", a gel for ion-exchange chromatography, commercialized by TOSOH Corporation, Tokyo, Japan. To the column was fed 10 mM phosphate buffer (pH 6.8) with a linear gradient of NaCl increasing from 0 M to 0.5 M, and fractions eluted by about 0.2–0.3 M NaCl were collected.

While the obtained fractions were pooled and dialyzed against PBS, a gel for immunoaffinity chromatography with the monoclonal antibody were prepared according to the method disclosed in Japanese Patent Kokai No.231,598/96 by the same applicant of this invention. After the gel were charged into a plastic column and washed with PBS, the above dialyzed solution was applied to the column. To the column was fed 100 mM glycine-HCl buffer (pH 2.5), and the eluted fractions, which contained a polypeptide capable of inducing the production of IFN-γ by immunocompetent cells, were collected. After the collected fractions were dialyzed against sterilized distilled water and concentrated with a membrane filtration, the resultant was lyophilized to obtain a purified solid polypeptide in a yield of about 15 mg/l-culture.

Example for Reference

Expression in *Escherichia coli*

As disclosed in Japanese Patent Kokai No.193,098/96, a transformant pKHuGF which was obtained by introducing a cDNA with the nucleotide sequence of SEQ ID NO:2 into *Escherichia coli* as a host, was inoculated into L-broth medium containing 50 μg/ml ampicillin and cultured at 37° C. for 18 hr under shaking conditions. The cells were collected by centrifuging the resulting culture, and then suspended in a mixture solution (pH 7.2) of 139 mM NaCl, 7 mM $NaH_2PO_4$ and 3 mM $Na_2HPO_4$, followed by supersonicating to disrupt the cells. After the cell disruptants were centrifuged, the supernatant was subjected to purifying steps similarly as in Example 4-1 to obtain a purified solid polypeptide in a yield of about 5 mg/l-culture.

Comparing the yields of the polypeptides in Example for Reference and in Example 4-1 shows that the use of a transformant, which is formed by introducing a genomic DNA encoding the present polypeptide into a mammalian cell as a host, strongly elevates the yield of the polypeptide per culture.

EXAMPLE 4-2

Physicochemical Property of Polypeptide

EXAMPLE 4-2(a)

Biological Activity

Blood were collected from a healthy donor by using a syringe containing heparin, and then diluted with 2-fold volume of serum-free RPMI-1640 medium (pH 7.4). The blood was overlaid on ficoll, commercialized by Pharmacia LKB Biotechnology AB, Upsalla, Sweden, and centrifuged to obtain lymphocytes, which were then washed with RPMI-1640 medium containing 10 v/v % bovine fetal serum before being suspended in a fresh preparation of the same medium to give a cell density of $5 \times 10^6$ cells/ml. 0.15 ml aliquots of the cell suspension was distributed into wells of micro plates with 96 wells.

To the wells with the cells were distributed 0.05 ml aliquots of solutions of the polypeptide in Example 4-1, diluted with RPMI-1640 medium (pH 7.4) containing 10 v/v % bovine fetal serum to give desired concentrations. 0.05 ml aliquots of fresh preparations of the same medium with 2.5 μg/ml concanavalin A were further added to the wells, before culturing in a 5 V/V % $CO_2$ incubator at 37° C. for 24 hr. After the cultivation, 0.1 ml of the culture supernatant was collected from each well and examined on IFN-γ by usual enzyme immunoassay. In parallel, a systems as a control using the polypeptide in Reference for that in Example 4-1 or using no polypeptide was treated similarly as above. The results were in Table 1. IFN-γ in Table 1 were expressed with international units (IU), calculated based on the IFN-γ standard, Gg23-901-530, obtained from the International Institute of Health, USA.

TABLE 1

| Sample of polypeptide | IFN-γ production (IU/ml) |
| --- | --- |
| Example 4-2(a) | $3.4 \times 10^5$ |
| Example for Reference | $1.7 \times 10^5$ |

Table 1 indicates that the lymphocytes as immunocompetent cells produce IFN-γ by the action of the present polypeptide.

It is more remarkable that the polypeptide in Example 4-1 could induce IFN-γ production more than that in Example for Reference. Considering this and the difference in the yields of the polypeptides, described in Example for Reference, it can be presumed: Even if DNAs could be substantially equivalent in encoding the same amino acid sequence, not only the expressing efficiencies of the DNAS may differ, but the products expressed by them may significantly differ in their biological activities as a result of post-translational modifications by intracellular enzymes, depending on types of the DNAs and their hosts; (a) one type is used a transformant formed by introducing a DNA, which is a cDNA, into a microorganisms as a host, and (b) other type is used a transformant formed by introducing the present genomic DNA into a mammalian cell as a host.

EXAMPLE 4-2(b)

Molecular Weight

SDS-polyacrylamide gel electrophoresis of the polypeptide in Example 4-1 in the presence of 2 w/v % dithiothreitol as a reducing agent, according to the method reported by U. K. Laemli et al., in "Nature", Vol.227, pp.680–685 (1970), exhibited a main band of a protein capable of inducing IFN-γ in a position corresponding to a molecular weight of about 18,000–19,500 daltons. The molecular weight makers used in the analysis were bovine serum albumin (67,000 daltons), ovalbumin (45,000 daltons), carbonic anhydrase (30,000 daltons), soy bean trypsin inhibitor (20,100 daltons) and α-lactoalbumin (14,000 daltons).

EXAMPLE 4-2(c)

N-Terminal Amino Acid Sequence

Conventional analysis using "MODEL 473A", a protein sequencer commercialized by Perkin-Elmer Corp., Norwalk, USA, revealed that the polypeptide in Example 4-1 had the amino acid sequence of SEQ ID NO:15 in the N-terminal region.

Judging collectively from this result as well as the information that SDS-polyacrylamide gel electrophresis exhibited a main band in a position corresponding to a molecular weight of about 18,000–19,500 daltons, and that the molecular weight calculated from the amino acid sequence of SEQ ID NO:1 was 18,199 daltons, it can be concluded that the polypeptide in Example 4-1 has the amino acid sequence of SEQ ID NO:6.

As is described above, the present invention is made based on the identification of a genomic DNA encoding the polypeptide which induces the production of IFN-γ by immunocompetent cells. The present genomic DNA efficiently express the present polypeptide when introduced into mammalian host cells. The polypeptide features higher biological activities than that obtained by the cDNA expression in *Escherichia coli*. Therefore, the present genomic DNA is useful for the recombinant DNA techniques to prepare the polypeptide capable of inducing IFN-γ production by immunocompetent cells. The present genomic DNA is useful to gene therapy for diseases including viral diseases, bacterial-infectious diseases, malignant tumors and immunopathies.

Thus, the present invention is a significant invention which has a remarkable effect and gives a great contribution to this field.

While there has been described what is at present considered to be the preferred embodiments of the present invention, it will be understood the various modifications may be made therein, and it is intended to cover in the appended claims all such modifications as fall within the true spirits and scope of the invention.

What is claimed is:

1. A method for treating IFN-γ and/or killer cell-susceptive tumors using gene therapy, comprising:

transforming tumor cells obtained from a subject in need thereof with a composition comprising an isolated DNA molecule that comprises a nucleotide sequence encoding the amino acid sequence of SEQ ID NO:1, where Xaa is isoleucine or threonine, and a carrier capable of introducing the isolated DNA molecule into a mammalian cell, wherein said nucleotide sequence consists of the sequence of a fragment of human genomic DNA;

proliferating the transformed tumor cells ex vivo; and transplanting the proliferated transformed tumor cells into a tumor in the subject to treat the non-transformed tumor cells in the subject.

2. A method for treating IFN-γ and/or killer cell-susceptive tumors using gene therapy, comprising:

transforming tumor cells obtained from a subject in need thereof with an isolated DNA molecule comprising a nucleotide sequence encoding the amino acid sequence of SEQ ID NO:1, where Xaa is isoleucine or threonine, wherein said nucleotide sequence consists of the sequence of a fragment of human genomic DNA;

proliferating the transformed tumor cells ex vivo; and transplanting the proliferated transformed tumor cells into a tumor in the subject to treat the non-transformed tumor cells in the subject.

3. The method according to claim 1, wherein the carrier is a virus or liposome.

4. The method according to claim 1, wherein the isolated DNA molecule is linked with a heterologous nucleotide sequence.

5. The method according to claim 4, wherein the heterologous nucleotide sequence is a virus vector.

* * * * *

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
       (A) LENGTH: 157 amino acids
       (B) TYPE: amino acid
       (D) TOPOLOGY: linear (ii) MOLECULE TYPE: peptide (xi) SEQUENCE DESCRIPTION: SEQ ID NO: 1:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
    50                  55                  60

Ser Val Lys Cys Glu Lys Ile Ser Xaa Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO: 2:

(i) SEQUENCE CHARACTERISTICS:
       (A) LENGTH: 1120 base pairs
       (B) TYPE: nucleic acid
       (C) STRANDEDNESS: double
       (D) TOPOLOGY: linear (ii) MOLECULE TYPE: cDNA to mRNA (iii) HYPOTHETICAL: No (iv) ANTI-SENSE: No (vi) ORIGINAL SOURCE:
       (A) ORGANISM: human
       (F) TISSUE TYPE: liver (iX) FEATURE:
       (A) NAME/KEY: 5'UTR

```
        (B) LOCATION: 1..177
        (C) IDENTIFICATION METHOD: E
        (A) NAME/KEY: leader peptide
        (B) LOCATION: 178..285
        (C) IDENTIFICATION METHOD: S
        (A) NAME/KEY: mat peptide
        (B) LOCATION: 286..756
        (C) IDENTIFICATION METHOD: S
        (A) NAME/KEY: 3'UTR
        (B) LOCATION: 757..1120
        (C) IDENTIFICATION METHOD: E (xi) SEQUENCE DESCRIPTION: SEQ ID NO:2:

GCCTGGACAG TCAGCAAGGA ATTGTCTCCC AGTGCATTTT GCCCTCCTGG CTGCCAACTC      60

TGGCTGCTAA AGCGGCTGCC ACCTGCTGCA GTCTACACAG CTTCGGGAAG AGGAAAGGAA     120

CCTCAGACCT TCCAGATCGC TTCCTCTCGC AACAAACTAT TTGTCGCAGG AATAAAG       177

ATG GCT GCT GAA CCA GTA GAA GAC AAT TGC ATC AAC TTT GTG GCA ATG      225
Met Ala Ala Glu Pro Val Glu Asp Asn Cys Ile Asn Phe Val Ala Met
    -35             -30                 -25

AAA TTT ATT GAC AAT ACG CTT TAC TTT ATA GCT GAA GAT GAT GAA AAC      273
Lys Phe Ile Asp Asn Thr Leu Tyr Phe Ile Ala Glu Asp Asp Glu Asn
-20             -15                 -10                 -5

CTG GAA TCA GAT TAC TTT GGC AAG CTT GAA TCT AAA TTA TCA GTC ATA      321
Leu Glu Ser Asp Tyr Phe Gly Lys Leu Glu Ser Lys Leu Ser Val Ile
                1               5                   10

AGA AAT TTG AAT GAC CAA GTT CTC TTC ATT GAC CAA GGA AAT CGG CCT      369
Arg Asn Leu Asn Asp Gln Val Leu Phe Ile Asp Gln Gly Asn Arg Pro
            15                  20                  25

CTA TTT GAA GAT ATG ACT GAT TCT GAC TGT AGA GAT AAT GCA CCC CGG      417
Leu Phe Glu Asp Met Thr Asp Ser Asp Cys Arg Asp Asn Ala Pro Arg
30                  35                  40

ACC ATA TTT ATT ATA AGT ATG TAT AAA GAT AGC CAG CCT AGA GGT ATG      465
Thr Ile Phe Ile Ile Ser Met Tyr Lys Asp Ser Gln Pro Arg Gly Met
45                  50                  55                  60

GCT GTA ACT ATC TCT GTG AAG TGT GAG AAA ATT TCA AYT CTC TCC TGT      513
Ala Val Thr Ile Ser Val Lys Cys Glu Lys Ile Ser Xaa Leu Ser Cys
                65                  70                  75

GAG AAC AAA ATT ATT TCC TTT AAG GAA ATG AAT CCT CCT GAT AAC ATC      561
Glu Asn Lys Ile Ile Ser Phe Lys Glu Met Asn Pro Pro Asp Asn Ile
            80                  85                  90

AAG GAT ACA AAA AGT GAC ATC ATA TTC TTT CAG AGA AGT GTC CCA GGA      609
Lys Asp Thr Lys Ser Asp Ile Ile Phe Phe Gln Arg Ser Val Pro Gly
        95                  100                 105

CAT GAT AAT AAG ATG CAA TTT GAA TCT TCA TCA TAC GAA GGA TAC TTT      657
His Asp Asn Lys Met Gln Phe Glu Ser Ser Ser Tyr Glu Gly Tyr Phe
    110                 115                 120

CTA GCT TGT GAA AAA GAG AGA GAC CTT TTT AAA CTC ATT TTG AAA AAA      705
Leu Ala Cys Glu Lys Glu Arg Asp Leu Phe Lys Leu Ile Leu Lys Lys
125                 130                 135                 140

GAG GAT GAA TTG GGG GAT AGA TCT ATA ATG TTC ACT GTT CAA AAC GAA      753
Glu Asp Glu Leu Gly Asp Arg Ser Ile Met Phe Thr Val Gln Asn Glu
                145                 150                 155

GAC TAGCTATTAA AATTTCATGC CGGGCGCAGT GGCTCACGCC TGTAATCCCA           806
Asp

GCCCTTTGGG AGGCTGAGGC GGGCAGATCA CCAGAGGTCA GGTGTTCAAG ACCAGCCTGA     866

CCAACATGGT GAAACCTCAT CTCTACTAAA AATACTAAAA ATTAGCTGAG TGTAGTGACG     926

CATGCCCTCA ATCCCAGCTA CTCAAGAGGC TGAGGCAGGA GAATCACTTG CACTCCGGAG     986

GTAGAGGTTG TGGTGAGCCG AGATTGCACC ATTGCGCTCT AGCCTGGGCA ACAACAGCAA    1046
```

```
AACTCCATCT CAAAAAATAA AATAAATAAA TAAACAAATA AAAAATTCAT AATGTGAAAA      1106

AAAAAAAAAA AAAA                                                        1120
```

(2) INFORMATION FOR SEQ ID NO: 3:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: exon
        (B) LOCATION: 1..135
        (C) IDENTIFICATION METHOD: S (xi) SEQUENCE DESCRIPTION: SEQ ID NO: 3:

```
 AA AAC CTG GAA TCA GAT TAC TTT GGC AAG CTT GAA TCT AAA TTA TCA        47
    Glu Asn Leu Glu Ser Asp Tyr Phe Gly Lys Leu Glu Ser Lys Leu Ser
    -5              1               5                  10

GTC ATA AGA AAT TTG AAT GAC CAA GTT CTC TTC ATT GAC CAA GGA AAT        95
Val Ile Arg Asn Leu Asn Asp Gln Val Leu Phe Ile Asp Gln Gly Asn
            15                  20                  25

CGG CCT CTA TTT GAA GAT ATG ACT GAT TCT GAC TGT AGA G                 135
Arg Pro Leu Phe Glu Asp Met Thr Asp Ser Asp Cys Arg Asp
        30                  35                  40
```

(2) INFORMATION FOR SEQ ID NO: 4:

(i) SEQUENCE CHARACTERISTICS:
        (A) LENGTH: 134 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: exon
        (B) LOCATION: 1..134
        (C) IDENTIFICATION METHOD: S (xi) SEQUENCE DESCRIPTION: SEQ ID NO: 4:

```
AT AAT GCA CCC CGG ACC ATA TTT ATT ATA AGT ATG TAT AAA GAT AGC         47
Asp Asn Ala Pro Arg Thr Ile Phe Ile Ile Ser Met Tyr Lys Asp Ser
40              45                  50                  55

CAG CCT AGA GGT ATG GCT GTA ACT ATC TCT GTG AAG TGT GAG AAA ATT        95
Gln Pro Arg Gly Met Ala Val Thr Ile Ser Val Lys Cys Glu Lys Ile
            60                  65                  70

TCA ACT CTC TCC TGT GAG AAC AAA ATT ATT TCC TTT AAG                   134
Ser Thr Leu Ser Cys Glu Asn Lys Ile Ile Ser Phe Lys
        80                  85
```

(2) INFORMATION FOR SEQ ID NO: 5:

(i) SEQUENCE CHARACTERISTICS:
        (A) LENGTH: 87 base pairs
        (B) TYPE: nucleic acid
        (C) STRANDEDNESS: double (D) TOPOLOGY: linear (ii) MOLECULE TYPE: Genomic DNA (vi) ORIGINAL SOURCE:
             (A) ORGANISM: human
             (F) TISSUE TYPE: placenta (ix) FEATURE:
             (A) NAME/KEY: exon
             (B) LOCATION: 1..87
             (C) IDENTIFICATION METHOD: S (xi) SEQUENCE DESCRIPTION: SEQ ID NO: 5:

```
GAATAAAG ATG GCT GCT GAA CCA GTA GAA GAC AAT TGC ATC AAC TTT GTG         50
         Met Ala Ala Glu Pro Val Glu Asp Asn Cys Ile Asn Phe Val
             -35             -30             -25

GCA ATG AAA TTT ATT GAC AAT ACG CTT TAC TTT ATA G                        87
Ala Met Lys Phe Ile Asp Asn Thr Leu Tyr Phe Ile Ala
        -20             -15             -10
```

(2) INFORMATION FOR SEQ ID NO:6:

(i) SEQUENCE CHARACTERISTICS:
             (A) LENGTH: 12 base pairs
             (B) TYPE: nucleic acid
             (C) STRANDEDNESS: double
             (D) TOPOLOGY: linear (ii) MOLECULE TYPE: Genomic DNA (vi) ORIGINAL SOURCE:
             (A) ORGANISM: human
             (F) TISSUE TYPE: placenta (ix) FEATURE:
             (A) NAME/KEY: exon
             (B) LOCATION: 1..87
             (C) IDENTIFICATION METHOD: S (xi) SEQUENCE DESCRIPTION: SEQ ID NO: 6:

```
CT GAA GAT GAT G                                                         12
Ala Glu Asp Asp Glu
-10
```

(2) INFORMATION FOR SEQ ID NO: 7:

(i) SEQUENCE CHARACTERISTICS:
             (A) LENGTH: 2167 base pairs
             (B) TYPE: nucleic acid
             (C) STRANDEDNESS: double
             (D) TOPOLOGY: linear (ii) MOLECULE TYPE: Genomic DNA (vi) ORIGINAL SOURCE:
             (A) ORGANISM: human
             (F) TISSUE TYPE: placenta (ix) FEATURE:
             (A) NAME/KEY: exon + 3'UTR
             (B) LOCATION: 1..2167
             (C) IDENTIFICATION METHOD: E (xi) SEQUENCE DESCRIPTION: SEQ ID NO: 7:

```
GAA ATG AAT CCT CCT GAT AAC ATC AAG GAT ACA AAA AGT GAC ATC ATA          48
Glu Met Asn Pro Pro Asp Asn Ile Lys Asp Thr Lys Ser Asp Ile Ile
85              90              95              100

TTC TTT CAG AGA AGT GTC CCA GGA CAT GAT AAT AAG ATG CAA TTT GAA          96
Phe Phe Gln Arg Ser Val Pro Gly His Asp Asn Lys Met Gln Phe Glu
        105             110             115
```

```
TCT TCA TCA TAC GAA GGA TAC TTT CTA GCT TGT GAA AAA GAG AGA GAC      144
Ser Ser Ser Tyr Glu Gly Tyr Phe Leu Ala Cys Glu Lys Glu Arg Asp
            120                 125                 130

CTT TTT AAA CTC ATT TTG AAA AAA GAG GAT GAA TTG GGG GAT AGA TCT      192
Leu Phe Lys Leu Ile Leu Lys Lys Glu Asp Glu Leu Gly Asp Arg Ser
            135                 140                 145

ATA ATG TTC ACT GTT CAA AAC GAA GAC TAGCTAT TAAAATTTCA TGCCGGGCGC    246
Ile Met Phe Thr Val Gln Asn Glu Asp
    150                 155

AGTGGCTCAC GCCTGTAATC CCAGCCCTTT GGGAGGCTGA GGCGGGCAGA TCACCAGAGG    306

TCAGGTGTTC AAGACCAGCC TGACCAACAT GGTGAAACCT CATCTCTACT AAAAATACAA    366

AAAATTAGCT GAGTGTAGTG ACCCATGCCC TCAATCCCAG CTACTCAAGA GGCTGAGGCA    426

GGAGAATCAC TTGCACTCCG GAGGTGGAGG TTGTGGTGAG CCGAGATTGC ACCATTGCGC    486

TCTAGCCTGG GCAACAACAG CAAAACTCCA TCTCAAAAAA TAAAATAAAT AAATAAACAA    546

ATAAAAAATT CATAATGTGA ACTGTCTGAA TTTTTATGTT TAGAAAGATT ATGAGATTAT    606

TAGTCTATAA TTGTAATGGT GAAATAAAAT AAATACCAGT CTTGAAAAAC ATCATTAAGA    666

AATGAATGAA CTTTCACAAA AGCAAACAAA CAGACTTTCC CTTATTTAAG TGAATAAAAT    726

AAAATAAAAT AAAATAATGT TTAAAAAATT CATAGTTTGA AAACATTCTA CATTGTTAAT    786

TGGCATATTA ATTATACTTA ATATAATTAT TTTTAAATCT TTTGGGTTAT TAGTCCTAAT    846

GACAAAAGAT ATTGATATTT GAACTTTCTA ATTTTTAAGA ATATCGTTAA ACCATCAATA    906

TTTTTATAAG GAGGCCACTT CACTTGACAA ATTTCTGAAT TCCTCCAAA GTCAGTATAT     966

TTTTAAAATT CAGTTTGATC CTGAATCCAG CAATATATAA AAGGGATTAT ATACTCTGGC   1026

CAACTGACAT TCATCCTAGG AATGCAAAGA TGGTTTAATA TCCTAAAATC AATTAACATA   1086

ACATACTATA TTAATAAAGT ATCAAAACAG TATTCTCATC TTTTTTTCTT TTTTCACAAT   1146

TCCTTGGTTA CACTATCATC TCAATAGATG CAGAAAAAGC ATTTGACAAA ATCCAATTCA   1206

TAATAAAAAT TCTCAAACTT GAAAGAGAAC ATCATAAAGG CATCTATGAA AAACCTACAG   1266

CTAATATCAT ACTTAACGAT GAAAAACTGA ATTATTTTAC CCTAAGATCA AGAATAATGC   1326

AAGCATGTCA GCTCTTGCAA CTTCTATTCA ACATTGTACT GGAGGTTCTA GCCAGAGCAA   1386

CCATACAATA AATAAAAATA AAAGGCACCC AGATTAGAAA GGAAGTCTTT ATTTGCAGAC   1446

AACATGGTTC TTTATGCAGA AAACCGTCAG GAATACACAC ACATGTTAGA ACTAATAAGT   1506

TCAGCAAGGT TGCAGGTTGC AATATCAATA TGCAAAATA CATTGAAGGC TGGGCTCAGT    1566

GGAGATGGCA TGTACCTTTC GTCCCAGCTA CTTGGGAGGC TGAGGTAGGA GGATCACTTG   1626

AGGTGAGGAG TTTGAGGCTA TAGTGCAATG TGATCTTGCC TGTGAATAGC CACTGCACTC   1686

GAGCCTAGGC AACAAAGTGA GACCCCGTCT CCAAAAAAAA AAATGGTATA TTGGTATTTC   1746

TGTATATGAA CAATGAATGA TCTGAAAACA AGAAAATTCC ATTCACGATG GTATTAAAAA   1806

AATAAAATAC AAATAAATTT AGCAAAATAA TTATAAAACT TGTACATCGA AAATTTCAAA   1866

GCACTCTGAG GGAAATTAAA GATGATCTAA ATAATTGGAG AGACACTCTA TGATCACTGA   1926

TTGGAAAATT CATTCAATAT TGTTAAGATA ACAATTGTCC CCAAATTGAT GCATGCATTC   1986

AATTTAGTCT TCATCAAAAT TCCAGCAGGG TTTTTGCAGA AATTGACAAG CTGTACCCAA   2046

AATGTATATG GAAATGAAAA GACCCAGAAG AGCAAATAAT TTTTTAAAAA CAAAGTTGGA   2106

AAACTTTTAC TTCCTAATTT TAAAACTTAC TATAAACCTA AAGTTATCAA GACCATTTAG   2166
T                                                                   2167
```

(2) INFORMATION FOR SEQ ID NO: 8:

(i) SEQUENCE CHARACTERISTICS:
        (A) LENGTH: 1334 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: intron
        (B) LOCATION: 1..1334
        (C) IDENTIFICATION METHOD: E (xi) SEQUENCE DESCRIPTION: SEQ ID NO: 8:

```
GTATTTTTTT TAATTCGCAA ACATAGAAAT GACTAGCTAC TTCTTCCCAT TCTGTTTTAC        60
TGCTTACATT GTTCCGTGCT AGTCCCAATC CTCAGATGAA AAGTCACAGG AGTGACAATA       120
ATTTCACTTA CAGGAAACTT TATAAGGCAT CCACGTTTTT TAGTTGGGGT AAAAAATTGG       180
ATACAATAAG ACATTGCTAG GGGTCATGCC TCTCTGAGCC TGCCTTTGAA TCACCAATCC       240
CTTTATTGTG ATTGCATTAA CTGTTTAAAA CCTCTATAGT TGGATGCTTA ATCCCTGCTT       300
GTTACAGCTG AAAATGCTGA TAGTTTACCA GGTGTGGTGG CATCTATCTG TAATCCTAGC       360
TACTTGGGAG GCTCAAGCAG GAGGATTGCT TGAGGCCAGG ACTTTGAGGC TGTAGTACAC       420
TGTGATCGTA CCTGTGAATA GCCACTGCAC TCCAGCCTGG GTGATATACA GACCTTGTCT       480
CTAAAATTAA AAAAAAAAAA AAAAAAACC TTAGGAAAGG AAATTGATCA AGTCTACTGT        540
GCCTTCCAAA ACATGAATTC CAAATATCAA AGTTAGGCTG AGTTGAAGCA GTGAATGTGC       600
ATTCTTTAAA AATACTGAAT ACTTACCTTA ACATATATTT TAAATATTTT ATTTAGCATT       660
TAAAAGTTAA AAACAATCTT TTAGAATTCA TATCTTTAAA ATACTCAAAA AAGTTGCAGC       720
GTGTGTGTTG TAATACACAT TAAACTGTGG GGTTGTTTGT TTGTTTGAGA TGCAGTTTCA       780
CTCTGTCACC CAGGCTGAAG TGCAGTGCAG TGCAGTGGTG TGATCTCGGC TCACTACAAC       840
CTCCACCTCC CACGTTCAAG CGATTCTCAT GCCTCAGTCT CCCGAGTAGG TGGGATTACA       900
GGCATGCACC ACTTACACCC GGCTAATTTT TGTATTTTTA GTAGAGCTGG GGTTTCACCA       960
TGTTGGCCAG GCTGGTCTCA AACCCCTAAC CTCAAGTGAT CTGCCTGCCT CAGCCTCCCA      1020
AACAAACAAA CAACCCCACA GTTTAATATG TGTTACAACA CACATGCTGC AACTTTTATG      1080
AGTATTTTAA TGATATAGAT TATAAAAGGT TGTTTTTAAC TTTTAAATGC TGGGATTACA      1140
GGCATGAGCC ACTGTGCCAG GCCTGAACTG TGTTTTTAAA AATGTCTGAC CAGCTGTACA      1200
TAGTCTCCTG CAGACTGGCC AAGTCTCAAA GTGGGAACAG GTGTATTAAG GACTATCCTT      1260
TGGTTAAATT TCCGCAAATG TTCCTGTGCA AGAATTCTTC TAACTAGAGT TCTCATTTAT      1320
TATATTTATT TCAG                                                       1334
```

(2) INFORMATION FOR SEQ ID NO: 9:

(i) SEQUENCE CHARACTERISTICS:
        (A) LENGTH: 4773 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:

(A) ORGANIZM: human
        (F) TISSUE TYPE: placenta (ix) FEATURE:
        (A) NAME/KEY: intron
        (B) LOCATION: 1..4773
        (C) IDENTIFICATION METHOD: E (xi) SEQUENCE DESCRIPTION: SEQ ID NO: 9:

```
GTAAGACTGA GCCTTACTTT GTTTTCAATC ATGTTAATAT AATCAATATA ATTAGAAATA      60

TAACATTATT TCTAATGTTA ATATAAGTAA TGTAATTAGA AAACTCAAAT ATCCTCAGAC     120

CAACCTTTTG TCTAGAACAG AAATAACAAG AAGCAGAGAA CCATTAAAGT GAATACTTAC     180

TAAAAATTAT CAAACTCTTT ACCTATTGTG ATAATGATGG TTTTTCTGAG CCTGTCACAG     240

GGGAAGAGGA GATACAACAC TTGTTTTATG ACCTGCATCT CCTGAACAAT CAGTCTTTAT     300

ACAAATAATA ATGTAGAATA CATATGTGAG TTATACATTT AAGAATAACA TGTGACTTTC     360

CAGAATGAGT TCTGCTATGA AGAATGAAGC TAATTATCCT TCTATATTTC TACACCTTTG     420

TAAATTATGA TAATATTTTA ATCCCTAGTT GTTTTGTTGC TGATCCTTAG CCTAAGTCTT     480

AGACACAAGC TTCAGCTTCC AGTTGATGTA TGTTATTTTT AATGTTAATC TAATTGAATA     540

AAAGTTATGA GATCAGCTGT AAAAGTAATG CTATAATTAT CTTCAAGCCA GGTATAAAGT     600

ATTTCTGGCC TCTACTTTTT CTCTATTATT CTCCATTATT ATTCTCTATT ATTTTTCTCT     660

ATTTCCTCCA TTATTGTTAG ATAAACCACA ATTAACTATA GCTACAGACT GAGCCAGTAA     720

GAGTAGCCAG GGATGCTTAC AAATTGGCAA TGCTTCAGAG GAGAATTCCA TGTCATGAAG     780

ACTCTTTTTG AGTGGAGATT TGCCAATAAA TATCCGCTTT CATGCCCACC CAGTCCCCAC     840

TGAAAGACAG TTAGGATATG ACCTTAGTGA AGGTACCAAG GGGCAACTTG GTAGGGAGAA     900

AAAAGCCACT CTAAAATATA ATCCAAGTAA GAACAGTGCA TATGCAACAG ATACAGCCCC     960

CAGACAAATC CCTCAGCTAT CTCCCTCCAA CCAGAGTGCC ACCCCTTCAG GTGACAATTT    1020

GGAGTCCCCA TTCTAGACCT GACAGGCAGC TTAGTTATCA AAATAGCATA AGAGGCCTGG    1080

GATGGAAGGG TAGGGTGGAA AGGGTTAAGC ATGCTGTTAC TGAACAACAT AATTAGAAGG    1140

GAAGGAGATG GCCAAGCTCA AGCTATGTGG GATAGAGGAA AACTCAGCTG CAGAGGCAGA    1200

TTCAGAAACT GGGATAAGTC CGAACCTACA GGTGGATTCT TGTTGAGGGA GACTGGTGAA    1260

AATGTTAAGA AGATGGAAAT AATGCTTGGC ACTTAGTAGG AACTGGGCAA ATCCATATTT    1320

GGGGGAGCCT GAAGTTTATT CAATTTTGAT GGCCCTTTTA AATAAAAAGA ATGTGGCTGG    1380

GCGTGGTGGC TCACACCTGT AATCCCAGCA CTTTGGGAGG CCGAGGGGGG CGGATCACCT    1440

GAAGTCAGGA GTTCAAGACC AGCCTGACCA ACATGGAGAA ACCCCATCTC TACTAAAAAT    1500

ACAAAATTAG CTGGGCGTGG TGGCATATGC CTGTAATCCC AGCTACTCGG GAGGCTGAGG    1560

CAGGAGAATC TTTTGAACCC GGGAGGCAGA GGTTGCGATG AGCCTAGATC GTGCCATTGC    1620

ACTCCAGCCT GGGCAACAAG AGCAAAACTC GGTCTCAAAA AAAAAAAAA AAAAGTGAAA    1680

TTAACCAAAG GCATTAGCTT AATAATTTAA TACTGTTTTT AAGTAGGGCG GGGGTGGCT    1740

GGAAGAGATC TGTGTAAATG AGGGAATCTG ACATTTAAGC TTCATCAGCA TCATAGCAAA    1800

TCTGCTTCTG GAAGGAACTC AATAAATATT AGTTGGAGGG GGGGAGAGAG TGAGGGGTGG    1860

ACTAGGACCA GTTTTAGCCC TTGTCTTTAA TCCCTTTTCC TGCCACTAAT AAGGATCTTA    1920

GCAGTGGTTA TAAAAGTGGC CTAGGTTCTA GATAATAAGA TACAACAGGC CAGGCACAGT    1980

GGCTCATGCC TATAATCCCA GCACTTTGGG AGGGCAAGGC GAGTGTCTCA CTTGAGATCA    2040

GGAGTTCAAG ACCAGCCTGG CCAGCATGGC GATACTCTGT CTCTACTAAA AAAATACAA    2100
```

```
AAATTAGCCA GGCATGGTGG CATGCACCTG TAATCCCAGC TACTCGTGAG CCTGAGGCAG    2160

AAGAATCGCT TGAAACCAGG AGGTGTAGGC TGCAGTGAGC TGAGATCGCA CCACTGCACT    2220

CCAGCCTGGG CGACAGAATG AGACTTTGTC TCAAAAAAAG AAAAAGATAC AACAGGCTAC    2280

CCTTATGTGC TCACCTTTCA CTGTTGATTA CTAGCTATAA AGTCCTATAA AGTTCTTTGG    2340

TCAAGAACCT TGACAACACT AAGAGGGATT TGCTTTGAGA GGTTACTGTC AGAGTCTGTT    2400

TCATATATAT ACATATACAT GTATATATGT ATCTATATCC AGGCTTGGCC AGGGTTCCCT    2460

CAGACTTTCC AGTGCACTTG GGAGATGTTA GGTCAATATC AACTTTCCCT GGATTCAGAT    2520

TCAACCCCTT CTGATGTAAA AAAAAAAAAA AAAAAGAAAG AAATCCCTTT CCCCTTGGAG    2580

CACTCAAGTT TCACCAGGTG GGGCTTTCCA AGTTGGGGGT TCTCCAAGGT CATTGGGATT    2640

GCTTTCACAT CCATTTGCTA TGTACCTTCC CTATGATGGC TGGGAGTGGT CAACATCAAA    2700

ACTAGGAAAG CTACTGCCCA AGGATGTCCT TACCTCTATT CTGAAATGTG CAATAAGTGT    2760

GATTAAAGAG ATTGCCTGTT CTACCTATCC ACACTCTCGC TTTCAACTGT AACTTTCTTT    2820

TTTTCTTTTT TTCTTTTTTT CTTTTTTTTT GAAACGGAGT CTCGCTCTGT CGCCCAGGCT    2880

AGAGTGCAGT GGCACGATCT CAGCTCACTG CAAGCTCTGC CTCCCGGGTT CACGCCATTC    2940

TCCTGCCTCA CCCTCCCAAG CAGCTGGGAC TACAGGCGCC TGCCACCATG CCCAGCTAAT    3000

TTTTTGTATT TTTAGTAGAG ACGGGGTTTC ACCGTGTTAG CCAGGATGGT CTCGATCTCC    3060

TGAACTTGTG ATCCGCCCGC CTCAGCCTCC CAAAGTGCTG GGATTACAGG CGTGAGCCAT    3120

CGCACCCGGC TCAACTGTAA CTTTCTATAC TGGTTCATCT TCCCCTGTAA TGTTACTAGA    3180

GCTTTTGAAG TTTTGGCTAT GGATTATTTC TCATTTATAC ATTAGATTTC AGATTAGTTC    3240

CAAATTGATG CCCACAGCTT AGGGTCTCTT CCTAAATTGT ATATTGTAGA CAGCTGCAGA    3300

AGTGGGTGCC AATAGGGGAA CTAGTTTATA CTTTCATCAA CTTAGGACCC ACACTTGTTG    3360

ATAAAGAACA AAGGTCAAGA GTTATGACTA CTGATTCCAC AACTGATTGA GAAGTTGGAG    3420

ATAACCCCGT GACCTCTGCC ATCCAGAGTC TTTCAGGCAT CTTTGAAGGA TGAAGAAATG    3480

CTATTTTAAT TTTGGAGGTT TCTCTATCAG TGCTTAGGAT CATGGGAATC TGTGCTGCCA    3540

TGAGGCCAAA ATTAAGTCCA AAACATCTAC TGGTTCCAGG ATTAACATGG AAGAACCTTA    3600

GGTGGTGCCC ACATGTTCTG ATCCATCCTG CAAAATAGAC ATGCTGCACT AACAGGAAAA    3660

GTGCAGGCAG CACTACCAGT TGGATAACCT GCAAGATTAT AGTTTCAAGT AATCTAACCA    3720

TTTCTCACAA GGCCCTATTC TGTGACTGAA ACATACAAGA ATCTGCATTT GGCCTTCTAA    3780

GGCAGGGCCC AGCCAAGGAG ACCATATTCA GGACAGAAAT TCAAGACTAC TATGGAACTG    3840

GAGTGCTTGG CAGGGAAGAC AGAGTCAAGG ACTGCCAACT GAGCCAATAC AGCAGGCTTA    3900

CACAGGAACC CAGGGCCTAG CCCTACAACA ATTATTGGGT CTATTCACTG TAAGTTTTAA    3960

TTTCAGGCTC CACTGAAAGA GTAAGCTAAG ATTCCTGGCA CTTTCTGTCT CTCTCACAGT    4020

TGGCTCAGAA ATGAGAACTG GTCAGGCCAG GCATGGTGGC TTACACCTGG AATCCCAGCA    4080

CTTTGGGAGG CCGAAGTGGG AGGGTCACTT GAGGCCAGGA GTTCAGGACC AGCTTAGGCA    4140

ACAAAGTGAG ATACCCCCTG ACCCCTTCTC TACAAAAATA AATTTTAAAA ATTAGCCAAA    4200

TGTGGTGGTG TATACTTACA GTCCCAGCTA CTCAGGAGGC TGAGGCAGGG GGATTGCTTG    4260

AGCCCAGGAA TTCAAGGCTG CAGTGAGCTA TGATTTCACC ACTGCACTTC TGGCTGGGCA    4320

ACAGAGCGAG ACCCTGTCTC AAAGCAAAAA GAAAAGAAA CTAGAACTAG CCTAAGTTTG    4380

TGGGAGGAGG TCATCATCGT CTTTAGCCGT GAATGGTTAT TATAGAGGAC AGAAATTGAC    4440
```

```
ATTAGCCCAA AAAGCTTGTG GTCTTTGCTG GAACTCTACT TAATCTTGAG CAAATGTGGA      4500

CACCACTCAA TGGGAGAGGA GAGAAGTAAG CTGTTTGATG TATAGGGGAA AACTAGAGGC      4560

CTGGAACTGA ATATGCATCC CATGACAGGG AGAATAGGAG ATTCGGAGTT AAGAAGGAGA      4620

GGAGGTCAGT ACTGCTGTTC AGAGATTTTT TTTATGTAAC TCTTGAGAAG CAAAACTACT      4680

TTTGTTCTGT TTGGTAATAT ACTTCAAAAC AAACTTCATA TATTCAAATT GTTCATGTCC      4740

TGAAATAATT AGGTAATGTT TTTTTCTCTA TAG                                   4773
```

(2) INFORMATION FOR SEQ ID NO: 10:

(i) SEQUENCE CHARACTERISTICS:
        (A) LENGTH: 8835 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: intron
        (B) LOCATION: 1..8835
        (C) IDENTIFICATION METHOD: E (xi) SEQUENCE DESCRIPTION: SEQ ID NO: 10:

```
GTAAGAAATA TCATTCCTCT TTATTTGGAA AGTCAGCCAT GGCAATTAGA GGTAAATAAG        60

CTAGAAAGCA ATTGAGAGGA ATATAAACCA TCTAGCATCA CTACGATGAG CAGTCAGTAT       120

CAACATAAGA AATATAAGCA AAGTCAGAGT AGAATTTTTT TCTTTTATCA GATATGGGAG       180

AGTATCACTT TAGAGGAGAG GTTCTCAAAC TTTTTGCTCT CATGTTCCCT TTACACTAAG       240

CACATCACAT GTTAGCATAA GTAACATTTT TAATTAAAAA TAACTATGTA CTTTTTTAAC       300

AACAAAAAAA AGCATAAAGA GTGACACTTT TTTATTTTTA CAAGTGTTTT AACTGGTTTA       360

ATAGAAGCCA TATAGATCTG CTGGATTCTC ATCTGCTTTG CATTCAGACT ACTGCAATAT       420

TGCACAGAAT GCAGCCTCTG GTAAACTCTG TTGTACACTC ATGAGAGAAT GGGTGAAAAA       480

GACAAATTAC GTCTTAGAAT TATTAGAAAT AGCTTTCACT TTAGGAACTC CCTGAGAATT       540

GCTGCTTTAG AGTGGTAAGA TAAATAAGCT TCTCTTTAAA CGGAATCTCA AGACAGAATC       600

AGTTACATTA AAAGCAAACA AAAAATTTGC CCATGGTTAG TCATCTTGTG AAATCTGCCA       660

CACCTTTGGA CTGGGCTACA ATTGGATAAT ATAGCATTCC CCGAGATAAT TTTCTCTCAC       720

AATTAAGGAA AGGGCTGAAT AAATATCTCT GTTTGAAGTT GAATAACAAA AATTAGGACC       780

CCCTAAATTT TAGGGCTCCT GAAATTCGTC TTTTTGCCTA TATTCAGCTA CTTTACGTTC       840

TATTAAATCT TCTTTCAGGC CAGGTGCACT AGCTCATGCC TAGAATCTCA GGCAGGCCTG       900

AGCCCAGGAA TTTGAGACCA GCCAGGGCAA CACAGTCTCT ACAAAAAAAT AAAAAATTAC       960

CTGGGTGTGT TGGTGCATGC CTGTAGAACT ACTCAGGATG CTGAGGACTG CTTGAGCCCA      1020

GGATAGCCAA ATCTGTGGTG AGTTCAGCCA CTAAACAGAG CGAGACTTTC TCAAAAAAAC      1080

AAACAAAAAA ACAAACAAAC TTCCTTCAAA ATAACTTTTT ATCTGCAATG TTTTCCTATT      1140

GCCTGTGAGA TTAAATTTAC TCTTTTACCT GATTTCCAAA GCCCTCCATA ATCTAATCCG      1200

ACTTTACCTT GTGTTCACTG CAAAATAGCA GGACTGTTCC ACTACAATCC AAAAATCACA      1260

GGTTGGGTGC AGTGGCTCAC TCCTGTAATC CCAACACTTT GGAAGGCCAA GGCAGGTGGA      1320

TTGCTTCAGC TCAGGAGTTC AAGACCAGCC TGGGCAACAT GGCAAAAACC CTGTCTCTCC      1380
```

```
AAAACATACA AAAATTAGCC AGATGTGGTA GTATGTGCCT GTAGTCCCAA CTACTCAAAA       1440

GGCTAAGGCA AGAGGATCAC TTGAGCCCAG GAGGTCAAGG CTACAGTGAG CCATGTTTAC       1500

TGTGTCACTG CACTCCAGCC TGGGTGATAG AGCAAGACCA TGTCTCAAAA AAAAAAAAAA       1560

GAAAAGAAAA GAAAAAAACA TCGCTCTATT CAGTTCACCC CCACCACAAC ATTGTTTTGA       1620

TTATCACATA AATGCTGGTC CATTGCCTTC TCTATCTATT CAAATCTTTA AGCATTCTTT       1680

GAGATTCAAC TCAATTCTCC TTTTCAAACT AGGCCATTTA AACTACATCA GTTCCATTTT       1740

GATTTTCTTG CTTTGAGTCT ACAGACTCAA AAACAAAAAC TTAAAAACTT ATTTTTTAAG       1800

TTTTCTGCTA CTCTCACTTC TTCAACACTC ACATACACGC ATTCATAATA AGATGGCAGA       1860

ATGTTCAAGG ATAAAATGAT TTATAGAACT GAAAAGTTAG GTTTTGATCT TGTTGCTGTC       1920

AAGATGACTA CCTACCTGAT CTCAGGTAAT TAATTATGTA GCATGCTCCC TCATTTCATC       1980

CCATACCTAT TCAACAGGAT TGGAATTCCA CAGCAAGGAT AAACATAATC ATAGTTGCTT       2040

TTCAAGTTCA AGGCATTTTA ACTTTTAATC TAGTAGTATG TTTGTTGTTG TTGTTGTTGT       2100

TTGAGATGGA GCCCTGCTGT GTCACCCAGG CTGGAGTGCA GTGGCACGAA CTCGGCTCAC       2160

TGCAACCTCT GCCTCATGGG TTCAATCAGT TATTCTGCCT CAGTGTCCCA AGTAGCTGGG       2220

ACTACAAGGC ACATGCCACC ATGCCTGGCT AATTTTTGTA TTTTTAGTAG AAACAGGGCT       2280

TCACCATGTT GGCCAGGCTG GTCTCGAACT CCTGACCTCA AGTGATCCAG CCGCCTCGGC       2340

CTCCCAAAGT GCTGGGATTA CAGGCATAAG CCACCGTGCC CAGCCTAATA GTATGTTTTT       2400

AAACTCTTAG TGGCTTAACA ATGCTGGTTG TATAATAAAT ATGCCATAAA TATTTACTGT       2460

CTTAGAATTA TGAAGAAGTG GTTACTAGGC CGTTTGCCAC ATATCAATGG TTCTCTCCTT       2520

ACAGCTTTAA TTAGAGTCTA GAATTGCAGG TTGGTAGAGC TGGAACAGAC CTTAAAGATT       2580

GACTAGCCAA CTTCCTTGTC CAAATGAGGG AACTGAGACC CTTAAAATTA AGTGACTTGC       2640

CCCAGACAAA ACTGGAACTC ATGTGTCCTA ATTTCCATCA TGAAATTCTA CCATTCACTA       2700

GCCTCTGGCT AGTTGTCAAA GTATTGCATA ACTAAATTTT TATGTCTGTT TTAAAGAACA       2760

AATTGTCACT GCTTACTCCT GGGAGGGTCT TTCTGAGGTG GTTTATAACT CTTAAAAAAA       2820

AAAAAGTCAG TAGTCTGAGA ATTTTAGACG AAATAGTCAA AGCATTTTTA TCCAATGGAT       2880

CTATAATTTT CATAGATTAG AGTTAAATCA AGAAACACG GATGAGAAAG GAAGAGGAAA       2940

ATTGAGGAGA GGAGGAATGG GGATGAGAAC ACACTACTTG TAATCAGTCA TAGATGTACT       3000

GAGAACTAAC AAGAAGAATT GTAAGAAAAT AAGAATGAAG AATTCAAAAT CAACACATGA       3060

AATAAAAAGA AACTACTAGG GAAAAATGGA GAAGACATTA GAAAAATTAT TCTATTTTTA       3120

AAATTCTGTT TTCAGGCTTC CCTCCTGTTC TTCCTCCTTC TCATTGGTTT TCAGGTGGAG       3180

GGAAAGTTTA AGATGGAAAA AATATATATA TTCTACACAT CCCTTTCTAC GCTGTTGTCA       3240

TGGCAACAAG GTTATCATA GCAAACTTTT ATTCATACAA CATTTATTGA GTTCTTACTG       3300

TGTGGTAAGC TCTTTCCAGG TGTTGAAAAT TCAGGGAAA AAAGACAACT CATTGTCTTA       3360

AAACTCAGAT GAAAGCTGAA CAGACCTATT TTTAATCAAA GTAATCTCAA TTTAGGGTAG       3420

TAAGAGCTAT TTAAGAAGCA TGAACAGGTG TGAAGGAGGT AGGACTCTGA GGAGAGAATA       3480

GTTAGCTAGG AATGAAAGAG CAGAGAAGTT TTCCTAGAGG AACTATTAAA GCTGGGAGTT       3540

ACGGGATGAA AGATGAGGCA GGGTTTGCAG GCAAAAAAAA AAAAAAGGCA GGGGAAGGGG       3600

AAGTTCTGGC CTGGCAGAGA GAATAACTGT GGCAACAATG GAGGAGAGTC TGGAAGCAAG       3660

AAAACCAAGT AGAAGAGTAT TAAAATAGAA GATGCCAGGG GTAATGAGGG CTTGATTTAA       3720
```

```
AACAGTGCTG TTGGAGATGG AGAGGAGATA CCAAATTCTG GAGACATTTC TGAGTTAGAA    3780

CCTACAGTAT TTATCAGACA AGGGAAAGAT TAGACAAAGG AGTTAAGAAT GACTCCCAGG    3840

TTTCAGTTTG GGGCAGGTAA CTAGGACATG TTTTGAAAAG TAATGTATTG GATCTCTTAC    3900

CATTGGAACT ATGTATGTGG AGCCAAATTA AAATTTGTAC ATGTATATAA CTCTCCCCCC    3960

ACCACCAGTA ACTACTTCCC TAACTCTCTA CTTTGTAGCC AGACTTCCTA AAAGAATAGT    4020

TTGTAGTCAC TGTCTTTACT TTTCCCCTCC CATTCTGTCC TAGATATTTG TCCACCTACC    4080

ATCTGCTGCC TCCACTTTAC CCAAACTGTT CTACGGTTGC CCAAAACTTC CTAATTGCCA    4140

AATTCAATGA ACAAGTTTAA GCTTATATGT AAATTAGGAG CTCTACAGTT TGATTTCGAG    4200

CAGCCCCTCC TGAAACCCTT TCTCTTTCGA CTTCTGTGAC ACATCTCAGA TTTACAAAAC    4260

TGAACTAATT ATTTTACACT TGAGCTGTAT TTTCGTTCTT CTTTCTTGAT GAATGAGGTA    4320

ACCACTCAAC AAATTGCCCA AGCCAAAAAC TACGAAGTCA TCCTCAGTTC CTCCTTCTTC    4380

TGTTTGACCC ACAACAGATC AGCTGAGAAA TCCCGCTGTT TAGTATCTCT TGAATTCATT    4440

ACCTTAATTT ATAGCCTCAT CAACTCTTAA TTGTTAAAAT TACTTCAGTA GTTGTTGTCT    4500

GACCTCTGTC CAATCTTGTT CAATCAGGTC CATTCTTTTG TTCTTGGTGG TGGTGGTGGT    4560

GTTGACAGAG TTTCGCTTTT GCTGCCCAGG CTGAAGTGCA GTGGAGCACT TCACTGCAAC    4620

CACAGCCTCC TGGGTTTAAG CAGTTCACCC TCCCGAGTAG CTGGGACTAC AGGTATGTGC    4680

CACCACACCC AGCTAATTTT GTGTTTTCAG TAGAGACAGG GTTTCACCAT GTTGGTCAGG    4740

CTGGTCTCAA ACTCCTGACC TCAAGCAATC CACCCACCTC AGCCTCCCAA AGTGCTGGGA    4800

TTACAGGCAT GAGCCACTGC ACACGGACCA GATCCATTGT TTATGTTGCT TCTAGAGTGA    4860

GTTTTTAAAA CACAAATTTG ACCATATCTT TCTCCAATTT AAGTCAGTAT TTTTTTTTTC    4920

AGGAAAAAAC AGTTCAAACT CTTTAGTCTG CTTACACAAG GCCTTTGTAG TCTGACTCTT    4980

CTTTCCAAGC TTTCATCAAA GTATACTGCA AGTTACATTT TATGTGAATT GAATTAGGCA    5040

ACGGTATAAA AATTATAGTT TATATGGGCA AAATGGAAAT AATGTTAACT CTTCCAAATA    5100

GTTTATCTAG AATGACATAA TTTCAAAGCT GTCAGGTCAA ATGAGTTATA AACTGTTAAC    5160

ACTATTGCCA CATGCAAGTG TCTCTTATAC TTGGTAGAAT TATCTGCTTC CATGTCATTA    5220

TTATGTAAAT TAGACTTTAA ATAACTCAGA AGTTCTTCAG ACATACAGGT TATTATTGTG    5280

CTTTTTAAAC ATAATTTTAA ATAATTTTAT ATATGATAAT GTTATCCAAG TGCTAAGGGA    5340

TGTATTGTTA CTGCTGTGCA AAAAAAAAAA AAAAAAAAAC TCCAAATAAA TATGTTGAAA    5400

CCAAGTTTAT ATGCAAGAAA ACAATATTAA AAAGGCCAAA GTACCACCAT AATAGGCTGT    5460

GTGGAGACGG CAGGCTACAA AACACTAGTA ATAATGCTGA GAAAGTTGAA AAAAGAAAGA    5520

AAGCAACAAT ATGCTTTGGT TGTTGTAGGT TTATGTACTC CAAGAATATC TCCTCTCAAA    5580

CTTTTACGTT TTTTCCAAAG AAAAGTTAAC TTTGGCTGGG CGCAGTGGCT CTTGCCTGTA    5640

GTCCCAGCCT TTGGGAGGCC AAGGCGGGCA GATCACCTGA GGTCAGGAGT TTGAGACCAG    5700

CCTGACCAAA AATGGAGAAA CCCGCCCCCC TCACTACTAA AAGAATACAA AATTAGGCCG    5760

GGCACAGTGG CTTACCCCTG TGATCCCAGC ACTTTGGGAG GCCGAAGCAG GAAGATCACC    5820

TGAGGTCAGG AGTTCGAGAC CAGCCATGGA GAAACCCGTC TCTACTAAAA ATACAAAATT    5880

AGCCGGGCGT GGTGGTGCAT GACTGTAATC CCAGCTACTC AGGAGGCTAA GGCAGAGAAT    5940

CACTTGAACC CAGGCAGTGG AGGTTGCAGT GAGCCGAGAT CGTGCCATTG CACTCCAGCC    6000

TGGGCAACAA GAGCGAAACT CTGTATCCAA AAAACAAAAG AAAAGAAAAG GTAACCTTGA    6060

ACTATGTGAG ATCTTTAGAA ATGCATTCTT TCTGTAAAAT GTGACTACAT TTGCCTTATT    6120
```

```
TATGGTAAAA ATGTTGAGGC CTCAAACAAC CCATATTTTC TCGGTCTCCC CGCTGCCTAG   6180

CCTTTGTTCA CATTGCTTCT TCTTGGTGGA AGCTCTTCCT CTGGCCTTGA AAATGCCTGC   6240

TTCTCTTTCA AGGTAGCACA GTCATCACTT TCTGTGGTAA CCTTCTCCAG CACCATCAAA   6300

CAGAAAGAAT GAATCTCTTG TAAATTCAGC TCTTACGTCA TTCATTACAT TATTTTGTAA   6360

CTCTTTATAG ATTCTTCTCT CCCACTAGAC TCTGAGTCAC TGGAGAGTAG GAGCCAACTC   6420

TCATTCATGT GTGGTTTGGT CAGCTACTGG CCACATTCCT GATGCATAGT TAATGCTCAA   6480

ACCTTAACTG GTGAATCAGC TCAAATATTG TCCTTCTCTA AATCCATTCA CTCATTGACT   6540

AACTATGTAC TCAAAATAGT AAACACCAGT AATTTAATCC AATTCCTGCC CATACTGCTT   6600

GGTACATTTC AGGTGAATTA GTTTGATAAA TATGTGTGTA TTACATAATA TTAAAGTATG   6660

TACAGAAGAT CATGCTAATC ATAATTCACA ACTGATAACT AATCAAACAT AAATGCTCTC   6720

AGGTTAACAA ATGTCTGCCT TCTCAGTTAA TGCAGTCATT AACAAACACC TTCTGATGCT   6780

GATAATAGGG CCTTGTTCAG CAATGAAGCC ATAAAGGTGA ATAAAGAACA TGCCCTCGTG   6840

GAGCTCACAG CCTAGTCATT ATTGTTCTGA TTTTTAATAT TAATGTTGGT TTGGGTTTTG   6900

GTGAAAAATG TTTAGACTTA TCTTAGTGAT CTTTTCATCC TTTGCTATAT TATTTTTCTC   6960

TAAGAGTCTT CCTTATCCCC TCCTTTAAAA AACTAGGTGA TAATTCTAAA TTGTAAATTT   7020

AAATATTATA AATAGCTTAT AAAATTTAAT ATTTATAATA TTTAAATGTT TGATAAATAT   7080

TTAAATTTTA TAATATTTAA ATGTTTATTT AAATTCATTT GTACATCAGT TTTTATTTTA   7140

TTTAAATGTG TTGGCCAGGC ATGGTGGCTG ACACCTATAA TCCCAGAACT TTGAGAGGCC   7200

AAGTCAGGCA AACCATTTGA GCTCAGGAGT TTGAGACCAC CCTGGGCAAC GTGGTGAAAC   7260

CCTGTCTCTA CCAAACATAT GAAAACTTAT CTGGGTGTGG TGGCACGCAT CTGTGGTCCC   7320

AGATGGGAGT CCCAGGCTAA GATGGGAGAA TCGCTTGAAC CCAGGTGAGA GGGGTGGGGT   7380

GGATGTTGCA GTGAGCTGAG ATCGTGCCAC TGCACTCCAA CCTGGGTGAC AGAGTGAGAC   7440

TCCATCTCAA AAAAAAAAAA TGTTATCTAA ATAAGATAAA TTTAATAACT GTTCGCACTT   7500

AGATGAGCAT AAGGAACTAA ACCTAGATAA AACTATCAAA TAAGGCCTGG GTACAGTGAC   7560

TCATGCCTGT AATCTCAAGC ACTTTGGGAG GCCAAAATTA TACAAAGTTA GTTGTATAAC   7620

ACCAACTAAC AACTATTTTG GGGTTAGCTT AATTCAGATT AATTTTTTTT AAACTGAGTT   7680

TTAAATTCCT GCTTACTCTA CCATACATGC TAGGCCTCAT ATTATGCTAG AAAAATTTTG   7740

AGCACAGATT TATGAATACT CTCCTGCATA CCATTTAATT TTTAAACAAA TTTTAATGCA   7800

GTATATATGT GCCTTTTTAC CAACACATTA AATAATAAGA TCTACTGTGA GGACTAAATT   7860

TCTGTAATTT CAAAGTAGTA ATGAGTTTAA ACCATGTCTC AAGATCTCTG CAATAACTGT   7920

AGCACAACAG AAAATAGGTA TTTCTATTAA TGACAGAGTC ACAAGTACTA CTAATAATAC   7980

TGTGGTTTGT TTCCTGCAAC TAATCATGGG AGGAATGCTA AATTTCAGAG GTTGGTGAAA   8040

ATACATGTGT ATTTTTTTCC CCATCCAAGT TCACAGATTT CTCACACTGA GAACTCCTAT   8100

TCCATAACAA AATTCTGGAA GCCTGCACAC CGTATTGGAA GAAGGGCAGA AAGGAAAAGC   8160

AAATGGAAGG ATTTAAATTT TTTTCAAATC CTGTATCCCT TGATTTTACA GCAAGATTGT   8220

ATTTATGTAT TACTTGTGTT AAAAAATATAG TATAATCGAG ACTCCAGATC AAAAATCACC   8280

GCAGCTCAGG GAGAAAGAGG GCCACCAAAT GCCAGAGCCC TTCAGCCTTC TCCCACCCTG   8340

CCTGTACCCT CAGATGGAAG CACTTTTTTA TCATTGTTTC ACCTTTAGCA TTTTGACAAT   8400

GAAGTCACAA ACCTTCAGCC TCTCACCCAT AGGAACCCAC TGGTTGTAAG AGAAGGATGA   8460
```

-continued

| AGCCAGTCCT TCCTAAAGGG CACGATTAGA TGTGTTTATG GCATCCTCAG GTGAAACTAT | 8520 |
| ATTTATATTG ACAATATATT TATATTTCTC AAGGAATACT AGAATAATGA TTCAGTTCAG | 8580 |
| TACTAGGCCA TTTATCTACC CTTTATAATA TTGTTTAATG AGAAAATGCT TTCTATCTTC | 8640 |
| CAAATATCTG ATGATTTGTA AGAGAACACT TAAACATGGG TATTCATAAG CTGAAACTTC | 8700 |
| TGGCATTTAT TGAATGTCAA GATTGTTCAT CAGTATACTA GGTGATTAAC TGACCACTGA | 8760 |
| ACTTGAAGGT AGTATAAAGT AGTAGTAAAA GGTACAATCA TTGTCTCTTA ACAGATGGCT | 8820 |
| CTTTGCTTTC ATTAG | 8835 |

(2) INFORMATION FOR SEQ ID NO:11:

(i) SEQUENCE CHARACTERISTICS:
        (A) LENGTH: 1371 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: intron
        (B) LOCATION: 1..1371
        (C) IDENTIFICATION METHOD: E (xi) SEQUENCE DESCRIPTION: SEQ ID NO: 11:

| GTAAGGCTAA TGCCATAGAA CAAATACCAG GTTCAGATAA ATCTATTCAA TTAGAAAAGA | 60 |
| TGTTGTGAGG TGAACTATTA AGTGACTCTT TGTGTCACCA AATTTCACTG TAATATTAAT | 120 |
| GGCTCTTAAA AAAATAGTGG ACCTCTAGAA ATTAACCACA ACATGTCCAA GGTCTCAGCA | 180 |
| CCTTGTCACA CCACGTGTCC TGGCACTTTA ATCAGCAGTA GCTCACTCTC CAGTTGGCAG | 240 |
| TAAGTGCACA TCATGAAAAT CCCAGTTTTC ATGGGAAAAT CCCAGTTTTC ATTGGATTTC | 300 |
| CATGGGAAAA ATCCCAGTAC AAAACTGGGT GCATTCAGGA AATACAATTT CCCAAAGCAA | 360 |
| ATTGGCAAAT TATGTAAGAG ATTCTCTAAA TTTAGAGTTC CGTGAATTAC ACCATTTTAT | 420 |
| GTAAATATGT TTGACAAGTA AAAATTGATT CTTTTTTTTT TTTTCTGTTG CCCAGGCTGG | 480 |
| AGTGCAGTGG CACAATCTCT GCTCACTGCA ACCTCCACCT CCTGGGTTCA AGCAATTCTC | 540 |
| CTGCCTCAGC CTTCTGAGTA GCTGGGACTA CAGGTGCATC CCGCCATGCC TGGCTAATTT | 600 |
| TTGGGTATTT TTACTAGAGA CAGGGTTTTG GCATGTTGTC CAGGCTGGTC TTGGACTCCT | 660 |
| GATCTCAGAT GATCCTCCTG GCTCGGGCTC CCAAAGTGCT GGGATTACAG GCATGAACCA | 720 |
| CCACACATGG CCTAAAAATT GATTCTTATG ATTAATCTCC TGTGAACAAT TTGGCTTCAT | 780 |
| TTGAAAGTTT GCCTTCATTT GAAACCTTCA TTTAAAAGCC TGAGCAACAA AGTGAGACCC | 840 |
| CATCTCTACA AAAAACTGCA AAATATCCTG TGGACACCTC CTACCTTCTG TGGAGGCTGA | 900 |
| AGCAGGAGGA TCACTTGAGC CTAGGAATTT GAGCCTGCAG TGAGCTATGA TCCCACCCCT | 960 |
| ACACTCCAGC CTGCATGACA GTAGACCCTG ACACACACAC ACAAAAAAAA ACCTTCATAA | 1020 |
| AAAATTATTA GTTGACTTTT CTTAGGTGAC TTTCCGTTTA AGCAATAAAT TTAAAGTAA | 1080 |
| AATCTCTAAT TTTAGAAAAT TTATTTTTAG TTACATATTG AAATTTTTAA ACCCTAGGTT | 1140 |
| TAAGTTTTAT GTCTAAATTA CCTGAGAACA CACTAAGTCT GATAAGCTTC ATTTTATGGG | 1200 |
| CCTTTTGGAT GATTATATAA TATTCTGATG AAAGCCAAGA CAGACCCTTA AACCATAAAA | 1260 |
| ATAGGAGTTC GAGAAAGAGG AGTAGCAAAA GTAAAAGCTA GAATGAGATT GAATTCTGAG | 1320 |

```
TCGAAATACA AAATTTTACA TATTCTGTTT CTCTCTTTTT CCCCCTCTTA G            1371
```

(2) INFORMATION FOR SEQ ID NO: 12:

(i) SEQUENCE CHARACTERISTICS:
        (A) LENGTH: 3383 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: intron
        (B) LOCATION: 1..3383
        (C) IDENTIFICATION METHOD: E (xi) SEQUENCE DESCRIPTION: SEQ ID NO: 12:

```
GTAAAGTAGA AATGAATTTA TTTTTCTTTG CAAACTAAGT ATCTGCTTGA GACACATCTA     60
TCTCACCATT GTCAGCTGAG GAAAAAAAAA AATGGTTCTC ATGCTACCAA TCTGCCTTCA   120
AAGAAATGTG GACTCAGTAG CACAGCTTTG GAATGAAGAT GATCATAAGA GATCAAAGA    180
AGAACCTCTA GCAAAAGATG CTTCTCTATG CCTTAAAAAA TTCTCCAGCT CTTAGAATCT   240
ACAAAATAGA CTTTGCCTGT TTCATTGGTC CTAAGATTAG CATGAAGCCA TGGATTCTGT   300
TGTAGGGGGA GCGTTGCATA GGAAAAAGGG ATTGAAGCAT TAGAATTGTC CAAAATCAGT   360
AACACCTCCT CTCAGAAATG CTTTGGGAAG AAGCCTGGAA GGTTCCGGGT TGGTGGTGGG   420
GTGGGGCAGA AAATTCTGGA AGTAGAGGAG ATAGGAATGG GTGGGGCAAG AAGACCACAT   480
TCAGAGGCCA AAAGCTGAAA GAAACCATGG CATTTATGAT GAATTCAGGG TAATTCAGAA   540
TGGAAGTAGA GTAGGAGTAG GAGACTGGTG AGAGGAGCTA GAGTGATAAA CAGGGTGTAG   600
AGCAAGACGT TCTCTCACCC CAAGATGTGA AATTTGGACT TTATCTTGGA GATAATAGGG   660
TTAATTAAGC ACAATATGTA TTAGCTAGGG TAAAGATTAG TTTGTTGTAA CAAAGACATC   720
CAAAGATACA GTAGCTGAAT AAGATAGAGA ATTTTTCTCT CAAAGAAAGT CTAAGTAGGC   780
AGCTCAGAAG TAGTATGGCT GGAAGCAACC TGATGATATT GGGACCCCCA ACCTTCTTCA   840
GTCTTGTACC CATCATCCCC TAGTTGTTGA TCTCACTCAC ATAGTTGAAA ATCATCATAC   900
TTCCTGGGTT CATATCCCAG TTATCAAGAA AGGGTCAAGA GAAGTCAGGC TCATTCCTTT   960
CAAAGACTCT AATTGGAAGT TAAACACATC AATCCCCCTC ATATTCCATT GACTAGAATT  1020
TAATCACATG GCCACACCAA GTGCAAGGAA ATCTGGAAAA TATAATCTTT ATTCCAGGTA  1080
GCCATATGAC TCTTTAAAAT TCAGAAATAA TATATTTTTA AAATATCATT CTGGCTTTGG  1140
TATAAAGAAT TGATGGTGTG GGGTGAGGAG GCCAAAATTA AGGGTTGAGA GCCTATTATT  1200
TTAGTTATTA CAAGAAATGA TGGTGTCATG AATTAAGGTA GACATAGGGG AGTGCTGATG  1260
AGGAGCTGTG AATGGATTTT AGAAACACTT GAGAGAATCA ATAGGACATG ATTTAGGGTT  1320
GGATTTGGAA AGGAGAAGAA AGTAGAAAAG ATGATGCCTA CATTTTTCAC TTAGGCAATT  1380
TGTACCATTC AGTGAAATAG GGAACACAGG AGGAAGAGCA GGTTTTGGTG TATACAAAGA  1440
GGAGGATGGA TGACGCATTT CGTTTTGGAT CTGAGATGTC TGTGGAACGT CCTAGTGGAG  1500
ATGTCCACAA ACTCTTCTAC ATGTGGTTCT GAGTTCAGGA CACAGATTTG GGCTGGAGAT  1560
AGAGATATTG TAGGCTTATA CATAGAAATG GCATTTGAAT CTATAGAGAT AAAAAGACAC  1620
```

```
ATCAGAGGAA ATGTGTAAAG TGAGAGAGGA AAAGCCAAGT ACTGTGCTGG GGGGAATACC   1680

TACATTTAAA GGATGCAGTA GAAAGAAGCT AATAAACAAC AGAGAGCAGA CTAACCAAAA   1740

GGGGAGAAGA AAAACCAAGA GAATTCCACC GACTCCCAGG AGAGCATTTC AAGATTGAGG   1800

GGATAGGTGT TGTGTTGAAT TTTGCAGCCT TGAGAATCAA GGGCCAGAAC ACAGCTTTTA   1860

GATTTAGCAA CAAGGAGTTT GGTGATCTCA GTGAAAGCAG CTTGATGGTG AAATGGAGGC   1920

AGAGGCAGAT TGCAATGAGT GAAACAGTGA ATGGGAAGTG AAGAAATGAT ACAGATAATT   1980

CTTGCTAAAA GCTTGGCTGT TAAAAGGAGG AGAGAAACAA GACTAGCTGC AAAGTGAGAT   2040

TGGGTTGATG GAGCAGTTTT AAATCTCAAA ATAAAGAGCT TTGTGCTTTT TTGATTATGA   2100

AAATAATGTG TTAATTGTAA CTAATTGAGG CAATGAAAAA AGATAATAAT ATGAAAGATA   2160

AAAATATAAA AACCACCCAG AAATAATGAT AGCTACCATT TTGATACAAT ATTTCTACAC   2220

TCCTTTCTAT GTATATATAC AGACACAGAA ATGCTTATAT TTTTATTAAA AGGGATTGTA   2280

CTATACCTAA GCTGCTTTTT CTAGTTAGTG ATATATATGG ACATCTCTCC ATGGCAACGA   2340

GTAATTGCAG TTATATTAAG TTCATGATAT TTCACAATAA GGGCATATCT TTGCCCTTTT   2400

TATTTAATCA ATTCTTAATT GGTGAATGTT TGTTTCCAGT TTGTTGTTGT TATTAACAAT   2460

GTTCCCATAA GCATTCCTGT ACACCAATGT TCACACATTT GTCTGATTTT TTCTTCAGGA   2520

TAAAACCCAG GAGGTAGAAT TGCTGGGTTG ATAGAAGAGA AAGGATGATT GCCAAATTAA   2580

AGCTTCAGTA GAGGGTACAT GCCGAGCACA AATGGGATCA GCCCTAGATA CCAGAAATGG   2640

CACTTTCTCA TTTCCCCTTG GGACAAAAGG GAGAGAGGCA ATAACTGTGC TGCCAGAGTT   2700

AAATTTGTAC GTGGAGTAGC AGGAAATCAT TTGCTGAAAA TGAAACAGA GATGATGTTG    2760

TAGAGGTCCT GAAGAGAGCA AAGAAAATTT GAAATTGCGG CTATCAGCTA TGGAAGAGAG   2820

TGCTGAACTG GAAAACAAAA GAAGTATTGA CAATTGGTAT GCTTGTAATG GCACCGATTT   2880

GAACGCTTGT GCCATTGTTC ACCAGCAGCA CTCAGCAGCC AAGTTTGGAG TTTTGTAGCA   2940

GAAAGACAAA TAAGTTAGGG ATTTAATATC CTGGCCAAAT GGTAGACAAA ATGAACTCTG   3000

AGATCCAGCT GCACAGGGAA GGAAGGGAAG ACGGGAAGAG GTTAGATAGG AAATACAAGA   3060

GTCAGGAGAC TGGAAGATGT TGTGATATTT AAGAACACAT AGAGTTGGAG TAAAAGTGTA   3120

AGAAAACTAG AAGGGTAAGA GACCGGTCAG AAAGTAGGCT ATTTGAAGTT AACACTTCAG   3180

AGGCAGAGTA GTTCTGAATG GTAACAAGAA ATTGAGTGTG CCTTTGAGAG TAGGTTAAAA   3240

AACAATAGGC AACTTTATTG TAGCTACTTC TGGAACAGAA GATTGTCATT AATAGTTTTA   3300

GAAAACTAAA ATATATAGCA TACTTATTTG TCAATTAACA AAGAAACTAT GTATTTTTAA   3360

ATGAGATTTA ATGTTTATTG TAG                                          3383
```

(2) INFORMATION FOR SEQ ID NO: 13:

(i) SEQUENCE CHARACTERISTICS:
        (A) LENGTH: 11464 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: 5'UTR
        (B) LOCATION: 1..3
        (C) IDENTIFICATION METHOD: E (A) NAME/KEY: leader peptide
        (B) LOCATION: 4..82
        (C) IDENTIFICATION METHOD: S
        (A) NAME/KEY: intron
        (B) LOCATION: 83..1453
        (C) IDENTIFICATION METHOD: E
        (A) NAME/KEY: leader peptide
        (B) LOCATION: 1454..1465
        (C) IDENTIFICATION METHOD: S
        (A) NAME/KEY: intron
        (B) LOCATION: 1466..4848
        (C) IDENTIFICATION METHOD: E
        (A) NAME/KEY: leader peptide
        (B) LOCATION: 4849..4865
        (C) IDENTIFICATION METHOD: S
        (A) NAME/KEY: mat peptide
        (B) LOCATION: 4866..4983
        (C) IDENTIFICATION METHOD: S
        (A) NAME/KEY: intron
        (B) LOCATION: 4984..6317
        (C) IDENTIFICATION METHOD: E
        (A) NAME/KEY: mat peptide
        (B) LOCATION: 6318..6451
        (C) IDENTIFICATION METHOD: S
        (A) NAME/KEY: intron
        (B) LOCATION: 6452..11224
        (C) IDENTIFICATION METHOD: E
        (A) NAME/KEY: mat peptide
        (B) LOCATION: 11225..11443
        (C) IDENTIFICATION METHOD: S
        (A) NAME/KEY: 3'UTR
        (B) LOCATION: 11444..11464
        (C) IDENTIFICATION METHOD: E (xi) SEQUENCE DESCRIPTION: SEQ ID NO: 13:

```
AAG ATG GCT GCT GAA CCA GTA GAA GAC AAT TGC ATC AAC TTT GTG GCA      48
    Met Ala Ala Glu Pro Val Glu Asp Asn Cys Ile Asn Phe Val Ala
        -35              -30              -25

ATG AAA TTT ATT GAC AAT ACG CTT TAC TTT ATA G   GTAAGG CTAATGCCAT    98
Met Lys Phe Ile Asp Asn Thr Leu Tyr Phe Ile Ala
    -20              -15              -10

AGAACAAATA CCAGGTTCAG ATAAATCTAT TCAATTAGAA AAGATGTTGT GAGGTGAACT   158

ATTAAGTGAC TCTTTGTGTC ACCAAATTTC ACTGTAATAT TAATGGCTCT TAAAAAATA   218

GTGGACCTCT AGAAATTAAC CACAACATGT CCAAGGTCTC AGCACCTTGT CACACCACGT   278

GTCCTGGCAC TTTAATCAGC AGTAGCTCAC TCTCCAGTTG GCAGTAAGTG CACATCATGA   338

AAATCCCAGT TTTCATGGGA AAATCCCAGT TTTCATTGGA TTTCCATGGG AAAAATCCCA   398

GTACAAAACT GGGTGCATTC AGGAAATACA ATTTCCCAAA GCAAATTGGC AAATTATGTA   458

AGAGATTCTC TAAATTTAGA GTTCCGTGAA TTACACCATT TTATGTAAAT ATGTTTGACA   518

AGTAAAAATT GATTCTTTTT TTTTTTTTCT GTTGCCCAGG CTGGAGTGCA GTGGCACAAT   578

CTCTGCTCAC TGCAACCTCC ACCTCCTGGG TTCAAGCAAT TCTCCTGCCT CAGCCTTCTG   638

AGTAGCTGGG ACTACAGGTG CATCCCGCCA TGCCTGGCTA ATTTTTGGGT ATTTTTACTA   698

GAGACAGGGT TTTGGCATGT TGTCCAGGCT GGTCTTGGAC TCCTGATCTC AGATGATCCT   758

CCTGGCTCGG GCTCCCAAAG TGCTGGGATT ACAGGCATGA ACCACCACAC ATGGCCTAAA   818

AATTGATTCT TATGATTAAT CTCCTGTGAA CAATTTGGCT TCATTTGAAA GTTTGCCTTC   878

ATTTGAAACC TTCATTTAAA AGCCTGAGCA ACAAAGTGAG ACCCCATCTC TACAAAAAAC   938

TGCAAAATAT CCTGTGGACA CCTCCTACCT TCTGTGGAGG CTGAAGCAGG AGGATCACTT   998

GAGCCTAGGA ATTTGAGCCT GCAGTGAGCT ATGATCCCAC CCTACACTC CAGCCTGCAT   1058

GACAGTAGAC CCTGACACAC ACACACAAAA AAAAACCTTC ATAAAAAATT ATTAGTTGAC   1118

TTTTCTTAGG TGACTTTCCG TTTAAGCAAT AAATTTAAAA GTAAATCTC TAATTTTAGA   1178
```

```
AAATTTATTT TTAGTTACAT ATTGAAATTT TTAAACCCTA GGTTTAAGTT TTATGTCTAA    1238

ATTACCTGAG AACACACTAA GTCTGATAAG CTTCATTTTA TGGGCCTTTT GGATGATTAT    1298

ATAATATTCT GATGAAAGCC AAGACAGACC CTTAAACCAT AAAAATAGGA GTTCGAGAAA    1358

GAGGAGTAGC AAAAGTAAAA GCTAGAATGA GATTGAATTC TGAGTCGAAA TACAAAATTT    1418

TACATATTCT GTTTCTCTCT TTTTCCCCCT CTTAG    CT GAA GAT GAT G   GTAAA    1470
                                     Ala Glu Asp Asp Glu
                                     -10

GTAGAAATGA ATTTATTTTT CTTTGCAAAC TAAGTATCTG CTTGAGACAC ATCTATCTCA    1530

CCATTGTCAG CTGAGGAAAA AAAAAAATGG TTCTCATGCT ACCAATCTGC CTTCAAAGAA    1590

ATGTGGACTC AGTAGCACAG CTTTGGAATG AAGATGATCA TAAGAGATAC AAAGAAGAAC    1650

CTCTAGCAAA AGATGCTTCT CTATGCCTTA AAAAATTCTC CAGCTCTTAG AATCTACAAA    1710

ATAGACTTTG CCTGTTTCAT TGGTCCTAAG ATTAGCATGA AGCCATGGAT TCTGTTGTAG    1770

GGGGAGCGTT GCATAGGAAA AAGGGATTGA AGCATTAGAA TTGTCCAAAA TCAGTAACAC    1830

CTCCTCTCAG AAATGCTTTG GAAGAAGCC TGGAAGGTTC CGGGTTGGTG GTGGGGTGGG    1890

GCAGAAAATT CTGGAAGTAG AGGAGATAGG AATGGGTGGG GCAAGAAGAC CACATTCAGA    1950

GGCCAAAAGC TGAAAGAAAC CATGGCATTT ATGATGAATT CAGGGTAATT CAGAATGGAA    2010

GTAGAGTAGG AGTAGGAGAC TGGTGAGAGG AGCTAGAGTG ATAAACAGGG TGTAGAGCAA    2070

GACGTTCTCT CACCCCAAGA TGTGAAATTT GGACTTTATC TTGGAGATAA TAGGGTTAAT    2130

TAAGCACAAT ATGTATTAGC TAGGGTAAAG ATTAGTTTGT TGTAACAAAG ACATCCAAAG    2190

ATACAGTAGC TGAATAAGAT AGAGAATTTT TCTCTCAAAG AAAGTCTAAG TAGGCAGCTC    2250

AGAAGTAGTA TGGCTGGAAG CAACCTGATG ATATTGGGAC CCCCAACCTT CTTCAGTCTT    2310

GTACCCATCA TCCCCTAGTT GTTGATCTCA CTCACATAGT TGAAAATCAT CATACTTCCT    2370

GGGTTCATAT CCCAGTTATC AAGAAAGGGT CAAGAGAAGT CAGGCTCATT CCTTTCAAAG    2430

ACTCTAATTG GAAGTTAAAC ACATCAATCC CCCTCATATT CCATTGACTA GAATTTAATC    2490

ACATGGCCAC ACCAAGTGCA AGGAAATCTG GAAAATATAA TCTTTATTCC AGGTAGCCAT    2550

ATGACTCTTT AAAATTCAGA ATAATATAT TTTTAAAATA TCATTCTGGC TTTGGTATAA     2610

AGAATTGATG GTGTGGGGTG AGGAGGCCAA AATTAAGGGT TGAGAGCCTA TTATTTTAGT    2670

TATTACAAGA AATGATGGTG TCATGAATTA AGGTAGACAT AGGGGAGTGC TGATGAGGAG    2730

CTGTGAATGG ATTTTAGAAA CACTTGAGAG AATCAATAGG ACATGATTTA GGGTTGGATT    2790

TGGAAAGGAG AAGAAAGTAG AAAAGATGAT GCCTACATTT TTCACTTAGG CAATTTGTAC    2850

CATTCAGTGA AATAGGGAAC ACAGGAGGAA GAGCAGGTTT TGGTGTATAC AAAGAGGAGG    2910

ATGGATGACG CATTTCGTTT TGGATCTGAG ATGTCTGTGG AACGTCCTAG TGGAGATGTC    2970

CACAAACTCT TCTACATGTG GTTCTGAGTT CAGGACACAG ATTTGGGCTG AGATAGAGA     3030

TATTGTAGGC TTATACATAG AAATGGCATT TGAATCTATA GAGATAAAAA GACACATCAG    3090

AGGAAATGTG TAAAGTGAGA GAGGAAAAGC CAAGTACTGT GCTGGGGGGA ATACCTACAT    3150

TTAAAGGATG CAGTAGAAAG AAGCTAATAA ACAACAGAGA GCAGACTAAC CAAAAGGGGA    3210

GAAGAAAAAC CAAGAGAATT CCACCGACTC CCAGGAGAGC ATTTCAAGAT TGAGGGGATA    3270

GGTGTTGTGT TGAATTTTGC AGCCTTGAGA ATCAAGGGCC AGAACACAGC TTTTAGATTT    3330

AGCAACAAGG AGTTTGGTGA TCTCAGTGAA AGCAGCTTGA TGGTGAAATG GAGGCAGAGG    3390

CAGATTGCAA TGAGTGAAAC AGTGAATGGG AAGTGAAGAA ATGATACAGA TAATTCTTGC    3450
```

```
TAAAAGCTTG GCTGTTAAAA GGAGGAGAGA AACAAGACTA GCTGCAAAGT GAGATTGGGT    3510

TGATGGAGCA GTTTTAAATC TCAAAATAAA GAGCTTTGTG CTTTTTTGAT TATGAAAATA    3570

ATGTGTTAAT TGTAACTAAT TGAGGCAATG AAAAAGATA  ATAATATGAA AGATAAAAAT    3630

ATAAAAACCA CCCAGAAATA ATGATAGCTA CCATTTTGAT ACAATATTTC TACACTCCTT    3690

TCTATGTATA TATACAGACA CAGAAATGCT TATATTTTTA TTAAAAGGGA TTGTACTATA    3750

CCTAAGCTGC TTTTTCTAGT TAGTGATATA TATGGACATC TCTCCATGGC AACGAGTAAT    3810

TGCAGTTATA TTAAGTTCAT GATATTTCAC AATAAGGGCA TATCTTTGCC CTTTTTATTT    3870

AATCAATTCT TAATTGGTGA ATGTTTGTTT CCAGTTTGTT GTTGTTATTA ACAATGTTCC    3930

CATAAGCATT CCTGTACACC AATGTTCACA CATTTGTCTG ATTTTTTCTT CAGGATAAAA    3990

CCCAGGAGGT AGAATTGCTG GGTTGATAGA AGAGAAAGGA TGATTGCCAA ATTAAAGCTT    4050

CAGTAGAGGG TACATGCCGA GCACAAATGG GATCAGCCCT AGATACCAGA AATGGCACTT    4110

TCTCATTTCC CCTTGGGACA AAAGGGAGAG AGGCAATAAC TGTGCTGCCA GAGTTAAATT    4170

TGTACGTGGA GTAGCAGGAA ATCATTTGCT GAAAATGAAA ACAGAGATGA TGTTGTAGAG    4230

GTCCTGAAGA GAGCAAAGAA AATTTGAAAT TGCGGCTATC AGCTATGGAA GAGAGTGCTG    4290

AACTGGAAAA CAAAAGAAGT ATTGACAATT GGTATGCTTG TAATGGCACC GATTTGAACG    4350

CTTGTGCCAT TGTTCACCAG CAGCACTCAG CAGCCAAGTT TGGAGTTTTG TAGCAGAAAG    4410

ACAAATAAGT TAGGGATTTA ATATCCTGGC CAAATGGTAG ACAAAATGAA CTCTGAGATC    4470

CAGCTGCACA GGGAAGGAAG GGAAGACGGG AAGAGGTTAG ATAGGAAATA CAAGAGTCAG    4530

GAGACTGGAA GATGTTGTGA TATTTAAGAA CACATAGAGT TGGAGTAAAA GTGTAAGAAA    4590

ACTAGAAGGG TAAGAGACCG GTCAGAAAGT AGGCTATTTG AAGTTAACAC TTCAGAGGCA    4650

GAGTAGTTCT GAATGGTAAC AAGAAATTGA GTGTGCCTTT GAGAGTAGGT TAAAAAACAA    4710

TAGGCAACTT TATTGTAGCT ACTTCTGGAA CAGAAGATTG TCATTAATAG TTTTAGAAAA    4770

CTAAAATATA TAGCATACTT ATTTGTCAAT TAACAAAGAA ACTATGTATT TTTAAATGAG    4830

ATTTAATGTT TATTGTAG  AA AAC CTG GAA TCA GAT TAC TTT GGC AAG CTT    4880
                    Glu Asn Leu Glu Ser Asp Tyr Phe Gly Lys Leu
                      -5                 1                   5

GAA TCT AAA TTA TCA GTC ATA AGA AAT TTG AAT GAC CAA GTT CTC TTC    4928
Glu Ser Lys Leu Ser Val Ile Arg Asn Leu Asn Asp Gln Val Leu Phe
             10                  15                  20

ATT GAC CAA GGA AAT CGG CCT CTA TTT GAA GAT ATG ACT GAT TCT GAC    4976
Ile Asp Gln Gly Asn Arg Pro Leu Phe Glu Asp Met Thr Asp Ser Asp
             25                  30                  35

TGT AGA G   GTATTTTTT TTAATTCGCA AACATAGAAA TGACTAGCTA CTTCTTCCCA    5032
Cys Arg Asp
         40

TTCTGTTTTA CTGCTTACAT TGTTCCGTGC TAGTCCCAAT CCTCAGATGA AAAGTCACAG    5092

GAGTGACAAT AATTTCACTT ACAGGAAACT TTATAAGGCA TCCACGTTTT TTAGTTGGGG    5152

TAAAAAATTG GATACAATAA GACATTGCTA GGGGTCATGC CTCTCTGAGC CTGCCTTTGA    5212

ATCACCAATC CCTTTATTGT GATTGCATTA ACTGTTAAA  ACCTCTATAG TTGGATGCTT    5272

AATCCCTGCT TGTTACAGCT GAAAATGCTG ATAGTTTACC AGGTGTGGTG GCATCTATCT    5332

GTAATCCTAG CTACTTGGGA GGCTCAAGCA GGAGGATTGC TTGAGGCCAG GACTTTGAGG    5392

CTGTAGTACA CTGTGATCGT ACCTGTGAAT AGCCACTGCA CTCCAGCCTG GGTGATATAC    5452

AGACCTTGTC TCTAAAATTA AAAAAAAAA  AAAAAAAAC  CTTAGGAAAG GAAATTGATC    5512

AAGTCTACTG TGCCTTCCAA AACATGAATT CCAAATATCA AAGTTAGGCT GAGTTGAAGC    5572
```

```
AGTGAATGTG CATTCTTTAA AAATACTGAA TACTTACCTT AACATATATT TTAAATATTT     5632

TATTTAGCAT TTAAAAGTTA AAAACAATCT TTTAGAATTC ATATCTTTAA AATACTCAAA     5692

AAAGTTGCAG CGTGTGTGTT GTAATACACA TTAAACTGTG GGGTTGTTTG TTTGTTTGAG     5752

ATGCAGTTTC ACTCTGTCAC CCAGGCTGAA GTGCAGTGCA GTGCAGTGGT GTGATCTCGG     5812

CTCACTACAA CCTCCACCTC CCACGTTCAA GCGATTCTCA TGCCTCAGTC TCCCGAGTAG     5872

GTGGGATTAC AGGCATGCAC CACTTACACC CGGCTAATTT TTGTATTTTT AGTAGAGCTG     5932

GGGTTTCACC ATGTTGGCCA GGCTGGTCTC AAACCCCTAA CCTCAAGTGA TCTGCCTGCC     5992

TCAGCCTCCC AAACAAACAA ACAACCCCAC AGTTTAATAT GTGTTACAAC ACACATGCTG     6052

CAACTTTTAT GAGTATTTTA ATGATATAGA TTATAAAAGG TTGTTTTTAA CTTTTAAATG     6112

CTGGGATTAC AGGCATGAGC CACTGTGCCA GGCCTGAACT GTGTTTTTAA AAATGTCTGA     6172

CCAGCTGTAC ATAGTCTCCT GCAGACTGGC CAAGTCTCAA AGTGGGAACA GGTGTATTAA     6232

GGACTATCCT TTGGTTAAAT TTCCGCAAAT GTTCCTGTGC AAGAATTCTT CTAACTAGAG     6292

TTCTCATTTA TTATATTTAT TTCAG  AT AAT GCA CCC CGG ACC ATA TTT ATT       6343
                             Asp Asn Ala Pro Arg Thr Ile Phe Ile
                              40              45

ATA AGT ATG TAT AAA GAT AGC CAG CCT AGA GGT ATG GCT GTA ACT ATC       6391
Ile Ser Met Tyr Lys Asp Ser Gln Pro Arg Gly Met Ala Val Thr Ile
 50                  55                  60

TCT GTG AAG TGT GAG AAA ATT TCA ACT CTC TCC TGT GAG AAC AAA ATT       6439
Ser Val Lys Cys Glu Lys Ile Ser Thr Leu Ser Cys Glu Asn Lys Ile
 65                  70                  75                  80

ATT TCC TTT AAG GTAAG ACTGAGCCTT ACTTTGTTTT CAATCATGTT AATATAATCA     6496
Ile Ser Phe Lys

ATATAATTAG AAATATAACA TTATTTCTAA TGTTAATATA AGTAATGTAA TTAGAAAACT     6556

CAAATATCCT CAGACCAACC TTTTGTCTAG AACAGAAATA ACAAGAAGCA GAGAACCATT     6616

AAAGTGAATA CTTACTAAAA ATTATCAAAC TCTTTACCTA TTGTGATAAT GATGGTTTTT     6676

CTGAGCCTGT CACAGGGGAA GAGGAGATAC AACACTTGTT TTATGACCTG CATCTCCTGA     6736

ACAATCAGTC TTTATACAAA TAATAATGTA GAATACATAT GTGAGTTATA CATTTAAGAA     6796

TAACATGTGA CTTTCAGAA TGAGTTCTGC TATGAAGAAT GAAGCTAATT ATCCTTCTAT      6856

ATTTCTACAC CTTTGTAAAT TATGATAATA TTTTAATCCC TAGTTGTTTT GTTGCTGATC     6916

CTTAGCCTAA GTCTTAGACA CAAGCTTCAG CTTCCAGTTG ATGTATGTTA TTTTTAATGT     6976

TAATCTAATT GAATAAAAGT TATGAGATCA GCTGTAAAAG TAATGCTATA ATTATCTTCA     7036

AGCCAGGTAT AAAGTATTTC TGGCCTCTAC TTTTTCTCTA TTATTCTCCA TTATTATTCT     7096

CTATTATTTT TCTCTATTTC CTCCATTATT GTTAGATAAA CCACAATTAA CTATAGCTAC     7156

AGACTGAGCC AGTAAGAGTA GCCAGGGATG CTTACAAATT GGCAATGCTT CAGAGGAGAA     7216

TTCCATGTCA TGAAGACTCT TTTTGAGTGG AGATTTGCCA ATAAATATCC GCTTTCATGC     7276

CCACCCAGTC CCCACTGAAA GACAGTTAGG ATATGACCTT AGTGAAGGTA CCAAGGGGCA     7336

ACTTGGTAGG GAGAAAAAAG CCACTCTAAA ATATAATCCA AGTAAGAACA GTGCATATGC     7396

AACAGATACA GCCCCAGAC AAATCCCTCA GCTATCTCCC TCCAACCAGA GTGCCACCCC      7456

TTCAGGTGAC AATTTGGAGT CCCCATTCTA GACCTGACAG GCAGCTTAGT TATCAAAATA     7516

GCATAAGAGG CCTGGGATGG AAGGGTAGGG TGGAAAGGGT TAAGCATGCT GTTACTGAAC     7576

AACATAATTA GAAGGGAAGG AGATGGCCAA GCTCAAGCTA TGTGGGATAG AGGAAAACTC     7636

AGCTGCAGAG GCAGATTCAG AAACTGGGAT AAGTCCGAAC CTACAGGTGG ATTCTTGTTG     7696
```

```
AGGGAGACTG GTGAAAATGT TAAGAAGATG GAAATAATGC TTGGCACTTA GTAGGAACTG      7756

GGCAAATCCA TATTTGGGGG AGCCTGAAGT TTATTCAATT TTGATGGCCC TTTTAAATAA      7816

AAAGAATGTG GCTGGGCGTG GTGGCTCACA CCTGTAATCC CAGCACTTTG GGAGGCCGAG      7876

GGGGGCGGAT CACCTGAAGT CAGGAGTTCA AGACCAGCCT GACCAACATG GAGAAACCCC      7936

ATCTCTACTA AAAATACAAA ATTAGCTGGG CGTGGTGGCA TATGCCTGTA ATCCCAGCTA      7996

CTCGGGAGGC TGAGGCAGGA GAATCTTTTG AACCCGGGAG GCAGAGGTTG CGATGAGCCT      8056

AGATCGTGCC ATTGCACTCC AGCCTGGGCA ACAAGAGCAA AACTCGGTCT CAAAAAAAAA      8116

AAAAAAAAAG TGAAATTAAC CAAAGGCATT AGCTTAATAA TTTAATACTG TTTTTAAGTA      8176

GGGCGGGGGG TGGCTGGAAG AGATCTGTGT AAATGAGGGA ATCTGACATT TAAGCTTCAT      8236

CAGCATCATA GCAAATCTGC TTCTGGAAGG AACTCAATAA ATATTAGTTG GAGGGGGGGA      8296

GAGAGTGAGG GGTGGACTAG GACCAGTTTT AGCCCTTGTC TTTAATCCCT TTTCCTGCCA      8356

CTAATAAGGA TCTTAGCAGT GGTTATAAAA GTGGCCTAGG TTCTAGATAA TAAGATACAA      8416

CAGGCCAGGC ACAGTGGCTC ATGCCTATAA TCCCAGCACT TTGGGAGGGC AAGGCGAGTG      8476

TCTCACTTGA GATCAGGAGT TCAAGACCAG CCTGGCCAGC ATGGCGATAC TCTGTCTCTA      8536

CTAAAAAAAA TACAAAAATT AGCCAGGCAT GGTGGCATGC ACCTGTAATC CCAGCTACTC      8596

GTGAGCCTGA GGCAGAAGAA TCGCTTGAAA CCAGGAGGTG TAGGCTGCAG TGAGCTGAGA      8656

TCGCACCACT GCACTCCAGC CTGGGCGACA GAATGAGACT TTGTCTCAAA AAAAGAAAAA      8716

GATACAACAG GCTACCCTTA TGTGCTCACC TTTCACTGTT GATTACTAGC TATAAAGTCC      8776

TATAAAGTTC TTTGGTCAAG AACCTTGACA ACACTAAGAG GGATTTGCTT TGAGAGGTTA      8836

CTGTCAGAGT CTGTTTCATA TATATACATA TACATGTATA TATGTATCTA TATCCAGGCT      8896

TGGCCAGGGT TCCCTCAGAC TTTCCAGTGC ACTTGGGAGA TGTTAGGTCA ATATCAACTT      8956

TCCCTGGATT CAGATTCAAC CCCTTCTGAT GTAAAAAAAA AAAAAAAAAA GAAAGAAATC      9016

CCTTTCCCCT TGGAGCACTC AAGTTTCACC AGGTGGGGCT TTCCAAGTTG GGGGTTCTCC      9076

AAGGTCATTG GGATTGCTTT CACATCCATT TGCTATGTAC CTTCCCTATG ATGGCTGGGA      9136

GTGGTCAACA TCAAAACTAG GAAAGCTACT GCCCAAGGAT GTCCTTACCT CTATTCTGAA      9196

ATGTGCAATA AGTGTGATTA AAGAGATTGC CTGTTCTACC TATCCACACT CTCGCTTTCA      9256

ACTGTAACTT TCTTTTTTTC TTTTTTTCTT TTTTTCTTTT TTTTTGAAAC GGAGTCTCGC      9316

TCTGTCGCCC AGGCTAGAGT GCAGTGGCAC GATCTCAGCT CACTGCAAGC TCTGCCTCCC      9376

GGGTTCACGC CATTCTCCTG CCTCACCCTC CCAAGCAGCT GGGACTACAG GCGCCTGCCA      9436

CCATGCCCAG CTAATTTTTT GTATTTTTAG TAGAGACGGG GTTTCACCGT GTTAGCCAGG      9496

ATGGTCTCGA TCTCCTGAAC TTGTGATCCG CCCGCCTCAG CCTCCCAAAG TGCTGGGATT      9556

ACAGGCGTGA GCCATCGCAC CCGGCTCAAC TGTAACTTTC TATACTGGTT CATCTTCCCC      9616

TGTAATGTTA CTAGAGCTTT TGAAGTTTTG GCTATGGATT ATTTCTCATT TATACATTAG      9676

ATTTCAGATT AGTTCCAAAT TGATGCCCAC AGCTTAGGGT CTCTTCCTAA ATTGTATATT      9736

GTAGACAGCT GCAGAAGTGG GTGCCAATAG GGGAACTAGT TTATACTTTC ATCAACTTAG      9796

GACCCACACT TGTTGATAAA GAACAAAGGT CAAGAGTTAT GACTACTGAT TCCACAACTG      9856

ATTGAGAAGT TGGAGATAAC CCCGTGACCT CTGCCATCCA GAGTCTTTCA GGCATCTTTG      9916

AAGGATGAAG AAATGCTATT TTAATTTTGG AGGTTTCTCT ATCAGTGCTT AGGATCATGG      9976

GAATCTGTGC TGCCATGAGG CCAAAATTAA GTCCAAAACA TCTACTGGTT CCAGGATTAA     10036
```

```
CATGGAAGAA CCTTAGGTGG TGCCCACATG TTCTGATCCA TCCTGCAAAA TAGACATGCT      10096

GCACTAACAG GAAAAGTGCA GGCAGCACTA CCAGTTGGAT AACCTGCAAG ATTATAGTTT      10156

CAAGTAATCT AACCATTTCT CACAAGGCCC TATTCTGTGA CTGAAACATA CAAGAATCTG      10216

CATTTGGCCT TCTAAGGCAG GGCCCAGCCA AGGAGACCAT ATTCAGGACA GAAATTCAAG      10276

ACTACTATGG AACTGGAGTG CTTGGCAGGG AAGACAGAGT CAAGGACTGC CAACTGAGCC      10336

AATACAGCAG GCTTACACAG GAACCCAGGG CCTAGCCCTA CAACAATTAT TGGGTCTATT      10396

CACTGTAAGT TTTAATTTCA GGCTCCACTG AAAGAGTAAG CTAAGATTCC TGGCACTTTC      10456

TGTCTCTCTC ACAGTTGGCT CAGAAATGAG AACTGGTCAG GCCAGGCATG GTGGCTTACA      10516

CCTGGAATCC CAGCACTTTG GGAGGCCGAA GTGGGAGGGT CACTTGAGGC CAGGAGTTCA      10576

GGACCAGCTT AGGCAACAAA GTGAGATACC CCCTGACCCC TTCTCTACAA AAATAAATTT      10636

TAAAAATTAG CCAATGTGGG TGGTGTATAC TTACAGTCCC AGCTACTCAG GAGGCTGAGG      10696

CAGGGGGATT GCTTGAGCCC AGGAATTCAA GGCTGCAGTG AGCTATGATT TCACCACTGC      10756

ACTTCTGGCT GGGCAACAGA GCGAGACCCT GTCTCAAAGC AAAAAGAAAA GAAACTAGA       10816

ACTAGCCTAA GTTTGTGGGA GGAGGTCATC ATCGTCTTTA GCCGTGAATG GTTATTATAG      10876

AGGACAGAAA TTGACATTAG CCCAAAAAGC TTGTGGTCTT TGCTGGAACT CTACTTAATC      10936

TTGAGCAAAT GTGGACACCA CTCAATGGGA GAGGAGAGAA GTAAGCTGTT TGATGTATAG      10996

GGGAAAACTA GAGGCCTGGA ACTGAATATG CATCCCATGA CAGGGAGAAT AGGAGATTCG      11056

GAGTTAAGAA GGAGAGGAGG TCAGTACTGC TGTTCAGAGA TTTTTTTTAT GTAACTCTTG      11116

AGAAGCAAAA CTACTTTTGT TCTGTTTGGT AATATACTTC AAAACAAACT TCATATATTC      11176

AAATTGTTCA TGTCCTGAAA TAATTAGGTA ATGTTTTTTT CTCTATAG GAA ATG AAT      11233
                                                      Glu Met Asn
                                                                85

CCT CCT GAT AAC ATC AAG GAT ACA AAA AGT GAC ATC ATA TTC TTT CAG       11281
Pro Pro Asp Asn Ile Lys Asp Thr Lys Ser Asp Ile Ile Phe Phe Gln
        90                  95                  100

AGA AGT GTC CCA GGA CAT GAT AAT AAG ATG CAA TTT GAA TCT TCA TCA       11329
Arg Ser Val Pro Gly His Asp Asn Lys Met Gln Phe Glu Ser Ser Ser
    105                 110                 115

TAC GAA GGA TAC TTT CTA GCT TGT GAA AAA GAG AGA GAC CTT TTT AAA       11377
Tyr Glu Gly Tyr Phe Leu Ala Cys Glu Lys Glu Arg Asp Leu Phe Lys
120                 125                 130                 135

CTC ATT TTG AAA AAA GAG GAT GAA TTG GGG GAT AGA TCT ATA ATG TTC       11425
Leu Ile Leu Lys Lys Glu Asp Glu Leu Gly Asp Arg Ser Ile Met Phe
                140                 145                 150

ACT GTT CAA AAC GAA GAC TAGCTATTAA AATTTCATGC C                       11464
Thr Val Gln Asn Glu Asp
            155

(2) INFORMATION FOR SEQ ID NO:14:

(i) SEQUENCE CHARACTERISTICS:
        (A) LENGTH: 28994 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: human
        (F) TISSUE TYPE: placenta (iX) FEATURE:
        (A) NAME/KEY: 5'UTR
```

```
          (B) LOCATION: 1..15606
          (C) IDENTIFICATION METHOD: E
          (A) NAME/KEY: leader peptide
          (B) LOCATION: 15607..15685
          (C) IDENTIFICATION METHOD: S
          (A) NAME/KEY: intron
          (B) LOCATION: 15686..17056
          (C) IDENTIFICATION METHOD: E
          (A) NAME/KEY: leader peptide
          (B) LOCATION: 17057..17068
          (C) IDENTIFICATION METHOD: S
          (A) NAME/KEY: intron
          (B) LOCATION: 17069..20451
          (C) IDENTIFICATION METHOD: E
          (A) NAME/KEY: leader peptide
          (B) LOCATION: 20452..20468
          (C) IDENTIFICATION METHOD: S
          (A) NAME/KEY: mat peptide
          (B) LOCATION: 20469..20586
          (C) IDENTIFICATION METHOD: S
          (A) NAME/KEY: intron
          (B) LOCATION: 20587..21920
          (C) IDENTIFICATION METHOD: E
          (A) NAME/KEY: mat peptide
          (B) LOCATION: 21921..22054
          (C) IDENTIFICATION METHOD: S
          (A) NAME/KEY: intron
          (B) LOCATION: 22055..26827
          (C) IDENTIFICATION METHOD: E
          (A) NAME/KEY: mat peptide
          (B) LOCATION: 26828..27046
          (C) IDENTIFICATION METHOD: S
          (A) NAME/KEY: 3'UTR
          (B) LOCATION: 27047..28994
          (C) IDENTIFICATION METHOD: E (xi) SEQUENCE DESCRIPTION: SEQ ID NO: 14:

ACTTGCCTTA AAAGCTTTGC ATAGGTAGAC AACATTAGAT TAATTTCCTT GCTCACATCT      60

GTTCAAGAAA AATCATTTAA GTTATAAAAT ATAACAAACC TTCTGCATTA TAAGACTGAT     120

GTTTAGAAAT ATAAACATTT TATACATCAC CATTTAAATC TTTCTCCAAG GCTTCATCTT     180

TATAAAATAG TCCGGAAATT TCAGAGAAAG ATGAATCTGA TTTTCCAAGA GAGGACAGCT     240

GTGGACTATC TGGCACTGGA GACTAAATAA AGAAAGCAGG TACAGTCAAT AAGATCTTCA     300

GGACATATAC ATTTTGTTTA TTAAGAAAAA GCAAATAAAA CATTTTTCAG AAAAAGGCAA     360

ACATGCTAGA AAGCATATGA CTTAGTCATT TGAGTTTTTA TTATTAAGGA AATTTACAGG     420

CCCAAGAAAC ACCTTGCTCA ATATATTAAA TTTTATTTTG GTTTTCAACT AGACTTTGCT     480

TTTCATTTGT TTGTTTTTGT GACAAGTTCT CGCTCTGTCA CCTAGGCCAA AGTGTAGTGA     540

CACAATCTTA GCTCACTGTA GCCTCCTAGA TTCAAGTGAT CCTCCTGTCT CAGACTCCTG     600

AGTAGCTAGG ACTACAGGAA CATTCCACCA TGCCCAGCTA ATTTTGTTTT GTTTTGTTTT     660

GTTTTCAGAG ACAATGTATT GCAGCGTTGC CCAGGCTGAT CTGAAACTCT TAGCCTCAAA     720

CGATACTCCT GCCTCAGCCT CCCAAAGCAC TAGGATTACA GACATGAGCC AATGCGCCCA     780

GCCTTAAATT AGACTTTAAA TGTGGTTTTA AACTCCTGTT GAAAAGCGT CTGGTATCTT      840

GAACCAGTAG ATGTTTTCAT AGCAATGAAG CTAAACTGTA ATTTAGACAG TAGCCAAATG     900

CTTGTGAAAT TTTGCTAAAT AATATAATCT TCAAGGGAGC AAATCATGTC CCAAATGCAA     960

AAGATCAACT GGTGGGGGCA GTAGTAAAAG ACAGGATACT GTGCTCTTTA AAAGGTCAGT    1020

AACTATAGTA CCTAGTTATC TTACTTATCA CAGCAAAATA ATTACATAAA ATCCTATGGA    1080

TCATAAAGGC ACAGACTCAC TTCTGTCTCT AGATCTCAAG CTACCAAAAA GAAATCTCCC    1140

AATAGTTTCT TGGAGGCCTA TACTTAGTGA AAAAGCAGCT GGAATCAACA TAGTTCCTCC    1200

TATGTTGTAG GACAATCCTA GCTCTGGGCA TACGAATACA TTAAATCCCA CTTATCTATA    1260
```

```
GAGCTTTCTT AAAGGGAAGA AATTTGAGTA GTATGTAAAA CAGAATAAAA GATTAAGGCT      1320

CCATAGGCAT ACAGCTTACC TCCAATTCTC TTGGCCTCTT GCAATTTCTA TTATCAGGCT      1380

TTACAAGGTG ATTTGCCATC ATATTCCGAA GGCACCAGCT ACAAAGCTTA GAACAATGCC      1440

AGATTTAGGT ACAAACTCCA TGCTACAAGC TCTCTGGAAT CCTTCCCTGT TTCCCACTCC      1500

TACTGCTGAT GTTAATTTAG ACTGTCATTA TCTGTCACTT TCCTAAACTC AATTTCTCCC      1560

TCCTCTAAAT CATTCTATCA ACTGCTATTT GGGTAATCTT TCAAAACTTT GATTACTGCA      1620

TTCCTTTAAC TCAAAAACTT TCATTGTTCC AGAATAAGTT GAAATTCCAT GATATGGCCT      1680

TCAAGGTCCT GTATTATCTG GTGCAAGCCT ACTAGTCCCA TCATTTTCAA CTACTCCTCT      1740

CTATGTACTT AGCCAAATGA GTCTCTCTGG CAATTCTGCC TTGTTTCAGG ACTGGCTCAG      1800

TTAAGATTCT TTTATCTTCG GCCGGGCGCG CTGGCTCACG GCTGTAATCC CAGCACTTTG      1860

GGAAGCTGAG GCAGGAAGAT CACCTGAGGT CGGGAGTTCG AGACCAGCCT GGCCAGCATG      1920

GTGAAACCCT GTGTCTACTA AAAATCCAAA CATTAGCCAG GCGTGGTGGC AGGCGCCTGT      1980

AATCCCAGCT ACTTGGGAAG CTGAGGTGAG AGAATCGCTT GAACCCAGGA GAGGGAGGTT      2040

GCAGTGAGCC GAGATTGTGC CATTGCACTC CAGCCTGGGC AACAGAGCGA GACTCCACCT      2100

CAAAAAAAAA AAGGATTCTT CTATCTTCAC AAAATCTTAA TGTTTAAACA GGTCTTACAG      2160

TTCATCTAAT TCAATCTCAT TTTTTACAAG TGAGAAAACA GGGACAGTGA CGGTGGATCA      2220

AGTGACACCA GTAAGACTGA GCTAAATTAG AACCGAGATC TCACTCGAGT CTGAGGTTAT      2280

TCCCACTGTC CAACCTTACT TTAAAGTAGC TTCAAATTTT ACTTTTACTT TTCCATAAAT      2340

TCGGAAGGGA TTTTCCCTAG GAGTCCAAAT GTTGAAACCT GGAAGGGTAT AGTCTCTGTG      2400

TCTTTGAGAT GAGGGGAGCC CTGTCCATAT TCAAGTTATC AATTGACTTT GTTGTTTTTG      2460

AGAAACGATG CTGATTTGGG TAACTTTAAC ACATCTGTTT GATTAGTCCT ATAAAATATG      2520

CATATATAGA AGACAGAAAG AGCAACAACA AATTTGAAAG ATGCTTGTTA AGTAAATTCT      2580

GTATCGTACG TGTCCATTCC TGCCAGTACC TTTATAGTAT GTAAGTTTAC GTGCTGTAAT      2640

AGTATTAATA GTATCTAGAA AATACTACAC ATGCACAGCA GTGCTAACTT TGCCTTGGGA      2700

GTTGGAAAAT ACTTCAGAGA AGCCAACAGG CAGATTTTTC TCTCTTCCCT TCCCCTTCTA      2760

ATTTTCCCTT TCCCCTTCAC CCCCTTCTCT TCTCTCCCCA AGTAACACTG TGCACCTATG      2820

TCAAACGAAA ACTTATAATC AAGTAACTGT TTCTGCAAAA ATAAGTTCGT TTTCCTGTCA      2880

TGGCTCAAGG CCTCAGCAGA TCCAGGCCTG GTGGACGGGC TGGTCTTCGT CGTGTGCCAA      2940

ACACTGACCA CTGCCCTGGC TCTGCCATCT TAGGCTTAGT GACCTGGCTG TTACTAAGCA      3000

CTGTCCCCTC TGCCCCATGC AGCTGTCTCC TTCTAGTCTT CTCCCTCTTC TCAACGCGAT      3060

CCTAGCCCCT CAGGCCATTT CACCTCCATT TTCCCTCACT TCCCGCCGCC CCTCCGCACT      3120

TCCTCCCTAC TGTTGTTTCC GCCCCACTAG AGCCCCTCAG AGAAAGTTTC CATCCTCGCA      3180

CCCTTCCTTG TGTCACAGCC CGTCACATTC TCACAGGCGC CCATCCCTCC AGCCCCACCC      3240

CAAGGCCAAT GTACTTCGCG GTATGGGGAC CTTCCTCGTC AGCGAACGCG AGGGAGTGAA      3300

GACCCTGGGC GCGGGGTGCT CGGACTTCGG GGGTGGAGGT GGGAAGCGCG CCGCACTCCC      3360

AGCAGCCCCT GCACGAGTCA CGTGACAGCT CTCCCACCAC CACCCCCCCC AACTTCCCCA      3420

CCGTAGCCTC CCAGAGCCAG GCCCCACGGA AAGGCAGCTT TTTCCCGGTT TTCTCCCGCT      3480

CTTTCCCCTC CACTTGGAAT ACTCGTGAAA CAAAAATCTC TCCCTGCCAC CCTGTGTGTG      3540

TTTGAACCAG GAAAAAATCT GAAACTGGTC AAGAAAGAAC AAGGAAGACT TGCCAAAGCA      3600
```

```
AGGCCGGTGT GTGTCCCAGC AGCTTAGAAT CTCAGCAAAG GAACACAAAA TAGCACATCC   3660

ACGGCCTCTT TTCGAGTAAA ATTTACTTGG TTTGTTTGCA GGAAGGGTTT AAAACTGCGT   3720

TTGCAGATGC TCTGTTTGCA GGAAGGCTTT AATCACGTGT TCCCCTGGCC CACAAGCAAG   3780

GCTTTTAGAT CCAGAGCCTC AGTTACTGCC CCCTCTTCCT CTTTGGTGCA ACCAAACGTT   3840

CAGAATCACG CCTTCTTAGA AAATTCTTAC CCCGGGTGTG TCAATAAGTT AAGTCTAATT   3900

GGCAACAGCT ATCAAAAAGT GTTGCATAAC ACACATGGCT CACATAATTG TAGCTTTGCC   3960

TCATCGGGTG TTTTAATGCG GAGGCTTTGA CCTGCAATTT CAAAGATATA CATTCCAAGC   4020

TTACGCCCAG TTAGTGGATG TGGAAGAAAA AAAAAAGCAA ATTACCTCAT AACACAAAGG   4080

TCAATAACAC ACATCCATAA GCTCCAGGTA CAAAATCTTA CATCTTAGAG AACTATATTT   4140

AACATTTACA TACATTACTA AGGTTTTTTT TTTCCTTTTG CTTGATTAAA TGTTAGTTAT   4200

CATTAAGTCT TGGAATTATT CTGTGTGTGT ATATTTATTT GCTGTTTGTG AAGAAGCCGG   4260

TTGTTTTAAA TAAGTTCCTA GAAAATAAGC GCTCAATGTG TTTAATCTGA GTTGCTAATA   4320

TTGTGAAATA TAGGCCACAT AATACTAGCC TAGATAACTA TGGCGAAGTA AGGAGTCTCA   4380

AACACTGTCC CAGAACAATA GCAATCTGTG TTGAATTTTT ACCCTCTGTG GTAAAATGAA   4440

GGGAAAAGGA ATGAAGTTTT AGTTTGCCTT AATTTTTATC TTTATTGTTT CAGACTCTTC   4500

AGCAGTATAA AGTTTTCATC AAGTCAAATA TATTCACTTT AAAGTGACTG TGCTTTATTC   4560

TGATACCATG TCCTTCCTAA TTTGGGGGGC CAGGTGAGAT AAGTTTTATG AAATAAAAAG   4620

ATTAAAAATT CTTACATTTT TAGTGTCCTT CCTTGGTAAA ATGTAGAGTT GTCCACTGTG   4680

TTTATCTCCT CCTCCTTATT ATCATGGTTG CTGTTATTAT TTTTAATGGT TCATTAAACC   4740

CAAGGGTCTG GGAAATACTC ATGGAATTCA TCTCACAGCC TTCACACTGT ATGATATTTA   4800

AACAGGTGGT TGTCCATCTG ATTCTTAAAA TATTTCCAAG AAAAATGATT CCACCTAATG   4860

CATAAATGCT TTCATCAGAT TAAGAGAACA CCATGGACAT TTTATTTTAT TTTATTTTTT   4920

AAATATTAAC TTCCATTGCA TAAGCTAAAT GGGTAGGAAT AAGTGAGATG ATATTGTTAT   4980

CTAGAGCTTT AAAATATTCA AAGGGCTGTC ATCATTATCT CATTTAATCT TTGAAAACAA   5040

CTCTATGAAG TACAAAGGAC ACTGAGACAT TTGTTGCTCT ATATCAAAGA AAAAAGTGTT   5100

TGTCCCAAAA CTTCAAAATG TGTAAATTAC ACATTCTGCA TCTTTACAGC TGGAGAAAAT   5160

TCACTGGCAA TGGAATATTT AAAATTAGAG CTTGCTTAGT GTGCTGCTTC TGATCACTAC   5220

TTGATCCCAC TTCGTGCTTT CATGTTAATT GGCCCAATTG GACTCTACAG TTGGAAGGTG   5280

AAAACTTACT ATTTCAACTT GAGTCACGTA TGTATTCTTA TCATATACTT CTTAAAGGTA   5340

CTATTTTTTT TCTTCTGATA GTCACCACAC CAAGCACTTC CAGCCACCCT GCCACAGACT   5400

TCCTTTGTAA TCACTGTTGA AGGACATGAT GTTTTTATGA CTTCCCGAAA TGAAACCCT    5460

ATCTTGTTTT TAAAACAAAC AAACCAACAA AAAGTAGTGT TTATGTAAGC ATTTTGTTCC   5520

CTGACTCTAG GAACCCCTCT GTTTTTATAT CAACTCTGTA CTGGCAAAAC ACAAAAACAA   5580

AATGCCACCT TGCTAATTCC CTTCCTAGCA AAGTAATACA GTTAGCACA  TGTTCAAGAA   5640

AAAAATGGCT AAGAAATTTT GTTTCCACTA ATTATTTTCA AGACTGTGAT ATTTACACTC   5700

TGCTCTTCAA ACGTTACATT TTATAAGACT ATTTTTTAAC ATGTTGAACA TAAGCCCTAA   5760

ATATATGTAT CCTTAAATTG TATTTCAAAT ATTTTAGGTC AGTCTTTGCT ATCATTCCAG   5820

GAATAGAAAG TTTTAACACT GGAAACTGCA AGTAAATATT TGCCCTCTTA CCTGAATTTT   5880

GGTAGCCCTC TCCCCAAGCT TACTTTCTGT TGCAGAAAGT GTAAAATTA  TTACATAAAA   5940

TTCTAATGAT GGTATCCGTG TGGCTTGCAT CTGATACAGC AGATAAAGAA GTTTTATGAA   6000
```

```
AATGGACTCC TGTTCCACTG AAAAGTAAAT CTTAATGGCC TGTATCAACT ATCCTTTGAC      6060

ACCATATTGA GCTTGGGAGG AAGGGGAAGT CCTGAATGAG GTTATAAAGT AAAAGAAAAT      6120

ATTTGCAAAA TGTTCCTTTT TTTAAAATGT TACATTTTAG AAATATTTTA AGTGTTGTAA      6180

CATTGTAGGA ATTACCCCAA TAGGACTGAT TATTCCGCAT TGTAAAATAA GAAAAAGTTT      6240

TGTGCTGAAG TGTGACCAGG AAGTCTGAAA ATGAAGAGAG ACAGATGACA AAAGAAGATG      6300

CTTCTAATGG ACTAAGGAGG TGCTTTCTTA AAGTCAGAAA GAGATACTCA GAAAGAGGTA      6360

CAGGTTTTGG AAGGCACAGA GCCCCAACTT TTACGGAAGA AAAGATTTCA TGAAAATAGT      6420

GATATTACAT TAAAAGAAGT ACTCGTATCC TCTGCCACTT TATTTCGACT TCCATTGCCC      6480

TAGGAAAGAG CCTGTTTGAA GGCGGGCCCA AGGAGTGCCG ACAGCAGTCT CCTCCCTCCA      6540

CCTTCTTCCT CATTCTCTCC CCAGCTTGCT GAGCCCTTTG CTCCCCTGGC GACTGCCTGG      6600

ACAGTCAGCA AGGAATTGTC TCCCAGTGCA TTTTGCCCTC CTGGCTGCCA ACTCTGGCTG      6660

CTAAAGCGGC TGCCACCTGC TGCAGTCTAC ACAGCTTCGG GAAGAGGAAA GGAACCTCAG      6720

ACCTTCCAGA TCGCTTCCTC TCGCAACAAA CTATTTGTCG CAGGTAAGAA ATATCATTCC      6780

TCTTTATTTG GAAAGTCAGC CATGGCAATT AGAGGTAAAT AAGCTAGAAA GCAATTGAGA      6840

GGAATATAAA CCATCTAGCA TCACTACGAT GAGCAGTCAG TATCAACATA GAAATATAA      6900

GCAAAGTCAG AGTAGAATTT TTTTCTTTTA TCAGATATGG GAGAGTATCA CTTTAGAGGA      6960

GAGGTTCTCA AACTTTTTGC TCTCATGTTC CCTTTACACT AAGCACATCA CATGTTAGCA      7020

TAAGTAACAT TTTAATTAA AAATAACTAT GTACTTTTTT AACAACAAAA AAAAGCATAA      7080

AGAGTGACAC TTTTTTATTT TTACAAGTGT TTTAACTGGT TTAATAGAAG CCATATAGAT      7140

CTGCTGGATT TCATCTGCT TTGCATTCAG ACTACTGCAA TATTGCACAG AATGCAGCCT      7200

CTGGTAAACT CTGTTGTACA CTCATGAGAG AATGGGTGAA AAAGACAAAT TACGTCTTAG      7260

AATTATTAGA AATAGCTTTC ACTTTAGGAA CTCCCTGAGA ATTGCTGCTT TAGAGTGGTA      7320

AGATAAATAA GCTTCTCTTT AAACGGAATC TCAAGACAGA ATCAGTTACA TTAAAAGCAA      7380

ACAAAAAATT TGCCCATGGT TAGTCATCTT GTGAAATCTG CCACACCTTT GGACTGGGCT      7440

ACAATTGGAT AATATAGCAT TCCCCGAGAT AATTTTCTCT CACAATTAAG GAAAGGGCTG      7500

AATAAATATC TCTGTTTGAA GTTGAATAAC AAAAATTAGG ACCCCCTAAA TTTTAGGGCT      7560

CCTGAAATTC GTCTTTTTGC CTATATTCAG CTACTTTACG TTCTATTAAA TCTTCTTTCA      7620

GGCCAGGTGC ACTAGCTCAT GCCTAGAATC TCAGGCAGGC CTGAGCCCAG GAATTTGAGA      7680

CCAGCCAGGG CAACACAGTC TCTACAAAAA AATAAAAAAT TACCTGGGTG TGTTGGTGCA      7740

TGCCTGTAGA ACTACTCAGG ATGCTGAGGA CTGCTTGAGC CCAGGATAGC CAAATCTGTG      7800

GTGAGTTCAG CCACTAAACA GAGCGAGACT TTCTCAAAAA AACAAACAAA AAAACAAACA      7860

AACTTCCTTC AAAATAACTT TTTATCTGCA ATGTTTTCCT ATTGCCTGTG AGATTAAATT      7920

TACTCTTTTA CCTGATTTCC AAAGCCCTCC ATAATCTAAT CCGACTTTAC CTTGTGTTCA      7980

CTGCAAAATA GCAGGACTGT TCCACTACAA TCCAAAAATC ACAGGTTGGG TGCAGTGGCT      8040

CACTCCTGTA ATCCCAACAC TTTGGAAGGC CAAGGCAGGT GGATTGCTTC AGCTCAGGAG      8100

TTCAAGACCA GCCTGGGCAA CATGGCAAAA ACCCTGTCTC TCCAAAACAT ACAAAAATTA      8160

GCCAGATGTG GTAGTATGTG CCTGTAGTCC CAACTACTCA AAAGGCTAAG GCAAGAGGAT      8220

CACTTGAGCC CAGGAGGTCA AGGCTACAGT GAGCCATGTT TACTGTGTCA CTGCACTCCA      8280

GCCTGGGTGA TAGAGCAAGA CCATGTCTCA AAAAAAAAAA AAAGAAAAGA AAAGAAAAAA      8340
```

```
ACATCGCTCT ATTCAGTTCA CCCCCACCAC AACATTGTTT TGATTATCAC ATAAATGCTG    8400

GTCCATTGCC TTCTCTATCT ATTCAAATCT TTAAGCATTC TTTGAGATTC AACTCAATTC    8460

TCCTTTTCAA ACTAGGCCAT TTAAACTACA TCAGTTCCAT TTTGATTTTC TTGCTTTGAG    8520

TCTACAGACT CAAAAACAAA AACTTAAAAA CTTATTTTTT AAGTTTTCTG CTACTCTCAC    8580

TTCTTCAACA CTCACATACA CGCATTCATA ATAAGATGGC AGAATGTTCA AGGATAAAAT    8640

GATTTATAGA ACTGAAAAGT TAGGTTTTGA TCTTGTTGCT GTCAAGATGA CTACCTACCT    8700

GATCTCAGGT AATTAATTAT GTAGCATGCT CCCTCATTTC ATCCCATACC TATTCAACAG    8760

GATTGGAATT CCACAGCAAG GATAAACATA ATCATAGTTG CTTTTCAAGT TCAAGGCATT    8820

TTAACTTTTA ATCTAGTAGT ATGTTTGTTG TTGTTGTTGT TGTTTGAGAT GGAGCCCTGC    8880

TGTGTCACCC AGGCTGGAGT GCAGTGGCAC GAACTCGGCT CACTGCAACC TCTGCCTCAT    8940

GGGTTCAATC AGTTATTCTG CCTCAGTGTC CCAAGTAGCT GGGACTACAA GGCACATGCC    9000

ACCATGCCTG GCTAATTTTT GTATTTTTAG TAGAAACAGG GCTTCACCAT GTTGGCCAGG    9060

CTGGTCTCGA ACTCCTGACC TCAAGTGATC CAGCCGCCTC GGCCTCCCAA AGTGCTGGGA    9120

TTACAGGCAT AAGCCACCGT GCCCAGCCTA ATAGTATGTT TTTAAACTCT TAGTGGCTTA    9180

ACAATGCTGG TTGTATAATA AATATGCCAT AAATATTTAC TGTCTTAGAA TTATGAAGAA    9240

GTGGTTACTA GGCCGTTTGC CACATATCAA TGGTTCTCTC CTTACAGCTT TAATTAGAGT    9300

CTAGAATTGC AGGTTGGTAG AGCTGGAACA GACCTTAAAG ATTGACTAGC CAACTTCCTT    9360

GTCCAAATGA GGGAACTGAG ACCCTTAAAA TTAAGTGACT TGCCCCAGAC AAAACTGGAA    9420

CTCATGTGTC CTAATTTCCA TCATGAAATT CTACCATTCA CTAGCCTCTG GCTAGTTGTC    9480

AAAGTATTGC ATAACTAAAT TTTTATGTCT GTTTTAAAGA ACAAATTGTC ACTGCTTACT    9540

CCTGGGAGGG TCTTTCTGAG GTGGTTTATA ACTCTTAAAA AAAAAAAGT CAGTAGTCTG     9600

AGAATTTTAG ACGAAATAGT CAAAGCATTT TTATCCAATG GATCTATAAT TTTCATAGAT    9660

TAGAGTTAAA TCAAAGAAAC ACGGATGAGA AAGGAAGAGG AAAATTGAGG AGAGGAGGAA    9720

TGGGGATGAG AACACACTAC TTGTAATCAG TCATAGATGT ACTGAGAACT AACAAGAAGA    9780

ATTGTAAGAA AATAAGAATG AAGAATTCAA AATCAACACA TGAAATAAAA AGAAACTACT    9840

AGGGAAAAAT GGAGAAGACA TTAGAAAAAT TATTCTATTT TTAAAATTCT GTTTTCAGGC    9900

TTCCCTCCTG TTCTTCCTCC TTCTCATTGG TTTTCAGGTG GAGGGAAAGT TTAAGATGGA    9960

AAAAATATAT ATATTCTACA CATCCCTTTC TACGCTGTTG TCATGGCAAC AAGGTTTATC   10020

ATAGCAAACT TTTATTCATA CAACATTTAT TGAGTTCTTA CTGTGTGGTA AGCTCTTTCC   10080

AGGTGTTGAA AATTCAGGGG AAAAAAGACA ACTCATTGTC TTAAAACTCA GATGAAAGCT   10140

GAACAGACCT ATTTTTAATC AAAGTAATCT CAATTTAGGG TAGTAAGAGC TATTTAAGAA   10200

GCATGAACAG GTGTGAAGGA GGTAGGACTC TGAGGAGAGA ATAGTTAGCT AGGAATGAAA   10260

GAGCAGAGAA GTTTTCCTAG AGGAACTATT AAAGCTGGGA GTTACGGGAT GAAAGATGAG   10320

GCAGGGTTTG CAGGCAAAAA AAAAAAAAAG GCAGGGAAG GGGAAGTTCT GGCCTGGCAG    10380

AGAGAATAAC TGTGGCAACA ATGGAGGAGA GTCTGGAAGC AAGAAAACCA AGTAGAAGAG   10440

TATTAAAATA GAAGATGCCA GGGGTAATGA GGGCTTGATT TAAACAGTG CTGTTGGAGA    10500

TGGAGAGGAG ATACCAAATT CTGGAGACAT TTCTGAGTTA GAACCTACAG TATTTATCAG   10560

ACAAGGGAAA GATTAGACAA AGGAGTTAAG AATGACTCCC AGGTTTCAGT TTGGGGCAGG   10620

TAACTAGGAC ATGTTTTGAA AAGTAATGTA TTGGATCTCT TACCATTGGA ACTATGTATG   10680

TGGAGCCAAA TTAAAATTTG TACATGTATA TAACTCTCCC CCCACCACCA GTAACTACTT   10740
```

```
CCCTAACTCT CTACTTTGTA GCCAGACTTC CTAAAAGAAT AGTTTGTAGT CACTGTCTTT    10800

ACTTTTCCCC TCCCATTCTG TCCTAGATAT TTGTCCACCT ACCATCTGCT GCCTCCACTT    10860

TACCCAAACT GTTCTACGGT TGCCCAAAAC TTCCTAATTG CCAAATTCAA TGAACAAGTT    10920

TAAGCTTATA TGTAAATTAG GAGCTCTACA GTTTGATTTC GAGCAGCCCC TCCTGAAACC    10980

CTTTCTCTTT CGACTTCTGT GACACATCTC AGATTTACAA AACTGAACTA ATTATTTTAC    11040

ACTTGAGCTG TATTTTCGTT CTTCTTTCTT GATGAATGAG GTAACCACTC AACAAATTGC    11100

CCAAGCCAAA AACTACGAAG TCATCCTCAG TTCCTCCTTC TTCTGTTTGA CCCACAACAG    11160

ATCAGCTGAG AAATCCCGCT GTTTAGTATC TCTTGAATTC ATTACCTTAA TTTATAGCCT    11220

CATCAACTCT TAATTGTTAA AATTACTTCA GTAGTTGTTG TCTGACCTCT GTCCAATCTT    11280

GTTCAATCAG GTCCATTCTT TTGTTCTTGG TGGTGGTGGT GGTGTTGACA GAGTTTCGCT    11340

TTTGCTGCCC AGGCTGAAGT GCAGTGGAGC ACTTCACTGC AACCACAGCC TCCTGGGTTT    11400

AAGCAGTTCA CCCTCCCGAG TAGCTGGGAC TACAGGTATG TGCCACCACA CCCAGCTAAT    11460

TTTGTGTTTT CAGTAGAGAC AGGGTTTCAC CATGTTGGTC AGGCTGGTCT CAAACTCCTG    11520

ACCTCAAGCA ATCCACCCAC CTCAGCCTCC CAAAGTGCTG GGATTACAGG CATGAGCCAC    11580

TGCACACGGA CCAGATCCAT TGTTTATGTT GCTTCTAGAG TGAGTTTTTA AAACACAAAT    11640

TTGACCATAT CTTTCTCCAA TTTAAGTCAG TATTTTTTTT TTCAGGAAAA AACAGTTCAA    11700

ACTCTTTAGT CTGCTTACAC AAGGCCTTTG TAGTCTGACT CTTCTTTCCA AGCTTTCATC    11760

AAAGTATACT GCAAGTTACA TTTTATGTGA ATTGAATTAG GCAACGGTAT AAAAATTATA    11820

GTTTATATGG GCAAAATGGA AATAATGTTA ACTCTTCCAA ATAGTTTATC TAGAATGACA    11880

TAATTTCAAA GCTGTCAGGT CAAATGAGTT ATAAACTGTT AACACTATTG CCACATGCAA    11940

GTGTCTCTTA TACTTGGTAG AATTATCTGC TTCCATGTCA TTATTATGTA AATTAGACTT    12000

TAAATAACTC AGAAGTTCTT CAGACATACA GGTTATTATT GTGCTTTTTA AACATAATTT    12060

TAAATAATTT TATATATGAT AATGTTATCC AAGTGCTAAG GGATGTATTG TTACTGCTGT    12120

GCAAAAAAAA AAAAAAAAAA AACTCCAAAT AAATATGTTG AAACCAAGTT TATATGCAAG    12180

AAAACAATAT TAAAAGGCC AAAGTACCAC CATAATAGGC TGTGTGGAGA CGGCAGGCTA    12240

CAAAACACTA GTAATAATGC TGAGAAAGTT GAAAAAGAA AGAAAGCAAC AATATGCTTT    12300

GGTTGTTGTA GGTTTATGTA CTCCAAGAAT ATCTCCTCTC AAACTTTTAC GTTTTTTCCA    12360

AAGAAAAGTT AACTTTGGCT GGGCGCAGTG GCTCTTGCCT GTAGTCCCAG CCTTTGGGAG    12420

GCCAAGGCGG GCAGATCACC TGAGGTCAGG AGTTTGAGAC CAGCCTGACC AAAAATGGAG    12480

AAACCCGCCC CCCTCACTAC TAAAAGAATA CAAAATTAGG CCGGGCACAG TGGCTTACCC    12540

CTGTGATCCC AGCACTTTGG GAGGCCGAAG CAGGAAGATC ACCTGAGGTC AGGAGTTCGA    12600

GACCAGCCAT GGAGAAACCC GTCTCTACTA AAAATACAAA ATTAGCCGGG CGTGGTGGTG    12660

CATGACTGTA ATCCCAGCTA CTCAGGAGGC TAAGGCAGAG AATCACTTGA ACCCAGGCAG    12720

TGGAGGTTGC AGTGAGCCGA GATCGTGCCA TTGCACTCCA GCCTGGGCAA CAAGAGCGAA    12780

ACTCTGTATC CAAAAACAA AAGAAAAGAA AAGGTAACCT TGAACTATGT GAGATCTTTA    12840

GAAATGCATT CTTTCTGTAA AATGTGACTA CATTTGCCTT ATTTATGGTA AAAATGTTGA    12900

GGCCTCAAAC AACCCATATT TTCTCGGTCT CCCCGCTGCC TAGCCTTTGT TCACATTGCT    12960

TCTTCTTGGT GGAAGCTCTT CCTCTGGCCT TGAAAATGCC TGCTTCTCTT TCAAGGTAGC    13020

ACAGTCATCA CTTTCTGTGG TAACCTTCTC CAGCACCATC AAACAGAAAG AATGAATCTC    13080
```

-continued

```
TTGTAAATTC AGCTCTTACG TCATTCATTA CATTATTTTG TAACTCTTTA TAGATTCTTC    13140

TCTCCCACTA GACTCTGAGT CACTGGAGAG TAGGAGCCAA CTCTCATTCA TGTGTGGTTT    13200

GGTCAGCTAC TGGCCACATT CCTGATGCAT AGTAATGCT CAAACCTTAA CTGGTGAATC     13260

AGCTCAAATA TTGTCCTTCT CTAAATCCAT TCACTCATTG ACTAACTATG TACTCAAAAT    13320

AGTAAACACC AGTAATTTAA TCCAATTCCT GCCCATACTG CTTGGTACAT TTCAGGTGAA    13380

TTAGTTTGAT AAATATGTGT GTATTACATA ATATTAAAGT ATGTACAGAA GATCATGCTA    13440

ATCATAATTC ACAACTGATA ACTAATCAAA CATAAATGCT CTCAGGTTAA CAAATGTCTG    13500

CCTTCTCAGT TAATGCAGTC ATTAACAAAC ACCTTCTGAT GCTGATAATA GGGCCTTGTT    13560

CAGCAATGAA GCCATAAAGG TGAATAAAGA ACATGCCCTC GTGGAGCTCA CAGCCTAGTC    13620

ATTATTGTTC TGATTTTTAA TATTAATGTT GGTTTGGGTT TTGGTGAAAA ATGTTTAGAC    13680

TTATCTTAGT GATCTTTTCA TCCTTTGCTA TATTATTTTT CTCTAAGAGT CTTCCTTATC    13740

CCCTCCTTTA AAAAACTAGG TGATAATTCT AAATTGTAAA TTTAAATATT ATAAATAGCT    13800

TATAAAATTT AATATTTATA ATATTTAAAT GTTTGATAAA TATTTAAATT TTATAATATT    13860

TAAATGTTTA TTTAAATTCA TTTGTACATC AGTTTTTATT TTATTTAAAT GTGTTGGCCA    13920

GGCATGGTGG CTGACACCTA TAATCCCAGA ACTTTGAGAG GCCAAGTCAG GCAAACCATT    13980

TGAGCTCAGG AGTTTGAGAC CACCCTGGGC AACGTGGTGA AACCCTGTCT CTACCAAACA    14040

TATGAAAACT TATCTGGGTG TGGTGGCACG CATCTGTGGT CCCAGATGGG AGTCCCAGGC    14100

TAAGATGGGA GAATCGCTTG AACCCAGGTG AGAGGGTGG GGTGGATGTT GCAGTGAGCT     14160

GAGATCGTGC CACTGCACTC CAACCTGGGT GACAGAGTGA GACTCCATCT CAAAAAAAAA    14220

AAATGTTATC TAAATAAGAT AAATTTAATA ACTGTTCGCA CTTAGATGAG CATAAGGAAC    14280

TAAACCTAGA TAAAACTATC AAATAAGGCC TGGGTACAGT GACTCATGCC TGTAATCTCA    14340

AGCACTTTGG GAGGCCAAAA TTATACAAAG TTAGTTGTAT AACACCAACT AACAACTATT    14400

TTGGGGTTAG CTTAATTCAG ATTAATTTTT TTTAAACTGA GTTTTAAATT CCTGCTTACT    14460

CTACCATACA TGCTAGGCCT CATATTATGC TAGAAAAATT TTGAGCACAG ATTTATGAAT    14520

ACTCTCCTGC ATACCATTTA ATTTTTAAAC AAATTTTAAT GCAGTATATA TGTGCCTTTT    14580

TACCAACACA TTAAATAATA AGATCTACTG TGAGGACTAA ATTTCTGTAA TTTCAAAGTA    14640

GTAATGAGTT TAAACCATGT CTCAAGATCT CTGCAATAAC TGTAGCACAA CAGAAAATAG    14700

GTATTTCTAT TAATGACAGA GTCACAAGTA CTACTAATAA TACTGTGGTT TGTTTCCTGC    14760

AACTAATCAT GGGAGGAATG CTAAATTTCA GAGGTTGGTG AAAATACATG TGTATTTTTT    14820

TCCCCATCCA AGTTCACAGA TTTCTCACAC TGAGAACTCC TATTCCATAA CAAAATTCTG    14880

GAAGCCTGCA CACCGTATTG AAGAAGGGC AGAAAGGAAA AGCAAATGGA AGGATTTAAA     14940

TTTTTTTCAA ATCCTGTATC CCTTGATTTT ACAGCAAGAT TGTATTTATG TATTACTTGT    15000

GTTAAAAATA TAGTATAATC GAGACTCCAG ATCAAAAATC ACCGCAGCTC AGGGAGAAAG    15060

AGGGCCACCA AATGCCAGAG CCCTTCAGCC TTCTCCCACC CTGCCTGTAC CCTCAGATGG    15120

AAGCACTTTT TTATCATTGT TTCACCTTTA GCATTTTGAC AATGAAGTCA CAAACCTTCA    15180

GCCTCTCACC CATAGGAACC CACTGGTTGT AAGAGAAGGA TGAAGCCAGT CCTTCCTAAA    15240

GGGCACGATT AGATGTGTTT ATGGCATCCT CAGGTGAAAC TATATTTATA TTGACAATAT    15300

ATTTATATTT CTCAAGGAAT ACTAGAATAA TGATTCAGTT CAGTACTAGG CCATTTATCT    15360

ACCCTTTATA ATATTGTTTA ATGAGAAAAT GCTTTCTATC TTCCAAATAT CTGATGATTT    15420

GTAAGAGAAC ACTTAAACAT GGGTATTCAT AAGCTGAAAC TTCTGGCATT TATTGAATGT    15480
```

```
CAAGATTGTT CATCAGTATA CTAGGTGATT AACTGACCAC TGAACTTGAA GGTAGTATAA    15540

AGTAGTAGTA AAAGGTACAA TCATTGTCTC TTAACAGATG GCTCTTTGCT TTCATTAGGA    15600

ATAAAG ATG GCT GCT GAA CCA GTA GAA GAC AAT TGC ATC AAC TTT GTG GCA  15651
       Met Ala Ala Glu Pro Val Glu Asp Asn Cys Ile Asn Phe Val Ala
           -35             -30                 -25

ATG AAA TTT ATT GAC AAT ACG CTT TAC TTT ATA G    GTAAGC TAATGCCATA  15702
Met Lys Phe Ile Asp Asn Thr Leu Tyr Phe Ile Ala
    -20             -15              -10

GAACAAATAC CAGGTTCAGA TAAATCTATT CAATTGAGAA AGATGTTGTG AGGTGAACTA    15762

TTAAGTGACT CTTTGTGTCA CCAAATTTCA CTGTAATATT AATGGCTCTT AAAAAAATAG    15822

TGGACCTCTA GAAATTAACC ACAACATGTC CAAGGTCTCA GCACCTTGTC ACACCACGTG    15882

TCCTGGCACT TTAATCAGCA GTAGCTCACT CTCCAGTTGG CAGTAAGTGC ACATCATGAA    15942

AATCCCAGTT TTCATGGGAA ATCCCAGTT  TTCATTGGAT TCCATGGGA  AAAATCCCAG    16002

TACAAAACTG GGTGCATTCA GGAAATACAA TTTCCCAAAG CAAATTGGCA AATTATGTAA    16062

GAGATTCTCT AAATTTAGAG TTCCGTGAAT TACACCATTT TATGTAAATA TGTTTGACAA    16122

GTAAAAATTG ATTCTTTTTT TTTTTTTCTG TTGCCCAGGC TGGAGTGCAG TGGCACAATC    16182

TCTGCTCACT GCAACCTCCA CCTCCTGGGT TCAAGCAATT CTCCTGCCTC AGCCTTCTGA    16242

GTAGCTGGGA CTACAGGTGC ATCCCGCCAT GCCTGGCTAA TTTTTGGGTA TTTTTACTAG    16302

AGACAGGGTT TTGGCATGTT GTCCAGGCTG GTCTTGGACT CCTGATCTCA GATGATCCTC    16362

CTGGCTCGGG CTCCCAAAGT GCTGGGATTA CAGGCATGAA CCACCACACA TGGCCTAAAA    16422

ATTGATTCTT ATGATTAATC TCCTGTGAAC AATTTGGCTT CATTTGAAAG TTTGCCTTCA    16482

TTTGAAACCT TCATTTAAAA GCCTGAGCAA CAAAGTGAGA CCCCATCTCT ACAAAAAACT    16542

GCAAAATATC CTGTGGACAC CTCCTACCTT CTGTGGAGGC TGAAGCAGGA GGATCACTTG    16602

AGCCTAGGAA TTTGAGCCTG CAGTGAGCTA TGATCCCACC CCTACACTCC AGCCTGCATG    16662

ACAGTAGACC CTGACACACA CACACAAAAA AAAACCTTCA TAAAAAATTA TTAGTTGACT    16722

TTTCTTAGGT GACTTTCCGT TTAAGCAATA AATTTAAAAG TAAAATCTCT AATTTTAGAA    16782

AATTTATTTT TAGTTACATA TTGAAATTTT TAAACCCTAG GTTTAAGTTT TATGTCTAAA    16842

TTACCTGAGA ACACACTAAG TCTGATAAGC TTCATTTTAT GGGCCTTTTG GATGATTATA    16902

TAATATTCTG ATGAAAGCCA AGACAGACCC TTAAACCATA AAAATAGGAG TTCGAGAAAG    16962

AGGAGTAGCA AAAGTAAAAG CTAGAATGAG ATTGAATTCT GAGTCGAAAT ACAAAATTTT    17022

ACATATTCTG TTTCTCTCTT TTTCCCCCTC TTAG  CT GAA GAT GAT G    GTAAAGT  17075
                                      Ala Glu Asp Asp Glu
                                                -10

AGAAATGAAT TTATTTTTCT TTGCAAACTA AGTATCTGCT TGAGACACAT CTATCTCACC    17135

ATTGTCAGCT GAGGAAAAAA AAAAATGGTT CTCATGCTAC CAATCTGCCT TCAAAGAAAT    17195

GTGGACTCAG TAGCACAGCT TTGGAATGAA GATGATCATA AGAGATACAA AGAAGAACCT    17255

CTAGCAAAAG ATGCTTCTCT ATGCCTTAAA AAATTCTCCA GCTCTTAGAA TCTACAAAAT    17315

AGACTTTGCC TGTTTCATTG GTCCTAAGAT TAGCATGAAG CCATGGATTC TGTTGTAGGG    17375

GGAGCGTTGC ATAGGAAAAA GGGATTGAAG CATTAGAATT GTCCAAAATC AGTAACACCT    17435

CCTCTCAGAA ATGCTTTGGG AAGAAGCCTG GAAGGTTCCG GGTTGGTGGT GGGGTGGGGC    17495

AGAAAATTCT GGAAGTAGAG GAGATAGGAA TGGGTGGGGC AAGAAGACCA CATTCAGAGG    17555

CCAAAAGCTG AAAGAAACCA TGGCATTTAT GATGAATTCA GGGTAATTCA GAATGGAAGT    17615
```

-continued

| | |
|---|---|
| AGAGTAGGAG TAGGAGACTG GTGAGAGGAG CTAGAGTGAT AAACAGGGTG TAGAGCAAGA | 17675 |
| CGTTCTCTCA CCCCAAGATG TGAAATTTGG ACTTTATCTT GGAGATAATA GGGTTAATTA | 17735 |
| AGCACAATAT GTATTAGCTA GGGTAAAGAT TAGTTTGTTG TAACAAAGAC ATCCAAAGAT | 17795 |
| ACAGTAGCTG AATAAGATAG AGAATTTTTC TCTCAAAGAA AGTCTAAGTA GGCAGCTCAG | 17855 |
| AAGTAGTATG GCTGGAAGCA ACCTGATGAT ATTGGGACCC CCAACCTTCT TCAGTCTTGT | 17915 |
| ACCCATCATC CCCTAGTTGT TGATCTCACT CACATAGTTG AAAATCATCA TACTTCCTGG | 17975 |
| GTTCATATCC CAGTTATCAA GAAAGGGTCA AGAGAAGTCA GGCTCATTCC TTTCAAAGAC | 18035 |
| TCTAATTGGA AGTTAAACAC ATCAATCCCC CTCATATTCC ATTGACTAGA ATTTAATCAC | 18095 |
| ATGGCCACAC CAAGTGCAAG GAAATCTGGA AAATATAATC TTTATTCCAG GTAGCCATAT | 18155 |
| GACTCTTTAA AATTCAGAAA TAATATATTT TTAAAATATC ATTCTGGCTT TGGTATAAAG | 18215 |
| AATTGATGGT GTGGGTGAG GAGGCCAAAA TTAAGGGTTG AGAGCCTATT ATTTTAGTTA | 18275 |
| TTACAAGAAA TGATGGTGTC ATGAATTAAG GTAGACATAG GGGAGTGCTG ATGAGGAGCT | 18335 |
| GTGAATGGAT TTTAGAAACA CTTGAGAGAA TCAATAGGAC ATGATTTAGG GTTGGATTTG | 18395 |
| GAAAGGAGAA GAAAGTAGAA AAGATGATGC CTACATTTTT CACTTAGGCA ATTTGTACCA | 18455 |
| TTCAGTGAAA TAGGGAACAC AGGAGGAAGA GCAGGTTTTG GTGTATACAA AGAGGAGGAT | 18515 |
| GGATGACGCA TTTCGTTTTG GATCTGAGAT GTCTGTGGAA CGTCCTAGTG GAGATGTCCA | 18575 |
| CAAACTCTTC TACATGTGGT TCTGAGTTCA GGACACAGAT TTGGGCTGGA GATAGAGATA | 18635 |
| TTGTAGGCTT ATACATAGAA ATGGCATTTG AATCTATAGA GATAAAAAGA CACATCAGAG | 18695 |
| GAAATGTGTA AAGTGAGAGA GGAAAAGCCA AGTACTGTGC TGGGGGGAAT ACCTACATTT | 18755 |
| AAAGGATGCA GTAGAAAGAA GCTAATAAAC AACAGAGAGC AGACTAACCA AAAGGGGAGA | 18815 |
| AGAAAAACCA AGAGAATTCC ACCGACTCCC AGGAGAGCAT TTCAAGATTG AGGGGATAGG | 18875 |
| TGTTGTGTTG AATTTTGCAG CCTTGAGAAT CAAGGGCCAG AACACAGCTT TTAGATTTAG | 18935 |
| CAACAAGGAG TTTGGTGATC TCAGTGAAAG CAGCTTGATG GTGAAATGGA GGCAGAGGCA | 18995 |
| GATTGCAATG AGTGAAACAG TGAATGGGAA GTGAAGAAAT GATACAGATA ATTCTTGCTA | 19055 |
| AAAGCTTGGC TGTTAAAAGG AGGAGAGAAA CAAGACTAGC TGCAAAGTGA GATTGGGTTG | 19115 |
| ATGGAGCAGT TTTAAATCTC AAAATAAAGA GCTTTGTGCT TTTTTGATTA TGAAAATAAT | 19175 |
| GTGTTAATTG TAACTAATTG AGGCAATGAA AAAAGATAAT AATATGAAAG ATAAAAATAT | 19235 |
| AAAAACCACC CAGAAATAAT GATAGCTACC ATTTTGATAC AATATTTCTA CACTCCTTTC | 19295 |
| TATGTATATA TACAGACACA GAAATGCTTA TATTTTATT AAAAGGGATT GTACTATACC | 19355 |
| TAAGCTGCTT TTTCTAGTTA GTGATATATA TGGACATCTC TCCATGGCAA CGAGTAATTG | 19415 |
| CAGTTATATT AAGTTCATGA TATTTCACAA TAAGGGCATA TCTTTGCCCT TTTTATTTAA | 19475 |
| TCAATTCTTA ATTGGTGAAT GTTTGTTTCC AGTTTGTTGT TGTTATTAAC AATGTTCCCA | 19535 |
| TAAGCATTCC TGTACACCAA TGTTCACACA TTTGTCTGAT TTTTTCTTCA GGATAAAACC | 19595 |
| CAGGAGGTAG AATTGCTGGG TTGATAGAAG AGAAAGGATG ATTGCCAAAT TAAAGCTTCA | 19655 |
| GTAGAGGGTA CATGCCGAGC ACAAATGGGA TCAGCCCTAG ATACCAGAAA TGGCACTTTC | 19715 |
| TCATTTCCCC TTGGGACAAA AGGGAGAGAG GCAATAACTG TGCTGCCAGA GTTAAATTTG | 19775 |
| TACGTGGAGT AGCAGGAAAT CATTTGCTGA AAATGAAAAC AGAGATGATG TTGTAGAGGT | 19835 |
| CCTGAAGAGA GCAAAGAAAA TTTGAAATTG CGGCTATCAG CTATGGAAGA GAGTGCTGAA | 19895 |
| CTGGAAAACA AAAGAAGTAT TGACAATTGG TATGCTTGTA ATGGCACCGA TTTGAACGCT | 19955 |
| TGTGCCATTG TTCACCAGCA GCACTCAGCA GCCAAGTTTG GAGTTTTGTA GCAGAAAGAC | 20015 |

```
AAATAAGTTA GGGATTTAAT ATCCTGGCCA AATGGTAGAC AAAATGAACT CTGAGATCCA    20075

GCTGCACAGG GAAGGAAGGG AAGACGGGAA GAGGTTAGAT AGGAAATACA AGAGTCAGGA    20135

GACTGGAAGA TGTTGTGATA TTTAAGAACA CATAGAGTTG GAGTAAAAGT GTAAGAAAAC    20195

TAGAAGGGTA AGAGACCGGT CAGAAAGTAG GCTATTTGAA GTTAACACTT CAGAGGCAGA    20255

GTAGTTCTGA ATGGTAACAA GAAATTGAGT GTGCCTTTGA GAGTAGGTTA AAAAACAATA    20315

GGCAACTTTA TTGTAGCTAC TTCTGGAACA GAAGATTGTC ATTAATAGTT TTAGAAAACT    20375

AAAATATATA GCATACTTAT TTGTCAATTA ACAAAGAAAC TATGTATTTT TAAATGAGAT    20435

TTAATGTTTA TTGTAG  AA AAC CTG GAA TCA GAT TAC TTT GGC AAG CTT GAA   20486
                  Glu Asn Leu Glu Ser Asp Tyr Phe Gly Lys Leu Glu
                       -5                  1                   5

TCT AAA TTA TCA GTC ATA AGA AAT TTG AAT GAC CAA GTT CTC TTC ATT     20534
Ser Lys Leu Ser Val Ile Arg Asn Leu Asn Asp Gln Val Leu Phe Ile
             10                  15                  20

GAC CAA GGA AAT CGG CCT CTA TTT GAA GAT ATG ACT GAT TCT GAC TGT     20582
Asp Gln Gly Asn Arg Pro Leu Phe Glu Asp Met Thr Asp Ser Asp Cys
             25                  30                  35

AGA G   GT ATTTTTTTTA ATTCGCAAAC ATAGAAATGA CTAGCTACTT CTTCCCATTC   20638
Arg Asp
     40

TGTTTTACTG CTTACATTGT TCCGTGCTAG TCCCAATCCT CAGATGAAAA GTCACAGGAG   20698

TGACAATAAT TTCACTTACA GGAAACTTTA TAAGGCATCC ACGTTTTTTA GTTGGGGTAA   20758

AAAATTGGAT ACAATAAGAC ATTGCTAGGG GTCATGCCTC TCTGAGCCTG CCTTTGAATC   20818

ACCAATCCCT TTATTGTGAT TGCATTAACT GTTTAAAACC TCTATAGTTG GATGCTTAAT   20878

CCCTGCTTGT TACAGCTGAA AATGCTGATA GTTTACCAGG TGTGGTGGCA TCTATCTGTA   20938

ATCCTAGCTA CTTGGGAGGC TCAAGCAGGA GGATTGCTTG AGGCCAGGAC TTTGAGGCTG   20998

TAGTACACTG TGATCGTACC TGTGAATAGC CACTGCACTC CAGCCTGGGT GATATACAGA   21058

CCTTGTCTCT AAAATTAAAA AAAAAAAAAA AAAAACCTT AGGAAAGGAA ATTGATCAAG    21118

TCTACTGTGC CTTCCAAAAC ATGAATTCCA AATATCAAAG TTAGGCTGAG TTGAAGCAGT   21178

GAATGTGCAT TCTTTAAAAA TACTGAATAC TTACCTTAAC ATATATTTTA AATATTTTAT   21238

TTAGCATTTA AAAGTTAAAA ACAATCTTTT AGAATTCATA TCTTTAAAAT ACTCAAAAAA   21298

GTTGCAGCGT GTGTGTTGTA ATACACATTA AACTGTGGGG TTGTTTGTTT GTTTGAGATG   21358

CAGTTTCACT CTGTCACCCA GGCTGAAGTG CAGTGCAGTG CAGTGGTGTG ATCTCGGCTC   21418

ACTACAACCT CCACCTCCCA CGTTCAAGCG ATTCTCATGC CTCAGTCTCC CGAGTAGGTG   21478

GGATTACAGG CATGCACCAC TTACACCCGG CTAATTTTTG TATTTTTAGT AGAGCTGGGG   21538

TTTCACCATG TTGGCCAGGC TGGTCTCAAA CCCCTAACCT CAAGTGATCT GCCTGCCTCA   21598

GCCTCCCAAA CAAACAAACA ACCCCACAGT TTAATATGTG TTACAACACA CATGCTGCAA   21658

CTTTTATGAG TATTTTAATG ATATAGATTA TAAAAGGTTG TTTTTAACTT TTAAATGCTG   21718

GGATTACAGG CATGAGCCAC TGTGCCAGGC CTGAACTGTG TTTTTAAAAA TGTCTGACCA   21778

GCTGTACATA GTCTCCTGCA GACTGGCCAA GTCTCAAAGT GGGAACAGGT GTATTAAGGA   21838

CTATCCTTTG GTTAAATTTC CGCAAATGTT CCTGTGCAAG AATTCTTCTA ACTAGAGTTC   21898

TCATTTATTA TATTTATTTC AG  AT AAT GCA CCC CGG ACC ATA TTT ATT ATA   21949
                         Asp Asn Ala Pro Arg Thr Ile Phe Ile Ile
                                      40                  45

AGT ATG TAT AAA GAT AGC CAG CCT AGA GGT ATG GCT GTA ACT ATC TCT    21997
Ser Met Tyr Lys Asp Ser Gln Pro Arg Gly Met Ala Val Thr Ile Ser
```

| | | | | | | | | | | | | |
|---|---|---|---|---|---|---|---|---|---|---|---|---|
| 50 | | | | 55 | | | | 60 | | | 65 | |
| GTG | AAG | TGT | GAG | AAA | ATT | TCA | ACT | CTC | TCC | TGT | GAG | AAC | AAA | ATT | ATT | 22045 |
| Val | Lys | Cys | Glu | Lys | Ile | Ser | Thr | Leu | Ser | Cys | Glu | Asn | Lys | Ile | Ile | |
| | | | | 70 | | | | 75 | | | | 80 | | | | |

```
TCC TTT AAG GTAAGACTG AGCCTTACTT TGTTTTCAAT CATGTTAATA TAATCAATAT    22103
Ser Phe Lys

AATTAGAAAT ATAACATTAT TTCTAATGTT AATATAAGTA ATGTAATTAG AAAACTCAAA    22163
TATCCTCAGA CCAACCTTTT GTCTAGAACA GAAATAACAA GAAGCAGAGA ACCATTAAAG    22223
TGAATACTTA CTAAAAATTA TCAAACTCTT TACCTATTGT GATAATGATG GTTTTTCTGA    22283
GCCTGTCACA GGGGAAGAGG AGATACAACA CTTGTTTTAT GACCTGCATC TCCTGAACAA    22343
TCAGTCTTTA TACAAATAAT AATGTAGAAT ACATATGTGA GTTATACATT TAAGAATAAC    22403
ATGTGACTTT CCAGAATGAG TTCTGCTATG AAGAATGAAG CTAATTATCC TTCTATATTT    22463
CTACACCTTT GTAAATTATG ATAATATTTT AATCCCTAGT TGTTTTGTTG CTGATCCTTA    22523
GCCTAAGTCT TAGACACAAG CTTCAGCTTC CAGTTGATGT ATGTTATTTT TAATGTTAAT    22583
CTAATTGAAT AAAAGTTATG AGATCAGCTG TAAAAGTAAT GCTATAATTA TCTTCAAGCC    22643
AGGTATAAAG TATTTCTGGC CTCTACTTTT TCTCTATTAT TCTCCATTAT TATTCTCTAT    22703
TATTTTTCTC TATTTCCTCC ATTATTGTTA GATAAACCAC AATTAACTAT AGCTACAGAC    22763
TGAGCCAGTA AGAGTAGCCA GGGATGCTTA CAAATTGGCA ATGCTTCAGA GGAGAATTCC    22823
ATGTCATGAA GACTCTTTTT GAGTGGAGAT TTGCCAATAA ATATCCGCTT TCATGCCCAC    22883
CCAGTCCCCA CTGAAAGACA GTTAGGATAT GACCTTAGTG AAGGTACCAA GGGGCAACTT    22943
GGTAGGGAGA AAAAGCCAC TCTAAAATAT AATCCAAGTA AGAACAGTGC ATATGCAACA    23003
GATACAGCCC CCAGACAAAT CCCTCAGCTA TCTCCCTCCA ACCAGAGTGC CACCCCTTCA    23063
GGTGACAATT TGGAGTCCCC ATTCTAGACC TGACAGGCAG CTTAGTTATC AAAATAGCAT    23123
AAGAGGCCTG GGATGGAAGG GTAGGGTGGA AAGGGTTAAG CATGCTGTTA CTGAACAACA    23183
TAATTAGAAG GGAAGGAGAT GGCCAAGCTC AAGCTATGTG GGATAGAGGA AAACTCAGCT    23243
GCAGAGGCAG ATTCAGAAAC TGGGATAAGT CCGAACCTAC AGGTGGATTC TTGTTGAGGG    23303
AGACTGGTGA AAATGTTAAG AAGATGGAAA TAATGCTTGG CACTTAGTAG AACTGGGCA    23363
AATCCATATT TGGGGGAGCC TGAAGTTTAT TCAATTTTGA TGGCCCTTTT AAATAAAAAG    23423
AATGTGGCTG GGCGTGGTGG CTCACACCTG TAATCCCAGC ACTTTGGGAG GCCGAGGGGG    23483
GCGGATCACC TGAAGTCAGG AGTTCAAGAC CAGCCTGACC AACATGGAGA AACCCCATCT    23543
CTACTAAAAA TACAAAATTA GCTGGGCGTG GTGGCATATG CCTGTAATCC CAGCTACTCG    23603
GGAGGCTGAG GCAGGAGAAT CTTTTGAACC CGGGAGGCAG AGGTTGCGAT GAGCCTAGAT    23663
CGTGCCATTG CACTCCAGCC TGGGCAACAA GAGCAAAACT CGGTCTCAAA AAAAAAAAA     23723
AAAAAGTGAA ATTAACCAAA GGCATTAGCT TAATAATTTA ATACTGTTTT TAAGTAGGGC    23783
GGGGGGTGGC TGGAAGAGAT CTGTGTAAAT GAGGGAATCT GACATTTAAG CTTCATCAGC    23843
ATCATAGCAA ATCTGCTTCT GGAAGGAACT CAATAAATAT TAGTTGGAGG GGGGGAGAGA    23903
GTGAGGGGTG GACTAGGACC AGTTTTAGCC CTTGTCTTTA ATCCCTTTTC CTGCCACTAA    23963
TAAGGATCTT AGCAGTGGTT ATAAAAGTGG CCTAGGTTCT AGATAATAAG ATACAACAGG    24023
CCAGGCACAG TGGCTCATGC CTATAATCCC AGCACTTTGG GAGGGCAAGG CGAGTGTCTC    24083
ACTTGAGATC AGGAGTTCAA GACCAGCCTG GCCAGCATGG CGATACTCTG TCTCTACTAA    24143
AAAAAATACA AAAATTAGCC AGGCATGGTG GCATGCACCT GTAATCCCAG CTACTCGTGA    24203
```

-continued

```
GCCTGAGGCA GAAGAATCGC TTGAAACCAG GAGGTGTAGG CTGCAGTGAG CTGAGATCGC   24263

ACCACTGCAC TCCAGCCTGG GCGACAGAAT GAGACTTTGT CTCAAAAAAA GAAAAAGATA   24323

CAACAGGCTA CCCTTATGTG CTCACCTTTC ACTGTTGATT ACTAGCTATA AAGTCCTATA   24383

AAGTTCTTTG GTCAAGAACC TTGACAACAC TAAGAGGGAT TTGCTTTGAG AGGTTACTGT   24443

CAGAGTCTGT TTCATATATA TACATATACA TGTATATATG TATCTATATC CAGGCTTGGC   24503

CAGGGTTCCC TCAGACTTTC CAGTGCACTT GGGAGATGTT AGGTCAATAT CAACTTTCCC   24563

TGGATTCAGA TTCAACCCCT TCTGATGTAA AAAAAAAAAA AAAAAAGAAA GAAATCCCTT   24623

TCCCCTTGGA GCACTCAAGT TTCACCAGGT GGGGCTTTCC AAGTTGGGGG TTCTCCAAGG   24683

TCATTGGGAT TGCTTTCACA TCCATTTGCT ATGTACCTTC CCTATGATGG CTGGGAGTGG   24743

TCAACATCAA AACTAGGAAA GCTACTGCCC AAGGATGTCC TTACCTCTAT TCTGAAATGT   24803

GCAATAAGTG TGATTAAAGA GATTGCCTGT TCTACCTATC CACACTCTCG CTTTCAACTG   24863

TAACTTTCTT TTTTTCTTTT TTTCTTTTTT TCTTTTTTTT TGAAACGGAG TCTCGCTCTG   24923

TCGCCCAGGC TAGAGTGCAG TGGCACGATC TCAGCTCACT GCAAGCTCTG CCTCCCGGGT   24983

TCACGCCATT CTCCTGCCTC ACCCTCCCAA GCAGCTGGGA CTACAGGCGC CTGCCACCAT   25043

GCCCAGCTAA TTTTTTGTAT TTTTAGTAGA GACGGGGTTT CACCGTGTTA GCCAGGATGG   25103

TCTCGATCTC CTGAACTTGT GATCCGCCCG CCTCAGCCTC CCAAAGTGCT GGGATTACAG   25163

GCGTGAGCCA TCGCACCCGG CTCAACTGTA ACTTTCTATA CTGGTTCATC TTCCCCTGTA   25223

ATGTTACTAG AGCTTTTGAA GTTTTGGCTA TGGATTATTT CTCATTTATA CATTAGATTT   25283

CAGATTAGTT CCAAATTGAT GCCCACAGCT TAGGGTCTCT TCCTAAATTG TATATTGTAG   25343

ACAGCTGCAG AAGTGGGTGC CAATAGGGGA ACTAGTTTAT ACTTTCATCA ACTTAGGACC   25403

CACACTTGTT GATAAAGAAC AAAGGTCAAG AGTTATGACT ACTGATTCCA CAACTGATTG   25463

AGAAGTTGGA GATAACCCCG TGACCTCTGC CATCCAGAGT CTTTCAGGCA TCTTTGAAGG   25523

ATGAAGAAAT GCTATTTTAA TTTTGGAGGT TTCTCTATCA GTGCTTAGGA TCATGGGAAT   25583

CTGTGCTGCC ATGAGGCCAA AATTAAGTCC AAAACATCTA CTGGTTCCAG GATTAACATG   25643

GAAGAACCTT AGGTGGTGCC CACATGTTCT GATCCATCCT GCAAAATAGA CATGCTGCAC   25703

TAACAGGAAA AGTGCAGGCA GCACTACCAG TTGGATAACC TGCAAGATTA TAGTTTCAAG   25763

TAATCTAACC ATTTCTCACA AGGCCCTATT CTGTGACTGA AACATACAAG AATCTGCATT   25823

TGGCCTTCTA AGGCAGGGCC CAGCCAAGGA GACCATATTC AGGACAGAAA TTCAAGACTA   25883

CTATGGAACT GGAGTGCTTG GCAGGGAAGA CAGAGTCAAG GACTGCCAAC TGAGCCAATA   25943

CAGCAGGCTT ACACAGGAAC CCAGGGCCTA GCCCTACAAC AATTATTGGG TCTATTCACT   26003

GTAAGTTTTA ATTTCAGGCT CCACTGAAAG AGTAAGCTAA GATTCCTGGC ACTTTCTGTC   26063

TCTCTCACAG TTGGCTCAGA AATGAGAACT GGTCAGGCCA GGCATGGTGG CTTACACCTG   26123

GAATCCCAGC ACTTTGGGAG GCCGAAGTGG GAGGGTCACT TGAGGCCAGG AGTTCAGGAC   26183

CAGCTTAGGC AACAAAGTGA GATACCCCCT GACCCCTTCT CTACAAAAAT AAATTTTAAA   26243

AATTAGCCAA ATGTGGTGGT GTATACTTAC AGTCCCAGCT ACTCAGGAGG CTGAGGCAGG   26303

GGGATTGCTT GAGCCCAGGA ATTCAAGGCT GCAGTGAGCT ATGATTTCAC CACTGCACTT   26363

CTGGCTGGGC AACAGAGCGA GACCCTGTCT CAAAGCAAAA AGAAAAGAA ACTAGAACTA   26423

GCCTAAGTTT GTGGGAGGAG GTCATCATCG TCTTTAGCCG TGAATGGTTA TTATAGAGGA   26483

CAGAAATTGA CATTAGCCCA AAAAGCTTGT GGTCTTTGCT GGAACTCTAC TTAATCTTGA   26543

GCAAATGTGG ACACCACTCA ATGGGAGAGG AGAGAAGTAA GCTGTTTGAT GTATAGGGGA   26603
```

-continued

```
AAACTAGAGG CCTGGAACTG AATATGCATC CCATGACAGG GAGAATAGGA GATTCGGAGT      26663

TAAGAAGGAG AGGAGGTCAG TACTGCTGTT CAGAGATTTT TTTTATGTAA CTCTTGAGAA      26723

GCAAAACTAC TTTTGTTCTG TTTGGTAATA TACTTCAAAA CAAACTTCAT ATATTCAAAT      26783

TGTTCATGTC CTGAAATAAT TAGGTAATGT TTTTTTCTCT ATAG GAA ATG AAT CCT      26839
                                                  Glu Met Asn Pro
                                                           85

CCT GAT AAC ATC AAG GAT ACA AAA AGT GAC ATC ATA TTC TTT CAG AGA       26887
Pro Asp Asn Ile Lys Asp Thr Lys Ser Asp Ile Ile Phe Phe Gln Arg
         90              95              100

AGT GTC CCA GGA CAT GAT AAT AAG ATG CAA TTT GAA TCT TCA TCA TAC       26935
Ser Val Pro Gly His Asp Asn Lys Met Gln Phe Glu Ser Ser Ser Tyr
105         110             115                          120

GAA GGA TAC TTT CTA GCT TGT GAA AAA GAG AGA GAC CTT TTT AAA CTC       26983
Glu Gly Tyr Phe Leu Ala Cys Glu Lys Glu Arg Asp Leu Phe Lys Leu
                 125             130                 135

ATT TTG AAA AAA GAG GAT GAA TTG GGG GAT AGA TCT ATA ATG TTC ACT       27031
Ile Leu Lys Lys Glu Asp Glu Leu Gly Asp Arg Ser Ile Met Phe Thr
             140             145             150

GTT CAA AAC GAA GAC T AGCTATTAAA ATTTCATGCC GGGCGCAGTG GCTCACGCCT     27087
Val Gln Asn Glu Asp
         155

GTAATCCCAG CCCTTTGGGA GGCTGAGGCG GGCAGATCAC CAGAGGTCAG GTGTTCAAGA     27147

CCAGCCTGAC CAACATGGTG AAACCTCATC TCTACTAAAA ATACAAAAAA TTAGCTGAGT     27207

GTAGTGACCC ATGCCCTCAA TCCCAGCTAC TCAAGAGGCT GAGGCAGGAG AATCACTTGC     27267

ACTCCGGAGG TGGAGGTTGT GGTGAGCCGA GATTGCACCA TTGCGCTCTA GCCTGGGCAA     27327

CAACAGCAAA ACTCCATCTC AAAAAATAAA ATAAATAAAT AAACAAATAA AAATTCATA      27387

ATGTGAACTG TCTGAATTTT TATGTTTAGA AAGATTATGA GATTATTAGT CTATAATTGT     27447

AATGGTGAAA TAAAATAAAT ACCAGTCTTG AAAAACATCA TTAAGAAATG AATGAACTTT     27507

CACAAAAGCA AACAAACAGA CTTTCCCTTA TTTAAGTGAA TAAAATAAAA TAAAATAAAA     27567

TAATGTTTAA AAAATTCATA GTTTGAAAAC ATTCTACATT GTTAATTGGC ATATTAATTA     27627

TACTTAATAT AATTATTTTT AAATCTTTTG GGTTATTAGT CCTAATGACA AAAGATATTG     27687

ATATTTGAAC TTTCTAATTT TTAAGAATAT CGTTAAACCA TCAATATTTT TATAAGGAGG     27747

CCACTTCACT TGACAAATTT CTGAATTTCC TCCAAAGTCA GTATATTTTT AAAATTCAGT     27807

TTGATCCTGA ATCCAGCAAT ATATAAAAGG GATTATATAC TCTGGCCAAC TGACATTCAT     27867

CCTAGGAATG CAAAGATGGT TTAATATCCT AAAATCAATT AACATAACAT ACTATATTAA     27927

TAAAGTATCA AAACAGTATT CTCATCTTTT TTTCTTTTTT CACAATTCCT TGGTTACACT     27987

ATCATCTCAA TAGATGCAGA AAAAGCATTT GACAAAATCC AATTCATAAT AAAAATTCTC     28047

AAACTTGAAA GAGAACATCA TAAAGGCATC TATGAAAAAC CTACAGCTAA TATCATACTT     28107

AACGATGAAA AACTGAATTA TTTTACCCTA AGATCAAGAA TAATGCAAGC ATGTCAGCTC     28167

TTGCAACTTC TATTCAACAT TGTACTGGAG GTTCTAGCCA GAGCAACCAT ACAATAAATA     28227

AAAATAAAAG GCACCCAGAT TAGAAAGGAA GTCTTTATTT GCAGACAACA TGGTTCTTTA     28287

TGCAGAAAAC CGTCAGGAAT ACACACACAT GTTAGAACTA ATAAGTTCAG CAAGGTTGCA     28347

GGTTGCAATA TCAATATGCA AAAATACATT GAAGGCTGGG CTCAGTGGAG ATGGCATGTA     28407

CCTTTCGTCC CAGCTACTTG GGAGGCTGAG GTAGGAGGAT CACTTGAGGT GAGGAGTTTG     28467

AGGCTATAGT GCAATGTGAT CTTGCCTGTG AATAGCCACT GCACTCGAGC CTAGGCAACA     28527
```

-continued

```
AAGTGAGACC CCGTCTCCAA AAAAAAAAAT GGTATATTGG TATTTCTGTA TATGAACAAT    28587

GAATGATCTG AAAACAAGAA AATTCCATTC ACGATGGTAT TAAAAAAATA AAATACAAAT    28647

AAATTTAGCA AAATAATTAT AAAACTTGTA CATCGAAAAT TTCAAAGCAC TCTGAGGGAA    28707

ATTAAAGATG ATCTAAATAA TTGGAGAGAC ACTCTATGAT CACTGATTGG AAAATTCATT    28767

CAATATTGTT AAGATAACAA TTGTCCCCAA ATTGATGCAT GCATTCAATT TAGTCTTCAT    28827

CAAAATTCCA GCAGGGTTTT TGCAGAAATT GACAAGCTGT ACCCAAAATG TATATGGAAA    28887

TGAAAAGACC CAGAAGAGCA AATAATTTTT TAAAAACAAA GTTGGAAAAC TTTTACTTCC    28947

TAATTTTAAA ACTTACTATA AACCTAAAGT TATCAAGACC ATTTAGT                 28994
```

(2) INFORMATION FOR SEQ ID NO: 15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: N-terminal fragment (xi) SEQUENCE DESCRIPTION: SEQ ID NO: 15:

```
Tyr Phe Gly Lys Leu Glu Ser Lys Leu Ser
1               5                   10
```

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
CCATCCTAAT ACGACTCACT ATAGGGC                                          27
```

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
TTCCTCTTCC CGAAGCTGTG TAGACTGC                                         28
```

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
CTATAGGGCA CGCGTGGT                                                    18
```

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TTCCTCTTCC CGAAGCTGTG TAGACTGC                                        28

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GTAAGTTTTC ACCTTCCAAC TGTAGAGTCC                                    30

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GGGATCAAGT CGTGATCAGA AGCAGCACAC                                    30

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CCTGGCTGCC AACTCTGGCT GCTAAAGCGG                                    30

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GTATTGTCAA TAAATTTCAT TGCCACAAAG TTG                                  33

(2) INFORMATION FOR SEQ ID NO:24:

(i) SEQUENCE CHARACTERISTICS:
        (A) LENGTH: 33 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

AAGATGGCTG CTGAACCAGT AGAAGACAAT TGC                33

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

TCCTTGGTCA ATGAAGAGAA CTTGGTC                       27

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CCTGGAATCA GATTACTTTG GCAAGCTTGA ATC                33

(2) INFORMATION FOR SEQ ID NO:27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GGAAATAATT TTGTTCTCAC AGGAGAGAGT TG                 32

(2) INFORMATION FOR SEQ ID NO:28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GCCAGCCTAG AGGTATGGCT GTAACTATCT C                  31

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GGCATGAAAT TTTAATAGCT AGTCTTCGTT TTG				33

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GTGACATCAT ATTCTTTCAG AGAAGTGTCC				30

(2) INFORMATION FOR SEQ ID NO:31:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GCAATTTGAA TCTTCATCAT ACGAAGGATA C				31

(2) INFORMATION FOR SEQ ID NO:32:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

TCCGAAGCTT AAGATGGCTG CTGAACCAGT A				31

(2) INFORMATION FOR SEQ ID NO:33:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GGAAATAATT TTGTTCTCAC AGGAGAGAGT TG				32

(2) INFORMATION FOR SEQ ID NO:34:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
ATGTAGCGGC CGCGGCATGA AATTTTAATA GCTAGTC                                      37

(2) INFORMATION FOR SEQ ID NO:35:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

CCTGGAATCA GATTACTTTG GCAAGCTTGA ATC                                          33
```